(12) United States Patent
Beswick et al.

(10) Patent No.: US 11,180,531 B2
(45) Date of Patent: Nov. 23, 2021

(54) BICYCLIC PEPTIDE LIGANDS SPECIFIC FOR NECTIN-4

(71) Applicant: BicycleTx Limited, Cambridge (GB)

(72) Inventors: Paul Beswick, Cambridge (GB); Liuhong Chen, Cambridge (GB); Gemma Mudd, Cambridge (GB); Peter Park, Lincoln, MA (US); Katerine Van Rietschoten, Cambridge (GB); Michael Rigby, Cambridge (GB)

(73) Assignee: BicycleTx Limited, Cambridge (GB)

( * ) Notice: Subject to any disclaimer, the term of this patent is extended or adjusted under 35 U.S.C. 154(b) by 0 days.

(21) Appl. No.: 16/446,901

(22) Filed: Jun. 20, 2019

(65) Prior Publication Data

US 2019/0389906 A1 Dec. 26, 2019

(30) Foreign Application Priority Data

| Jun. 22, 2018 | (GB) | 1810250 |
| Sep. 26, 2018 | (GB) | 1815684 |
| Nov. 13, 2018 | (GB) | 1818499 |
| Apr. 2, 2019 | (GB) | 1904632 |

(51) Int. Cl.
| *A61K 38/00* | (2006.01) |
| *C07K 7/08* | (2006.01) |
| *A61K 47/65* | (2017.01) |
| *A61K 47/55* | (2017.01) |
| *A61P 35/00* | (2006.01) |
| *A61K 31/40* | (2006.01) |
| *A61K 31/5375* | (2006.01) |

(52) U.S. Cl.
CPC .............. *C07K 7/08* (2013.01); *A61K 47/55* (2017.08); *A61K 47/65* (2017.08); *A61P 35/00* (2018.01); *A61K 31/40* (2013.01); *A61K 31/5375* (2013.01); *A61K 38/00* (2013.01)

(58) Field of Classification Search
CPC combination set(s) only.
See application file for complete search history.

(56) References Cited

U.S. PATENT DOCUMENTS

| 7,390,799 B2 | 6/2008 | Bruncko et al. |
| 8,138,347 B2 | 3/2012 | Knight et al. |
| 2019/0307836 A1* | 10/2019 | Keen .................... A61P 35/00 |
| 2021/0040154 A1 | 2/2021 | Mudd et al. |
| 2021/0069287 A1 | 3/2021 | Mudd et al. |
| 2021/0101937 A1 | 4/2021 | Mudd et al. |

FOREIGN PATENT DOCUMENTS

| WO | WO-2001042246 A2 | 6/2001 |
| WO | WO-2002088112 A1 | 11/2002 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |
| WO | WO-2005007623 A2 | 1/2005 |
| WO | WO-2005113554 A2 | 12/2005 |
| WO | WO-2006029879 A2 | 3/2006 |
| WO | WO-2006078846 A1 | 7/2006 |
| WO | WO-2006105021 A2 | 10/2006 |
| WO | WO-2006122806 A2 | 11/2006 |
| WO | WO-2007005874 A2 | 1/2007 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2008039218 A2 | 4/2008 |
| WO | WO-2008109943 A1 | 9/2008 |
| WO | WO-2008118802 A1 | 10/2008 |
| WO | WO-2008132601 A1 | 11/2008 |
| WO | WO-2009009116 A2 | 1/2009 |
| WO | WO-200944273 A2 | 4/2009 |
| WO | WO-2009073620 A2 | 6/2009 |
| WO | WO-2009098450 A2 | 8/2009 |
| WO | WO-2009114512 A1 | 9/2009 |
| WO | WO-2010019570 A2 | 2/2010 |
| WO | WO-2010077634 A1 | 7/2010 |
| WO | WO-2011028683 A1 | 3/2011 |

(Continued)

OTHER PUBLICATIONS

Curran A. Rhodes and Dehua Pei, Bicyclic Peptides as Next-Generation Therapeutics, 2017, Chem. Eur. J. 2017, 23, 12690-12703 (Year: 2017).*

JI Johnson et al. Relationships between drug activity in NCI preclinical in vitro and in vivo models and early clinical trials. 2001. British Journal of Cancer (2001) 84(10), 1424-1431 (Year: 2001).*

Edward A. Sausville and Angelika M. Burger. Contributions of Human Tumor Xenografts to Anticancer Drug Development. 2006. Cancer Res 2006; 66: (7). Apr. 1, 2006 (Year: 2006).*

(Continued)

*Primary Examiner* — James H Alstrum-Acevedo
*Assistant Examiner* — Mercy H Sabila
(74) *Attorney, Agent, or Firm* — Andrea L. C. Reid; Gang Wang; Dechert LLP

(57) ABSTRACT

The present invention relates to polypeptides which are covalently bound to molecular scaffolds such that two or more peptide loops are subtended between attachment points to the scaffold. In particular, the invention describes peptides which are high affinity binders of Nectin-4. The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder mediated by Nectin-4.

24 Claims, 30 Drawing Sheets

Specification includes a Sequence Listing.

(56) References Cited

FOREIGN PATENT DOCUMENTS

| WO | WO-2011056652 A1 | 5/2011 | |
|---|---|---|---|
| WO | WO-2011070024 A1 | 6/2011 | |
| WO | WO-2011090760 A1 | 7/2011 | |
| WO | WO-2011107553 A1 | 9/2011 | |
| WO | WO-2011109400 A2 | 9/2011 | |
| WO | WO-2011131407 A1 | 10/2011 | |
| WO | WO-2011140249 A2 | 11/2011 | |
| WO | WO-2012142237 A1 | 10/2012 | |
| WO | WO-2012145493 A1 | 10/2012 | |
| WO | WO-201387699 A1 | 6/2013 | |
| WO | WO-2013079174 A1 | 6/2013 | |
| WO | WO-2013119716 A1 | 8/2013 | |
| WO | WO-2013132044 A1 | 9/2013 | |
| WO | WO-2013169264 A1 | 11/2013 | |
| WO | WO-2014008218 A1 | 1/2014 | |
| WO | WO-2014036357 A1 | 3/2014 | |
| WO | 2016067035 | 5/2016 | |
| WO | WO-2016067035 A1 * | 5/2016 | ......... A61K 51/0482 |
| WO | WO-2019243832 A1 | 12/2019 | |
| WO | WO-2021019243 A1 | 2/2021 | |
| WO | WO-2021064428 A1 | 4/2021 | |

OTHER PUBLICATIONS

Satoshi Nishiwada et al. Nectin-4 expression contributes to tumor proliferation, angiogenesis and patient prognosis in human pancreatic cancer. 2015. Journal of Experimental & Clinical Cancer Research (2015) 34:30 (Year: 2015).*
Sumit Siddharth et al. Nectin-4 is a breast cancer stem cell marker that induces WNT/β-catenin signaling via Pi3k/Akt axis, 2017. International Journal of Biochemistry and Cell Biology 89 (2017) 85-94 (Year: 2017).*
National cancer institute, Cancer prevention overview, 2020 (Year: 2020).*
National cancer institute, What is Cancer? 2015 (Year: 2015).*
Merck Manual consumer version, Cancer treatment principles, Jul. 2018 (Year: 2018).*
Merck Manual consumer version, Overview of Cancer therapy, Jul. 2018 (Year: 2018).*
Medical news Today, What are the most curable cancers? (Year: 2020).*
Heinis et al., "Phage-encoded combinatorial chemical libraries based on bicyclic peptides", Nature Chemical Biology, vol. 5, No. 7, May 31, 2009; pp. 502-507, XP002588840.
Chen at al., "Peptide Ligands Stabilized by Small Molecules", Angewandte Chemie, International Edition, vol. 53, No. 6, Feb. 3, 2014, pp. 1602-1606, XP55356354.
International Search Report and Written Opinion dated Aug. 5, 2019 for PCT/GB2019/051741.
Adams et al., "Big Opportunities for Small Molecules in Immuno-oncology," Nature Reviews, 2015, vol. 14, pp. 603-622.
Chang et al., "Subtiligase: A Tool for Semisynthesis of Proteins," Proc Natl Acad Sci, 1994, vol. 91(26), pp. 12544-12548.
Chen and Harrison, "Cell-Penetrating Peptides in Drug Development: Enabling Intracellular Targets," Biochemical Society Transactions, 2007, vol. 35(4), p. 821.
Cherney et al., "Macrocyclic Amino Carboxylates as Selective MMP-8 Inhibitors," J. Med. Chem., 1998, vol. 41, pp. 1749-1751.
Connolly et al., "Complexities of TGF-β Targeted Cancer Therapy," Int'l J. Biological Sciences, 2012, vol. 8, pp. 964-978.
Dawson et al., "Synthesis of Proteins by Native Chemical Ligation," Science, 1994, vol. 266, pp. 776-779.
Derossi et al., "The Third Helix of the Antennapedia Homeodomain Translocates Through Biological Membranes," J. Biol. Chem., 1994, vol. 269, pp. 10444-10450.
Driggers et al., "The Exploration of Macrocycles for Drug Discovery—an Underexploited Structural Class," Nat Rev Drug Discov, 2008, vol. 7(7), pp. 608-624.

Elson-Scwab et al., "Guanidinylated Neomycin Delivers Large, Bioactive Cargo into Cells Through a Heparan Sulfate-Dependent Pathway," J. Biol. Chem., 2007, vol. 282, pp. 13585-13591.
Gentilucci et al., "Chemical Modifications Designed to Improve Peptide Stability: Incorporation of Non-Natural Amino Acids, Pseudo-Peptide Bonds, and Cyclization," Current Pharmaceutical Design, 2010, vol. 16, pp. 3185-3203.
Gupta et al., "Intracellular Delivery of Large Molecules and Small Particles by Cell-Penetrating Proteins and Peptides," Advanced Drug Discovery Reviews, 2004, vol. 57, p. 637-651.
Hikari et al., Bioorganic & Medicinal Chemistry Letters, 2008, vol. 18 (22), pp. 6000-6003.
Kellogg et al., "Disulfide-Linked Antibody—Maytansinoid Conjugates: Optimization of in Vivo Activity by Varying the Steric Hindrance at Carbon Atoms Adjacent to the Disulfide Linkage," Bioconjugate Chemistry, 2011, vol. 22, pp. 717-727.
Kemp and McNamara, "Conformationally Restricted Cyclic Nonapeptides Derived from L-Cysteine and LL-3-Amino-2-Piperidone-6-Carboxylic Acid (LL-Acp), a Potent β-Turn-Inducing Dipeptide Analogue," J. Org. Chem, 1985, vol. 50, pp. 5834-5838.
Nair et al. "Mimicry of Native Peptide Antigens by the Corresponding Retro-Inverso Analogs is Dependent on Their Intrinsic Structure and Interaction Propensities," J Immunol, 2003, vol. 170(3), pp. 1362-1373.
Nestor et al., "The Medicinal Chemistry of Peptides," Curr. Medicinal Chem, 2009, vol. 16, pp. 4399-4418.
Oehlke et al., "Cellular Uptake of an α-Helical Amphipathic Model Peptide With the Potential to Deliver Polar Compounds into the Cell Interiror Non-Endocytically," Biochimica et Biophysica Acta, 1998, vol. 1414, pp. 127-139.
Okazaki et al., "A Rheostat for Immune Responses: the Unique Properties of PD-1 and Their Advantages for Clinical Application," Nat. Immunol., 2013, vol. 14, pp. 1212-1218.
Okuyama et al., "Small-Molecule Mimics of an α-Helix for Efficient Transport of Proteins into Cells," Nature Methods, 2007, vol. 4(2), pp. 153-159.
Robinson et al., Integrative Clinical Genomics of Advanced Prostate Cancer, Cell, 2015, vol. 161, pp. 1215-1228.
Ross et al., "Bispecific T Cell Enager (BiTE) Antibody Constructs Can Mediate Bystander Tumor Cell Killing," PLoS ONE, Aug. 24, 2017, vol. 12(8), pp. 1-24.
Schreiber et al., "Rapid, Electrostatically Assisted Association of Proteins," Nature Struct. Biol., 1996, vol. 3, pp. 427-431.
Timmerman et al., "Rapid and Quantitative Cyclization of Multiple Peptide Loops onto Synthetic Scaffolds for Structural Mimicry of Protein Surfaces," ChemBioChem, 2005, vol. 6, pp. 821-824.
Toogood, "Small Molecule Immuno-oncology Therapeutic Agents," Bioorganic & Medicinal Chemistry Letters, 2018, vol. 28, pp. 319-329.
Tugyi et al., "Partial D-Amino Acid Substitution: Improved Enzymatic Stability and Preserved Ab Recognition of a MUC2 Epitope Peptide," PNAS, 2005, vol. 102(2), pp. 413-418.
Wei et al., "Discovery of Peptidomimetic Antibody-Drug Conjugate Linkers with Enhanced Protease Specificity," J. Med. Chem., 2018, vol. 61, pp. 989-1000.
Wu et al., "Structures of the CXCR4 Chemokine Receptor in Complex with Small Molecule and Cyclic Peptide Antagonists," Science, 2010, vol. 330(6007), pp. 1066-1071.
Xiong et al., "Crystal Structure of the Extracellular Segment of Integrin αVβ3 in Complex with an Arg-Gly-Asp Ligand," Science, 2002, vol. 296 (5565), pp. 151-155.
Zhao et al., "Structural Basis of Specificity of a Peptidyl Urokinase Inhibitor, Upain-1," J Struct Biol, 2007, vol. 160(1), pp. 1-10.
Zou et al., "PD-L1 (B7-H1) and PD-1 Pathway Blockade for Cancer Therapy: Mechanisms, Response Biomarkers, and Combinations," Sci. Transl. Med., 2016, vol. 8, pp. 1-14.

* cited by examiner

---- Isotype
---- Nectin-4

(A)

(B)

(A)

(B)

(A)

(B)

(A)

(B)

(A)

(B)

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: Xaa
<222> LOCATION: (3)..(3)
<223> OTHER INFORMATION: 1Nal: 1-Naphthylalanine
<220> FEATURE:
<221> NAME/KEY: Xaa
<222> LOCATION: (4)..(4)
<223> OTHER INFORMATION: dD: D-aspartic acid
<220> FEATURE:
<221> NAME/KEY: Xaa
<222> LOCATION: (7)..(7)
<223> OTHER INFORMATION: HArg: HomoArginine
<220> FEATURE:
<221> NAME/KEY: Xaa
<222> LOCATION: (13)..(13)
<223> OTHER INFORMATION: HyP: Hydroxyproline

<400> SEQUENCE: 1

Cys Pro Xaa Xaa Cys Met Xaa Asp Trp Ser Thr Pro Xaa Trp Cys
1               5                   10                  15

<210> SEQ ID NO 2
<211> LENGTH: 18
<212> TYPE: PRT
<213> ORGANISM: Artificial Sequence
<220> FEATURE:
```

```
<223> OTHER INFORMATION: synthetic
<220> FEATURE:
<221> NAME/KEY: Xaa
<222> LOCATION: (18)..(18)
<223> OTHER INFORMATION: Sar6-K(Fl): 6 sarcosine (Sar) residues followed
      by a Fluorescein (Fl) labelled lysine (K)

<400> SEQUENCE: 2

Ala Cys Pro Phe Gly Cys His Thr Asp Trp Ser Trp Pro Ile Trp Cys
1               5                   10                  15

Ala Xaa
```

BICYCLIC PEPTIDE LIGANDS SPECIFIC FOR NECTIN-4

SEQUENCE LISTING

The instant application contains a Sequence Listing which has been submitted electronically in ASCII format and is hereby incorporated by reference in its entirety. Said ASCII copy, created on Sep. 5, 2019, is named BIC-C-P2584US_sequence_listing_revised_ST25.txt and is 2,000 bytes in size.

FIELD OF THE INVENTION

The present invention relates to polypeptides which are covalently bound to molecular scaffolds such that two or more peptide loops are subtended between attachment points to the scaffold. In particular, the invention describes peptides which are high affinity binders of Nectin-4. The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder mediated by Nectin-4.

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å$^2$; Wu et al. (2007), Science 330, 1066-71), a cyclic peptide with the Arg-Gly-Asp motif binding to integrin αVb3 (355 Å$^2$) (Xiong et al. (2002), Science 296 (5565), 151-5) or the cyclic peptide inhibitor upain-1 binding to urokinase-type plasminogen activator (603 Å$^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8 (MMP-8), which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example TATA (1,1',1''-(1,3,5-triazinane-1,3,5-triyl) triprop-2-en-1-one, Heinis et al. Angew Chem, Int Ed. 2014; 53:1602-1606).

Phage display-based combinatorial approaches have been developed to generate and screen large libraries of bicyclic peptides to targets of interest (Heinis et al. (2009), Nat Chem Biol 5 (7), 502-7 and WO 2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule scaffold.

SUMMARY OF THE INVENTION

According to a first aspect of the invention, there is provided a peptide ligand specific for Nectin-4 comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold, wherein the peptide ligand comprises the amino acid sequence:

(SEQ ID NO: 1)
$C_i$P[1Nal][dD]$C_{ii}$M[HArg]DWSTP[HyP]WC$_{iii}$;

wherein 1Nal represents 1-naphthylalanine, HArg represents homoarginine, HyP represents hydroxyproline and $C_i$, $C_{ii}$ and $C_{iii}$ represent first, second and third cysteine residues, respectively or a pharmaceutically acceptable salt thereof.

According to a further aspect of the invention, there is provided a drug conjugate comprising a peptide ligand as defined herein conjugated to one or more effector and/or functional groups.

According to a further aspect of the invention, there is provided a pharmaceutical composition comprising a peptide ligand or a drug conjugate as defined herein in combination with one or more pharmaceutically acceptable excipients.

According to a further aspect of the invention, there is provided a peptide ligand or drug conjugate as defined herein for use in preventing, suppressing or treating a disease or disorder mediated by Nectin-4.

BRIEF DESCRIPTION OF THE FIGURES

Where present in the figures, error bars represent standard error of the mean (SEM).

FIGS. 12-16: Gating strategy for Nectin-4 in Bladder cancer (HT1376; FIG. 12), Breast cancer (MDA-MB-468; FIG. 13), Colorectal cancer (HT-29; FIG. 16), respectively.

DETAILED DESCRIPTION OF THE INVENTION

Figure 1:
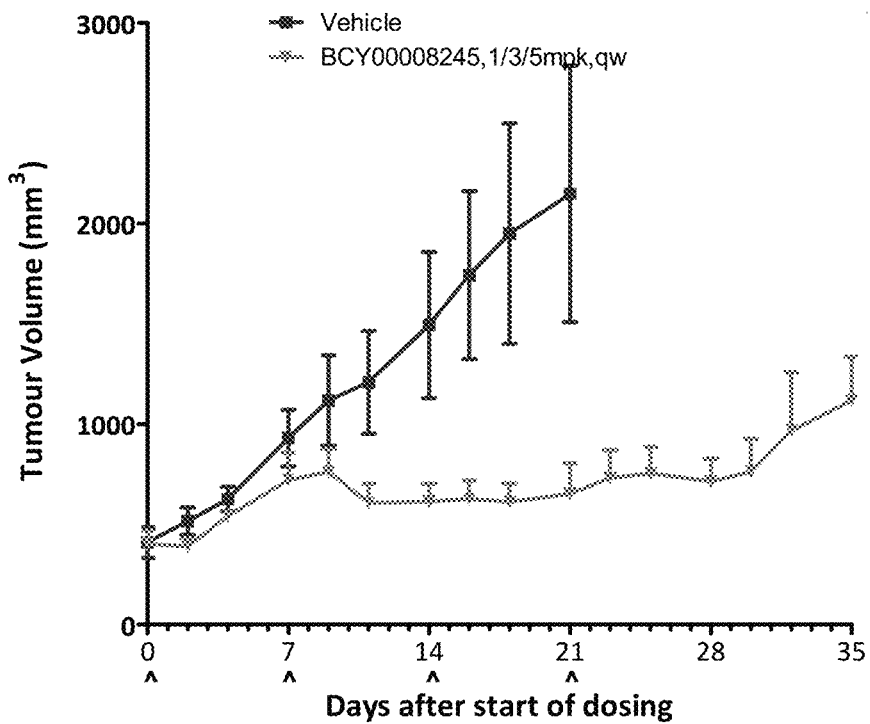
FIGS. 1 and 2: Tumor volume traces after administering BCY8245 to female BALB/c nude mice bearing NCI-H292 xenograft.

In one embodiment, the peptide ligand of $C_iP[1Nal][dD]C_{ii}M[HArg]DWSTP[HyP]WC_{iii}$ (SEQ ID NO: 1) comprises an amino acid sequence selected from:

```
[B-Ala][Sar10]-(SEQ ID NO: 1)(hereinafter
referred to as BCY8234);

Ac-[B-Ala][Sar5]-(SEQ ID NO: 1) (hereinafter
referred to as BCY8122);

Ac-(SEQ ID NO: 1) (hereinafter referred to as
BCY8126);

(SEQ ID NO: 1) (hereinafter referred to as
BCY8116);

Fluorescein-(SEQ ID NO: 1) (hereinafter referred
to as BCY8205);
and

[PYA][B-Ala][Sar10]-(SEQ ID NO: 1) (hereinafter
referred to as BCY8846).
```

In a further embodiment, the peptide ligand of $C_iP[1Nal][dD]C_{ii}M[HArg]DWSTP[HyP]WC_{iii}$ (SEQ ID NO: 1) comprises an amino acid sequence selected from:

```
[B-Ala][Sar10]-(SEQ ID NO: 1) (hereinafter
referred to as BCY8234);

Ac-[B-Ala][Sar5]-(SEQ ID NO: 1) (hereinafter
referred to as BCY8122);

Ac-(SEQ ID NO: 1) (hereinafter referred to as
BCY8126);

(SEQ ID NO: 1) (hereinafter referred to as
BCY8116);
and

Fluorescein-(SEQ ID NO: 1) (hereinafter referred
to as BCY8205).
```

In a yet further embodiment, the peptide ligand of $C_iP[1Nal][dD]C_{ii}M[HArg]DWSTP[HyP]WC_{iii}$ (SEQ ID NO: 1) comprises an amino acid sequence selected from:

```
Ac-[B-Ala][Sar5]-(SEQ ID NO: 1) (hereinafter
referred to as BCY8122);

Ac-(SEQ ID NO: 1) (hereinafter referred to as
BCY8126);
and (SEQ ID NO: 1) (hereinafter referred to as
BCY8116).
```

Data is presented herein in Table 2 which demonstrates that the peptide ligands of this embodiment exhibited excellent levels of binding to human Nectin-4 as evidenced by the SPR binding data.

In a yet further embodiment, the peptide ligand of $C_iP[1Nal][dD]C_{ii}M[HArg]DWSTP[HyP]WC_{iii}$ (SEQ ID NO: 1) comprises an amino acid sequence selected from:

```
Ac-[B-Ala][Sar5]-(SEQ ID NO: 1) (hereinafter
referred to as BCY8122);
and

Ac-(SEQ ID NO: 1) (hereinafter referred to as
BCY8126).
```

Data is presented herein in Table 1 which demonstrates that the peptide ligands of this embodiment exhibited excellent levels of binding to human Nectin-4 as evidenced by the competition binding data binding data.

In a yet further embodiment, the peptide ligand of $C_iP$[1Nal][dD]$C_{ii}$M[HArg]DWSTP[HyP]W$C_{iii}$ (SEQ ID NO: 1) comprises an amino acid sequence selected from:

[B-Ala][Sar10]-(SEQ ID NO: 1) (hereinafter referred to as BCY8234).

Data is presented herein in Table 3 which demonstrates that the peptide ligands of this embodiment when conjugated to a cytotoxic agent exhibited excellent levels (<10 nM) of binding to human Nectin-4 as evidenced by the SPR binding data.

In one embodiment, the molecular scaffold is 1,1',1''-(1,3,5-triazinane-1,3,5-triyl)triprop-2-en-1-one (TATA).

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) $4^{th}$ ed., John Wiley & Sons, Inc.), which are incorporated herein by reference.

Nomenclature
Numbering

When referring to amino acid residue positions within the peptides of the invention, cysteine residues ($C_i$, $C_{ii}$ and $C_{iii}$) are omitted from the numbering as they are invariant, therefore, the numbering of amino acid residues within the peptides of the invention is referred to as below:

(SEQ ID NO: 1)
$C_i$-$P_1$-[Nal]$_2$-[dD]$_3$-$C_{ii}$-$M_4$-[HArg]$_5$-$D_6$-$W_7$-$S_8$-$T_9$-$P_{10}$-[HyP]$_{11}$-$W_{12}$-$C_{iii}$ For the purpose of this description, all bicyclic peptides are assumed to be cyclised with 1,1',1''-(1,3,5-triazinane-1,3,5-triyl)triprop-2-an-1-one (TATA) and yielding a tri-substituted structure. Cyclisation with TATA occurs on $C_i$, $C_{ii}$, and $C_{iii}$.

Molecular Format

N- or C-terminal extensions to the bicycle core sequence are added to the left or right side of the sequence, separated by a hyphen. For example, an N-terminal βAla-Sar10-Ala tail would be denoted as:

βAla-Sar10-A-(SEQ ID NO: X).

Inversed Peptide Sequences

In light of the disclosure in Nair et al (2003) J Immunol 170(3), 1362-1373, it is envisaged that the peptide sequences disclosed herein would also find utility in their retro-inverso form. For example, the sequence is reversed (i.e. N-terminus becomes C-terminus and vice versa) and their stereochemistry is likewise also reversed (i.e. D-amino acids become L-amino acids and vice versa).

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three cysteine residues (referred to herein as $C_i$, $C_{ii}$ and $C_{iii}$), and form at least two loops on the scaffold.

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Bicyclic peptide ligands should ideally demonstrate stability to plasma proteases, epithelial ("membrane-anchored") proteases, gastric and intestinal proteases, lung surface proteases, intracellular proteases and the like. Protease stability should be maintained between different species such that a bicycle lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes;

An optimal plasma half-life in the circulation. Depending upon the clinical indication and treatment regimen, it may be required to develop a bicyclic peptide for short exposure in an acute illness management setting, or develop a bicyclic peptide with enhanced retention in the circulation, and is therefore optimal for the management of more chronic disease states. Other factors driving the desirable plasma half-life are requirements of sustained exposure for maximal therapeutic efficiency versus the accompanying toxicology due to sustained exposure of the agent; and Selectivity. Certain peptide ligands of the invention demonstrate good selectivity over other nectins.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use,* P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO−), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the peptides of the invention contain an amine function, these may form quaternary ammonium salts, for example by reaction with an alkylating agent according to methods well known to the skilled person. Such quaternary ammonium compounds are within the scope of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal cysteine group (the group referred to herein as $C_i$) is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal cysteine group (the group referred to herein as $C_{iii}$) is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102(2), 413-418).

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labeled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^{2}H$ (D) and $^{3}H$ (T), carbon, such as $^{11}C$, $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, sulfur, such as $^{35}S$, copper, such as $^{64}Cu$, gallium, such as $^{67}Ga$ or $^{68}Ga$, yttrium, such as $^{90}Y$ and lutetium, such as $^{177}Lu$, and Bismuth, such as $^{213}Bi$.

Certain isotopically-labelled peptide ligands of the invention, for example, those incorporating a radioactive isotope, are useful in drug and/or substrate tissue distribution studies, and to clinically assess the presence and/or absence of the Nectin-4 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}H$ (T), and carbon-14, i.e. $^{14}C$, are particularly useful for this purpose in view of their ease of incorporation and ready means of detection.

Substitution with heavier isotopes such as deuterium, i.e. $^{2}H$ (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labeled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Molecular Scaffold

In one embodiment, the molecular scaffold comprises a non-aromatic molecular scaffold. References herein to "non-aromatic molecular scaffold" refer to any molecular scaffold as defined herein which does not contain an aromatic (i.e. unsaturated) carbocyclic or heterocyclic ring system.

Suitable examples of non-aromatic molecular scaffolds are described in Heinis et al (2014) *Angewandte Chemie, International Edition* 53(6) 1602-1606.

As noted in the foregoing documents, the molecular scaffold may be a small molecule, such as a small organic molecule.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

An example of an αβ unsaturated carbonyl containing compound is 1,1',1"-(1,3,5-triazinane-1,3,5-triyl)triprop-2-en-1-one (TATA) (Angewandte Chemie, International Edition (2014), 53(6), 1602-1606).

Effector and Functional Groups

According to a further aspect of the invention, there is provided a drug conjugate comprising a peptide ligand as defined herein conjugated to one or more effector and/or functional groups.

Effector and/or functional groups can be attached, for example, to the N and/or C termini of the polypeptide, to an amino acid within the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of *Drosophila* (Antennapedia), e.g. as described in Chen and Harrison, Biochemical Society Transactions (2007) Volume 35, part 4, p 821; Gupta et al. in Advanced Drug Discovery Reviews (2004) Volume 57 9637. Examples of short peptides which have been shown to be efficient at translocation through plasma membranes include the 16 amino acid penetratin peptide from *Drosophila* Antennapedia protein (Derossi et al (1994) J Biol. Chem. Volume 269 p 10444), the 18 amino acid 'model amphipathic peptide' (Oehlke et al (1998) Biochim Biophys Acts Volume 1414 p 127) and arginine rich regions of the HIV TAT protein. Non peptidic approaches include the use of small molecule mimics or SMOCs that can be easily attached to biomolecules (Okuyama et al (2007) Nature Methods Volume 4 p 153). Other chemical strategies to add guanidinium groups to molecules also enhance cell penetration (Elson-Scwab et al (2007) J Biol Chem Volume 282 p 13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half-life in the range 12 to 60 hours. In a further embodiment, it will have a tβ half-life of a day or more. In a further embodiment still, it will be in the range 12 to 26 hours.

In one particular embodiment of the invention, the functional group is selected from a metal chelator, which is suitable for complexing metal radioisotopes of medicinal relevance.

Possible effector groups also include enzymes, for instance such as carboxypeptidase G2 for use in enzyme/prodrug therapy, where the peptide ligand replaces antibodies in ADEPT.

In one particular embodiment of the invention, the functional group is selected from a drug, such as a cytotoxic agent for cancer therapy. Suitable examples include: alkylating agents such as cisplatin and carboplatin, as well as oxaliplatin, mechlorethamine, cyclophosphamide, chlorambucil, ifosfamide; Anti-metabolites including purine analogs azathioprine and mercaptopurine or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include antitumour antibiotics which include the immunosuppressant dactinomycin (which is used in kidney transplantations), doxorubicin, epirubicin, bleomycin, calicheamycins, and others.

In one further particular embodiment of the invention, the cytotoxic agent is selected from maytansinoids (such as DM1) or monomethyl auristatins (such as MMAE).

DM1 is a cytotoxic agent which is a thiol-containing derivative of maytansine and has the following structure:

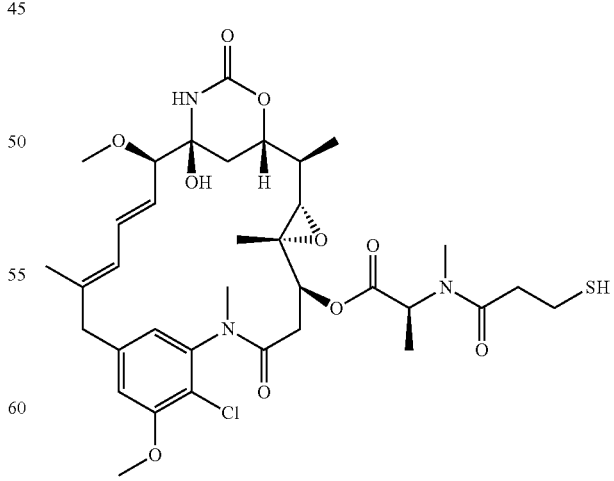

Data is presented herein in Table 3 which demonstrates the effects of a peptide ligand conjugated to a toxin containing DM1.

Monomethyl auristatin E (MMAE) is a synthetic antineoplastic agent and has the following structure:

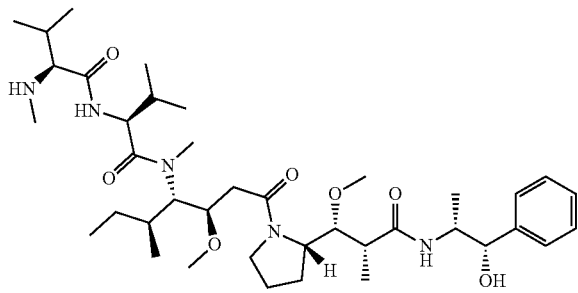 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

Data is presented herein in Table 3 which demonstrates the effects of peptide ligands conjugated to a toxin containing MMAE.

In one yet further particular embodiment of the invention, the cytotoxic agent is selected from monomethyl auristatin E (MMAE).

In one embodiment, the cytotoxic agent is linked to the bicyclic peptide by a cleavable bond, such as a disulphide bond or a protease sensitive bond. In a further embodiment, the groups adjacent to the disulphide bond are modified to control the hindrance of the disulphide bond, and by this the rate of cleavage and concomitant release of cytotoxic agent.

Published work established the potential for modifying the susceptibility of the disulphide bond to reduction by introducing steric hindrance on either side of the disulphide bond (Kellogg et al (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on either the targeting entity (here, the bicyclic peptide) or toxin side of the molecular construct.

In one embodiment, the cytotoxic agent and linker is selected from any combinations of those described in WO 2016/067035 (the cytotoxic agents and linkers thereof are herein incorporated by reference).

In one embodiment, the linker between said cytotoxic agent and said bicyclic peptide comprises one or more amino acid residues. Examples of suitable amino acid residues as suitable linkers include Ala, Cit, Lys, Trp and Val.

In one embodiment, the cytotoxic agent is selected from MMAE and said drug conjugate additionally comprises a linker selected from: -PABC-Cit-Val-Glutaryl- or -PABC-cyclobutyl-Ala-Cit-βAla-, wherein PABC represents p-aminobenzylcarbamate. Full details of the cyclobutyl containing linker may be found in Wei et al (2018) J. Med. Chem. 61, 989-1000. In a further embodiment, the cytotoxic agent is selected from MMAE and the linker is -PABC-Cit-Val-Glutaryl-.

In an alternative embodiment, the cytotoxic agent is DM1 and said drug conjugate additionally comprises a linker which is -SPDB-($SO_3H$)—, wherein SPDB represents N-succinimidyl 3-(2-pyridyldithio)propionate.

In an alternative embodiment, the cytotoxic agent is MMAE, the bicyclic peptide is selected from BCY8234 as defined herein and the linker is selected from -PABC-Cit-Val-Glutaryl-. This BDC is known herein as BCY8245 and is

BCY8245

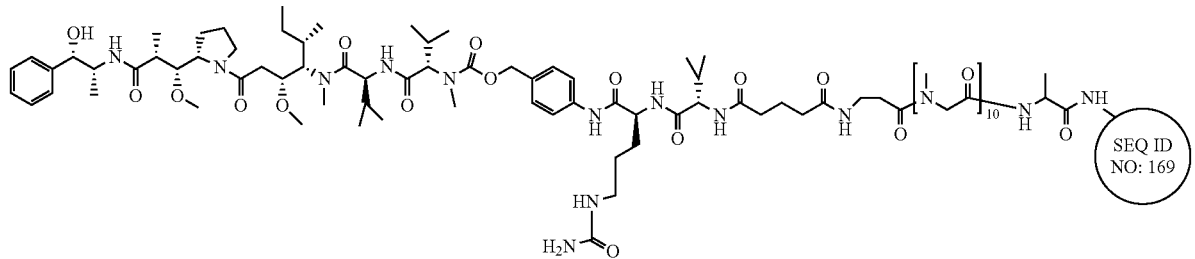

represented in a more detailed manner as:

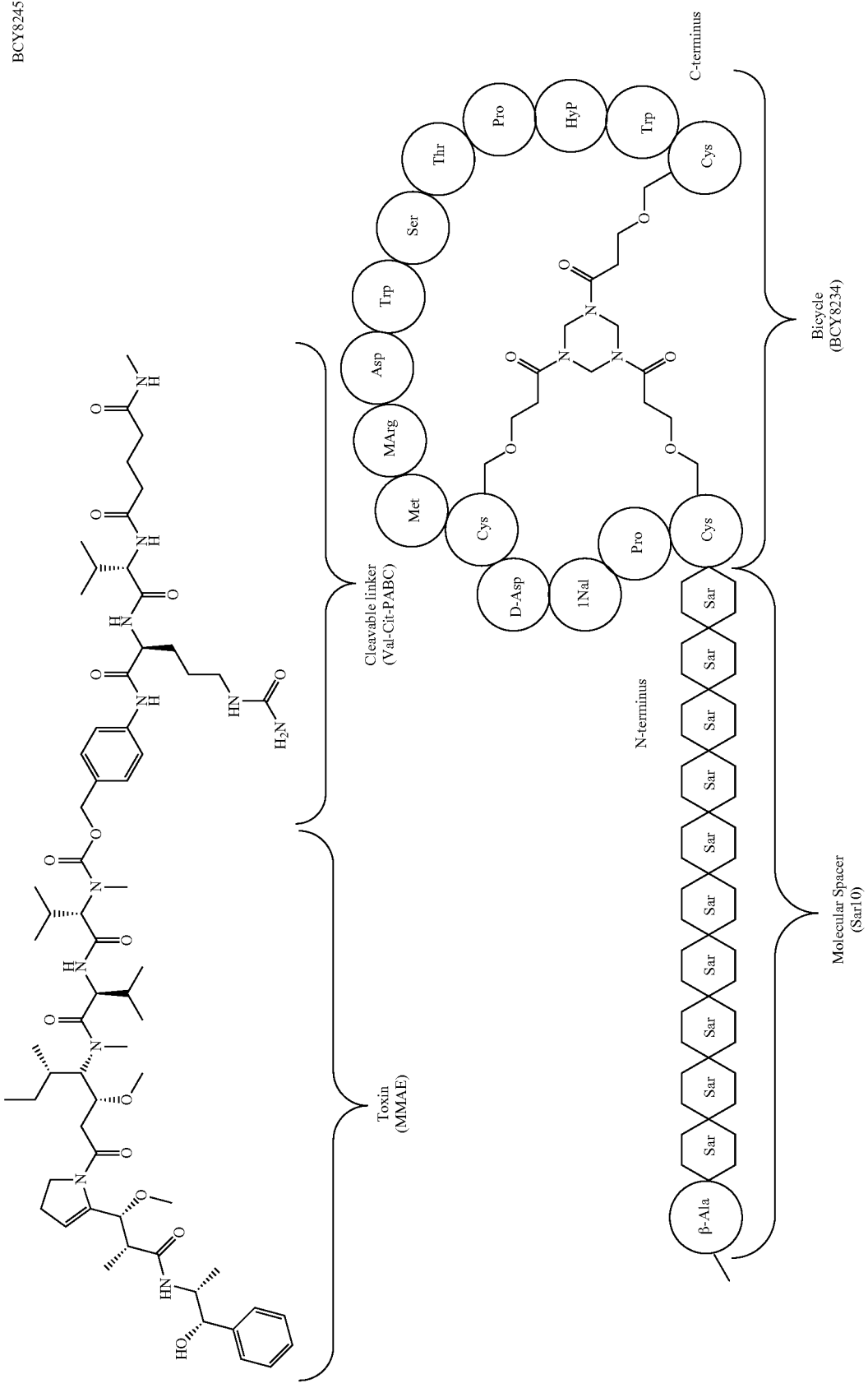

Data is presented herein which demonstrates excellent binding to human Nectin-4 for BCY8245 in the SPR binding assay as shown in Table 3. This BDC also demonstrated good anti-tumour activity in the Non-Small Cell Lung Cancer model as shown in Example 1, the bladder cancer model as shown in Example 2, the pancreatic cancer model as shown in Example 3 and the breast cancer model as shown in Example 4.

In an alternative embodiment, the cytotoxic agent is MMAE, the bicyclic peptide is selected from BCY8234 as defined herein and the linker is selected from -PABC-cyclobutyl-(B-Ala)-. This BDC is known herein as BCY8549. Data is presented herein which demonstrates excellent binding to human Nectin-4 for BCY8549 in the SPR binding assay as shown in Table 3.

In a further embodiment, the bicyclic drug conjugate is selected from BCY8245 or BCY8549. In a yet further embodiment, the bicyclic drug conjugate is BCY8245. The drug conjugate BCY8245 demonstrated superior dose dependent anti-tumour activity as demonstrated in the data described herein.

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al. Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TATA) could be added during the chemical synthesis of the first peptide so as to react with the three cysteine groups; a further cysteine or thiol could then be appended to the N- or C-terminus of the first peptide, so that this cysteine or thiol only reacted with a free cysteine or thiol of the second peptide, forming a disulfide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand or a drug conjugate as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Co-Administration with One or More Other Therapeutic Agent

Depending upon the particular condition, or disease, to be treated, additional therapeutic agents that are normally administered to treat that condition, may also be present in the compositions of this invention. Thus, in one embodiment, the pharmaceutical composition additionally comprises one or more therapeutic agents. As used herein, additional therapeutic agents that are normally administered to treat a particular disease, or condition, are known as "appropriate for the disease, or condition, being treated."

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

One or more other therapeutic agent may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 19, 20, 21, 22, 23, or 24 hours from one another. In some embodiments, one or more other therapeutic agent and a compound or composition of the invention are administered as a multiple dosage regimen within greater than 24 hours apart.

As used herein, the term "combination," "combined," and related terms refers to the simultaneous or sequential administration of therapeutic agents in accordance with this invention. For example, a compound of the present invention may be administered with one or more other therapeutic agent simultaneously or sequentially in separate unit dosage forms or together in a single unit dosage form. Accordingly, the present invention provides a single unit dosage form comprising a compound of the current invention, one or more other therapeutic agent, and a pharmaceutically acceptable carrier, adjuvant, or vehicle.

The amount of a compound of the invention and one or more other therapeutic agent (in those compositions which comprise an additional therapeutic agent as described above) that may be combined with the carrier materials to produce a single dosage form will vary depending upon the host treated and the particular mode of administration. Preferably, a composition of the invention should be formulated so that a dosage of between 0.01-100 mg/kg body weight/day of a compound of the invention can be administered.

In those compositions which comprise one or more other therapeutic agent, the one or more other therapeutic agent and a compound of the invention may act synergistically. Therefore, the amount of the one or more other therapeutic agent in such compositions may be less than that required in a monotherapy utilizing only that therapeutic agent. In such compositions a dosage of between 0.01-1,000 µg/kg body weight/day of the one or more other therapeutic agent can be administered.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount of an FDA approved therapeutic agent provided for dosing as per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplary Other Therapeutic Agents

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (Zolinza®, Merck); romidepsin (Istodax®, Celgene); panobinostat (Farydak®, Novartis); belinostat (Beleodaq®, Spectrum Pharmaceuticals); entinostat (SNDX-275, Syndax Pharmaceuticals) (NCT00866333); and chidamide (Epidaza®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (Ibrance®, Pfizer); ribociclib (Kisqali®, Novartis); abemaciclib (Ly2835219, Eli Lilly); and trilaciclib (G1T28, G1 Therapeutics).

In some embodiments, one or more other therapeutic agent is a phosphatidylinositol 3 kinase (PI3K) inhibitor. In some embodiments, a PI3K inhibitor is selected from idelalisib (Zydelig®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, one or more other therapeutic agent is a platinum-based therapeutic, also referred to as platins. Platins cause cross-linking of DNA, such that they inhibit DNA repair and/or DNA synthesis, mostly in rapidly reproducing cells, such as cancer cells. In some embodiments, a platinum-based therapeutic is selected from cisplatin (Platinol®, Bristol-Myers Squibb); carboplatin (Paraplatin®, Bristol-Myers Squibb; also, Teva; Pfizer); oxaliplatin (Eloxitin® Sanofi-Aventis); nedaplatin (Aqupla®, Shionogi), picoplatin (Poniard Pharmaceuticals); and satraplatin (JM-216, Agennix).

In some embodiments, one or more other therapeutic agent is a taxane compound, which causes disruption of microtubules, which are essential for cell division. In some embodiments, a taxane compound is selected from paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), cabazitaxel (Jevtana®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, one or more other therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include: tivozanib (Aveo Pharmaceuticals); vatalanib (Bayer/Novartis); lucitanib (Clovis Oncology); dovitinib (TKI258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547,632 (Pfizer); foretinib (Exelexis, GlaxoSmithKline); quizartinib (Daiichi Sankyo) and motesanib (Amgen/Takeda).

In some embodiments, one or more other therapeutic agent is an mTOR inhibitor, which inhibits cell proliferation, angiogenesis and glucose uptake. In some embodiments, an mTOR inhibitor is everolimus (Afinitor®, Novartis); temsirolimus (Torisel®, Pfizer); and sirolimus (Rapamune®, Pfizer).

In some embodiments, one or more other therapeutic agent is a proteasome inhibitor. Approved proteasome inhibitors useful in the present invention include bortezomib (Velcade®, Takeda); carfilzomib (Kyprolis®, Amgen); and ixazomib (Ninlaro®, Takeda).

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include: cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

In some embodiments, one or more other therapeutic agent is an aromatase inhibitor. In some embodiments, an aromatase inhibitor is selected from: exemestane (Aromasin®, Pfizer); anastazole (Arimidex®, AstraZeneca) and letrozole (Femara®, Novartis).

In some embodiments, one or more other therapeutic agent is an antagonist of the hedgehog pathway. Approved hedgehog pathway inhibitors which may be used in the present invention include: sonidegib (Odomzo®, Sun Pharmaceuticals); and vismodegib (Erivedge®, Genentech), both for treatment of basal cell carcinoma.

In some embodiments, one or more other therapeutic agent is a folic acid inhibitor. Approved folic acid inhibitors useful in the present invention include pemetrexed (Alimta®, Eli Lilly).

In some embodiments, one or more other therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, one or more other therapeutic agent is an isocitrate dehydrogenase (IDH) inhibitor. IDH inhibitors being studied which may be used in the present invention include: AG 120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include: AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include: rituximab (Rituxan®, Genentech/Biogenldec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, one or more other therapeutic agent is a topoisomerase inhibitor. Approved topoisomerase inhibitors useful in the present invention include: irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, one or more other therapeutic agent is an inhibitor of anti-apoptotic proteins, such as BCL-2. Approved anti-apoptotics which may be used in the present invention include: venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

In some embodiments, one or more other therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, one or more other therapeutic agent is an inhibitor of interaction between the two primary p53 suppression proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFß). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFß trap compound (NCT02699515); and (NCT02517398). M7824 is comprised of a fully human IgG1 antibody against PD-L1 fused to the extracellular domain of human TGF-beta receptor II, which functions as a TGFß "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by 5 multiple tumor types associated with cancer cells' ability to metastasize.

In some embodiments, one or more other therapeutic agent is an antiproliferative compound. Such antiproliferative compounds include, but are not limited to: aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZd$_6$244 from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol. Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to: taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cisplatin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as: a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/ pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; Ilmofosine; RO 318220 and RO 320432; GO 6976; Isis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases ($EGFR_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and p) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to $PI3K\alpha$, $PI3K\gamma$, $PI3K\delta$, $PI3K\beta$, PI3K-C2$\alpha$, PI3K-C2$\beta$, PI3K-C2$\gamma$, Vps34, p110-$\alpha$, p110-$\beta$, p110-$\gamma$, p110-$\delta$, p85-$\alpha$, p85-$\beta$, p55-$\gamma$, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO 2008/118802), navitoclax (and analogs thereof, see U.S. Pat. No. 7,390,799), NH-1 (Shenayng Pharmaceutical University), obatoclax (and analogs thereof, see WO 2004/106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO 2008/039218 and WO 2011/090760, the entirety of which are incorporated herein by reference.

Further examples of SYK inhibitory compounds, and conditions treatable by such compounds in combination with compounds of this invention can be found in WO 2003/063794, WO 2005/007623, and WO 2006/078846, the entirety of which are incorporated herein by reference.

Further examples of PI3K inhibitory compounds, and conditions treatable by such compounds in combination with compounds of this invention can be found in WO 2004/019973, WO 2004/089925, WO 2007/016176, U.S. Pat. No. 8,138,347, WO 2002/088112, WO 2007/084786, WO 2007/129161, WO 2006/122806, WO 2005/113554, and WO 2007/044729 the entirety of which are incorporated herein by reference.

Further examples of JAK inhibitory compounds, and conditions treatable by such compounds in combination with compounds of this invention can be found in WO 2009/114512, WO 2008/109943, WO 2007/053452, WO 2000/142246, and WO 2007/070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib, or a 5-alkyl-2-arylaminophenylacetic acid, such as 5-methyl-2-(2'-chloro-6'-fluoroanilino)phenyl acetic acid and lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibody fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as: 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; $Zd_6474$; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to: plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY and NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonist of activating receptors on NK cells. In some embodiments, an immuno-oncology agent is an antagonist of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO 2011/70024, WO 2011/107553, WO 2011/131407, WO 2013/87699, WO 2013/119716, WO 2013/132044) or FPA-008 (WO 2011/140249; WO 2013/169264; WO 2014/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YER-VOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO 2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO 2010/077634), durvalumab (MEDI4736), BMS-936559 (WO 2007/005874), and MSB0010718C (WO 2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO 2010/19570, WO 2014/08218), or IMP-731 or IMP-321 (WO 2008/132601, WO 2009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO 2012/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO 2006/105021, WO 2009/009116), or MK-4166 (WO 2011/028683).

In some embodiments, an immuno-oncology agent is an indoleamine (2,3)-dioxygenase (IDO) antagonist. In some embodiments, an IDO antagonist is selected from: epacadostat (INCB024360, Incyte); indoximod (NLG-8189, New-Link Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Kyn Therapeutics); and NLG-919 (WO 2009/73620, WO 2009/1156652, WO 2011/56652, WO 2012/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO 2006/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO 2011/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with renal clear cell carcinoma (RCC) who had experienced disease progression during or after prior antiangiogenic therapy.

In some embodiments, the immunomodulatory therapeutic specifically induces apoptosis of tumor cells. Approved immunomodulatory therapeutics which may be used in the present invention include: pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from: sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from: JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include: urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; and MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those described in Jerry L. Adams et al., "Big opportunities for small molecules in immuno-oncology," Cancer Therapy 2015, Vol. 14, pages 603-622, the content of which is incorporated herein by reference in its entirety. In some embodiment, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams et al. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDLI, PDL2, PDI, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDLI, PDL2, PDI, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-LI monoclonal Antibody (Anti-B7-HI; MEDI4736), MK-3475 (PD-1 blocker), Nivolumab (anti-PDI antibody), CT-011 (anti-PDI antibody), BY55 monoclonal antibody, AMP224 (anti-PDLI antibody), BMS-936559 (anti-PDLI antibody), MPLDL3280A (anti-PDLI antibody), MSB0010718C (anti-PDLI antibody), and ipilimumab (anti-CTLA-4 checkpoint inhibitor). Checkpoint protein ligands include, but are not limited to PD-LI, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from: nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is: REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in: melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include: PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include: utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include: varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include: TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include: MEDI-570 (Medimmune), an agonistic anti-ICOS antibody, in lymphomas (NCT02520791); GSK3359609 (Merck), an agonistic anti-ICOS antibody, in Phase 1 (NCT02723955); and JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include: lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include: ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include: MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known astransmembrane protein 173, or TMEM173). Agonists of STING that are being studied in clinical trials include: MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include: pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

Therapeutic Uses

The bicyclic peptides of the invention have specific utility as Nectin-4 binding agents.

Nectin-4 is a surface molecule that belongs to the nectin family of proteins, which comprises 4 members. Nectins are cell adhesion molecules that play a key role in various biological processes such as polarity, proliferation, differentiation and migration, for epithelial, endothelial, immune and neuronal cells, during development and adult life. They are involved in several pathological processes in humans. They are the main receptors for poliovirus, herpes simplex virus and measles virus. Mutations in the genes encoding Nectin-1 (PVRL1) or Nectin-4 (PVRL4) cause ectodermal dysplasia syndromes associated with other abnormalities. Nectin-4 is expressed during foetal development. In adult tissues its expression is more restricted than that of other members of the family. Nectin-4 is a tumour-associated antigen in 50%, 49% and 86% of breast, ovarian and lung carcinomas, respectively, mostly on tumours of bad prognosis. Its expression is not detected in the corresponding normal tissues. In breast tumours, Nectin-4 is expressed mainly in triple-negative and ERBB2+ carcinomas. In the serum of patients with these cancers, the detection of soluble forms of Nectin-4 is associated with a poor prognosis. Levels of serum Nectin-4 increase during metastatic progression and decrease after treatment. These results suggest that Nectin-4 could be a reliable target for the treatment of cancer. Accordingly, several anti-Nectin-4 antibodies have been described in the prior art. In particular, Enfortumab Vedotin (ASG-22ME) is an antibody-drug conjugate (ADC) targeting Nectin-4 and is currently clinically investigated for the treatment of patients suffering from solid tumours.

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

According to a further aspect of the invention, there is provided a peptide ligand or a drug conjugate as defined herein, for use in preventing, suppressing or treating a disease or disorder mediated by Nectin-4.

According to a further aspect of the invention, there is provided a method of preventing, suppressing or treating a disease or disorder mediated by Nectin-4, which comprises administering to a patient in need thereof an effector group and drug conjugate of the peptide ligand as defined herein.

In one embodiment, the Nectin-4 is mammalian Nectin-4. In a further embodiment, the mammalian Nectin-4 is human Nectin-4.

In one embodiment, the disease or disorder mediated by Nectin-4 is selected from viral infections, ectodermal dysplasia syndromes and other abnormalities, breast, ovarian and lung carcinomas, metastatic progression, and solid tumours.

In a further embodiment, the disease or disorder mediated by Nectin-4 is selected from cancer.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In a further embodiment, the cancer is selected from a hematopoietic malignancy such as selected from: non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML).

In a yet further embodiment, the cancer is selected from lung cancer (e.g. non-small cell lung cancer), bladder cancer, pancreatic cancer and breast cancer. Data is presented herein in Examples 1 to 5 which demonstrates that selected bicyclic drug conjugates of the invention exhibited anti-tumour activity in these cancer models.

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

Furthermore, data is presented herein which demonstrates an association between copy number variation (CNV) and gene expression for Nectin-4 from multiple tumor types. Thus, according to a further aspect of the invention, there is provided a method of preventing, suppressing or treating cancer, which comprises administering to a patient in need thereof an effector group and drug conjugate of the peptide ligand as defined herein, wherein said patient is identified as having an increased copy number variation (CNV) of Nectin-4.

In one embodiment, the cancer is selected from those identified herein as having increased CNV of Nectin-4. In a further embodiment, the cancer is selected from those identified herein as having increased CNV of Nectin-4, namely: breast, uterine, bladder, lung adenocarcinoma, lung squamous, cervical, head and neck, pancreatic, thyroid, colorectal, thymoma, sarcoma, renal clear cell carcinoma (RCC), prostate and stomach.

The invention is further described below with reference to the following examples.

EXAMPLES

Abbreviations 1,2,4-TriAz 3-(1,2,4-Triazol-1-yl)-alanine
1Nal 1-Naphthylalanine
2FuAla 2-Furylalanine
2MePhe 2-Methyl-Phenylalanine
2Nal 2-Naphthylalanine
2Pal 2-Pyridylalanine
3,3-DPA 3,3-Diphenylalanine
3MePhe 3-Methyl-Phenylalanine
3Pal 3-Pyridylalanine
4,4-BPA 4,4-Biphenylalanine
4,4-DFP 4,4-Difluoroproline
4MePhe 4-Methyl-Phenylalanine
4Pal 4-Pyridylalanine
4ThiAz Beta-(4-Thiazolyl)-Alanine
5FTrp 5-Fluoro-L-tryptophan
Agb 2-Amino-4-guanidinobutyric acid
Aib Aminoisobutyric acid
AzaTrp Azatryptophan
Aze Azetidine
C5A Cyclopentyl glycine
Cha 3-Cyclohexyl-alanine
Cpa Cyclopropylalanine
Cya Cysteic acid
DOPA 3,4-Dihydroxy-phenylalanine
HArg HomoArginine
HGln HomoGlutamine
Hleu HomeLeucine
Hphe HomoPhenylalanine
Hse(me) Homoserine(Me)
HSer HomoSerine
HyP Hydroxyproline
Lys(Ac) Lysine(Acetyl)
Met(O2) Methionine sulfone
Nle Norleucine
Oic Octahydroindolecarboxylic acid
Oxa Oxazolidine-4-carboxylic acid
pCoPhe para-Carboxy-Phenylalanine
PheOPhe 4-Phenoxy-phenylalanine
Phg Phenylglycine
Pip Pipecolic acid
Pro(4NH) 4-Amino-Proline
tBuAla t-Butyl-Alanine
TetraZ Tetrazole Alanine
Thi Thienyl-alanine
THP(O) Tetrahydropyran-4-propanoic acid
THP(SO2) Dioxo-4-tetrahydrothiopyranylacetic acid
Trp(Me) Methyl Trptophan Materials and Methods Peptide Synthesis Peptide synthesis was based on Fmoc chemistry, using a Symphony peptide synthesiser manufactured by Peptide Instruments and a Syro II synthesiser by MultiSynTech. Standard Fmoc-amino acids were employed (Sigma, Merck), with appropriate side chain protecting groups: where applicable standard coupling conditions were used in each case, followed by deprotection using standard methodology.

Alternatively, peptides were purified using HPLC and following isolation they were modified with 1,3,5-Triacryloylhexahydro-1,3,5-triazine (TATA, Sigma). For this, linear peptide was diluted with 50:50 MeCN:$H_2O$ up to ~35 mL, ~500 μL of 100 mM TATA in acetonitrile was added, and the reaction was initiated with 5 mL of 1 M $NH_4HCO_3$ in $H_2O$. The reaction was allowed to proceed for ~30-60 min at RT, and lyophilised once the reaction had completed (judged by MALDI). Once completed, 1 ml of 1M L-cysteine hydrochloride monohydrate (Sigma) in $H_2O$ was added to the reaction for ~60 min at RT to quench any excess TATA. Following lyophilisation, the modified peptide was purified as above, while replacing the Luna C8 with a Gemini C18 column (Phenomenex), and changing the acid to 0.1% trifluoroacetic acid. Pure fractions containing the correct TATA-modified material were pooled, lyophilised and kept at −20° C. for storage.

All amino acids, unless noted otherwise, were used in the L-configurations.

In some cases peptides are converted to activated disulfides prior to coupling with the free thiol group of a toxin using the following method; a solution of 4-methyl(succinimidyl 4-(2-pyridylthio)pentanoate) (100 mM) in dry DMSO (1.25 mol equiv) was added to a solution of peptide (20 mM) in dry DMSO (1 mol equiv). The reaction was well mixed and DIPEA (20 mol equiv) was added. The reaction was monitored by LC/MS until complete.

Preparation of Bicyclic Peptide Drug Conjugates

Preparation of BCY8549

Separation Condition: A phase: 0.075% TFA in $H_2O$, B phase: MeCN

Separation method: 18-48-55 min, RT=53.5 min

Separation column: Luna 200*25 mm 10 μm, C18, 110 A and Gemin150*30 mm, C18, 5 μm, 110 A, connection, 50° C.

Dissolve method: DMF

Separation purity: 95%

BCY8234 was synthesized by solid phase synthesis.

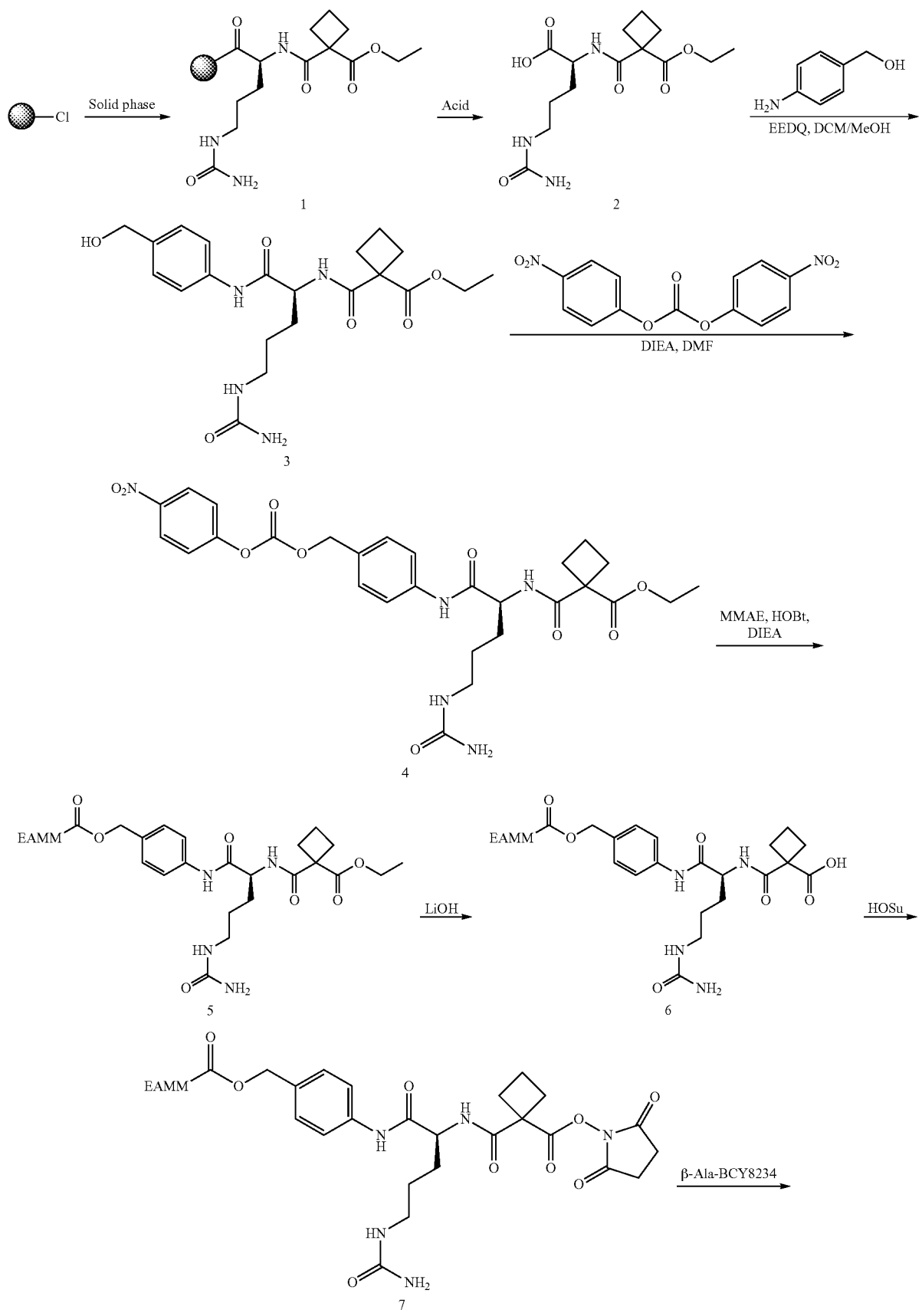

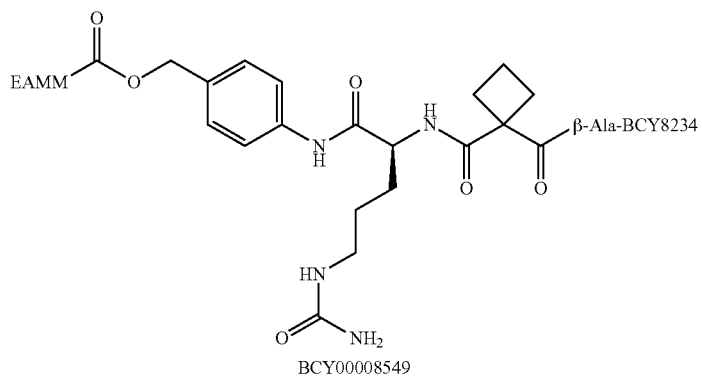

BCY00008549

Preparation of Compound 2

The peptide was synthesized using standard Fmoc chemistry.
1) Add DCM to the vessel containing CTC Resin (5 mmol, 4.3 g, 1.17 mmol/g) and Fmoc-Cit—OH (2.0 g, 5 mmol, 1.0 eq) with $N_2$ bubbling.
2) Add DIEA (4.0 eq) dropwise and mix for 2 hours.
3) Add MeOH (5 mL) and mix for 30 min.
4) Drain and wash with DMF for 5 times.
5) Add 20% piperidine/DMF and react on 30 min.
6) Drain and wash with DMF for 5 times.
7) Add Fmoc-amino acid solution and mix 30 seconds, then add activation buffer, $N_2$ bubbling for about 1 hour.
8) Repeat above step 4 to 7 for the coupling of following amino acids.
Note:

| # | Materials | Coupling reagents |
|---|-----------|-------------------|
| 1 | Fmoc-Cit-OH (1.0 eq) | DIEA (4.0 eq) |
| 2 | 1-ethoxycarbonylcyclobutanecarboxylic acid (3.0 eq) | HATU (2.85 eq) and DIEA (6.0 eq) |

20% piperidine in DMF was used for Fmoc deprotection for 30 min. The coupling reaction was monitored by ninhydrin test, and the resin was washed with DMF for 5 times.

Peptide Cleavage and Purification:
1) Add cleavage buffer (20% TFIP/80% DCM) to the flask containing the side chain protected peptide at room temperature and stir for 1 hour twice.
2) Filter and collect the filtrate.
3) Concentrate to remove the solvent.
4) The crude peptide was lyophilized to give the final product (1.4 g, 85.0% yield).

Preparation of Compound 3

To a solution of compound 2 (1.65 g, 5.01 mmol, 1.0 eq) in DCM (30 mL) and MeOH (15 mL) was added EEDQ (2.48 g, 10.02 mmol, 2.0 eq) and (4-aminophenyl)methanol (740.37 mg, 6.01 mmol, 1.2 eq). The mixture was stirred at 15° C. for 16 hr. LC-MS showed compound 2 was consumed completely and one main peak with desired m/z was detected. TLC indicated compound 2 was consumed completely and many new spots formed. The reaction mixture was concentrated under reduced pressure to remove solvent to give a residue. The residue was purified by flash silica gel chromatography (ISCO®; 80 SepaFlash® Silica Flash Column, Eluent of 0~15 DCM/MeOH gradient @ 60 mL/min). Compound 3 (1.3 g, 2.99 mmol, 59.72% yield) was obtained as a yellow solid.

Preparation of Compound 4

To a solution of compound 3 (1.3 g, 2.99 mmol, 1.0 eq) in DMF (10 mL) was added DIEA (2.32 g, 17.95 mmol, 3.13 mL, 6.0 eq) and bis(4-nitrophenyl) carbonate (3.64 g, 11.97 mmol, 4.0 eq). The mixture was stirred at 15° C. for 1 hr. LC-MS showed compound 3 was consumed completely and one main peak with desired m/z was detected. The residue was purified by prep-HPLC (neutral condition). Compound 4 (1.0 g, 1.67 mmol, 55.74% yield) was obtained as a yellow solid.

Preparation of Compound 5

To a solution of compound 5 (250.53 mg, 417.84 µmol, 1.5 eq) in DMF (5 mL) was added HOBt (56.46 mg, 417.84 µmol, 1.5 eq) and DIEA (108.01 mg, 835.68 µmol, 145.56 µL, 3.0 eq), MMAE (0.200 g, 278.56 µmol, 1.0 eq). The mixture was stirred at 35° C. for 12 hr. LC-MS showed MMAE was consumed completely and one main peak with desired m/z was detected. The reaction was directly purified by prep-HPLC (neutral condition). Compound 5 (0.180 g, 152.74 µmol, 54.83% yield) was obtained as a yellow solid.

Preparation of Compound 6

To a solution of compound 5 (0.170 g, 144.26 µmol, 1.0 eq) in THF (5 mL) and $H_2O$ (5 mL) was added $LiOH·H_2O$ (12.11 mg, 288.51 µmol, 2.0 eq). The mixture was stirred at 15° C. for 1 hr. LC-MS showed compound 5 was consumed completely and one main peak with desired m/z was detected. Adjusted PH=7 used by AcOH and THF was removed under reduced pressure to give a residue. The residue was purified by prep-HPLC (neutral condition). Compound 6 (0.185 g, crude) was obtained as a yellow solid.

Preparation of BCY8549

To a solution of compound 6 (0.100 g, 86.93 µmol, 1.0 eq) in DMA (4 mL) was added HOSu (10.00 mg, 86.93 µmol, 1.0 eq) and EDCI (16.66 mg, 86.93 µmol, 1.0 eq). After the NHS ester was formed, β-Ala-BCY8234 (525.98 mg, 173.85 µmol, 2.0 eq) and DIEA (33.70 mg, 260.78 µmol, 45.42 μL, 3.0 eq). The mixture was stirred at 15° C. for 4 hr. LC-MS showed compound 6 was consumed completely and one main peak with desired m/z was detected. The reaction was directly purified by prep-HPLC (TFA condition). Compound BCY8549 (0.0528 g, 12.15 μmol, 13.98% yield, 95.70% purity) was obtained as a white solid. Retenton time=11.48 min. Mass found=1386.4 (M/3+H)

Preparation of BCY8245

Separation Condition: A phase: 0.075% TFA in $H_2O$, B phase: MeCN

Separation method: 18-48-55 min, RT=53.5 min

Separation column: Luna 200*25 mm 10 um, C18, 110 A and Gemini150*30 mm, C18, 5 um, 110 A, connection, 50° C.

Dissolve method: DMF

Separation purity: 95%

The BCY8234 was synthesized by solid phase synthesis.

Reaction Scheme of BCY8245 is Shown Below:

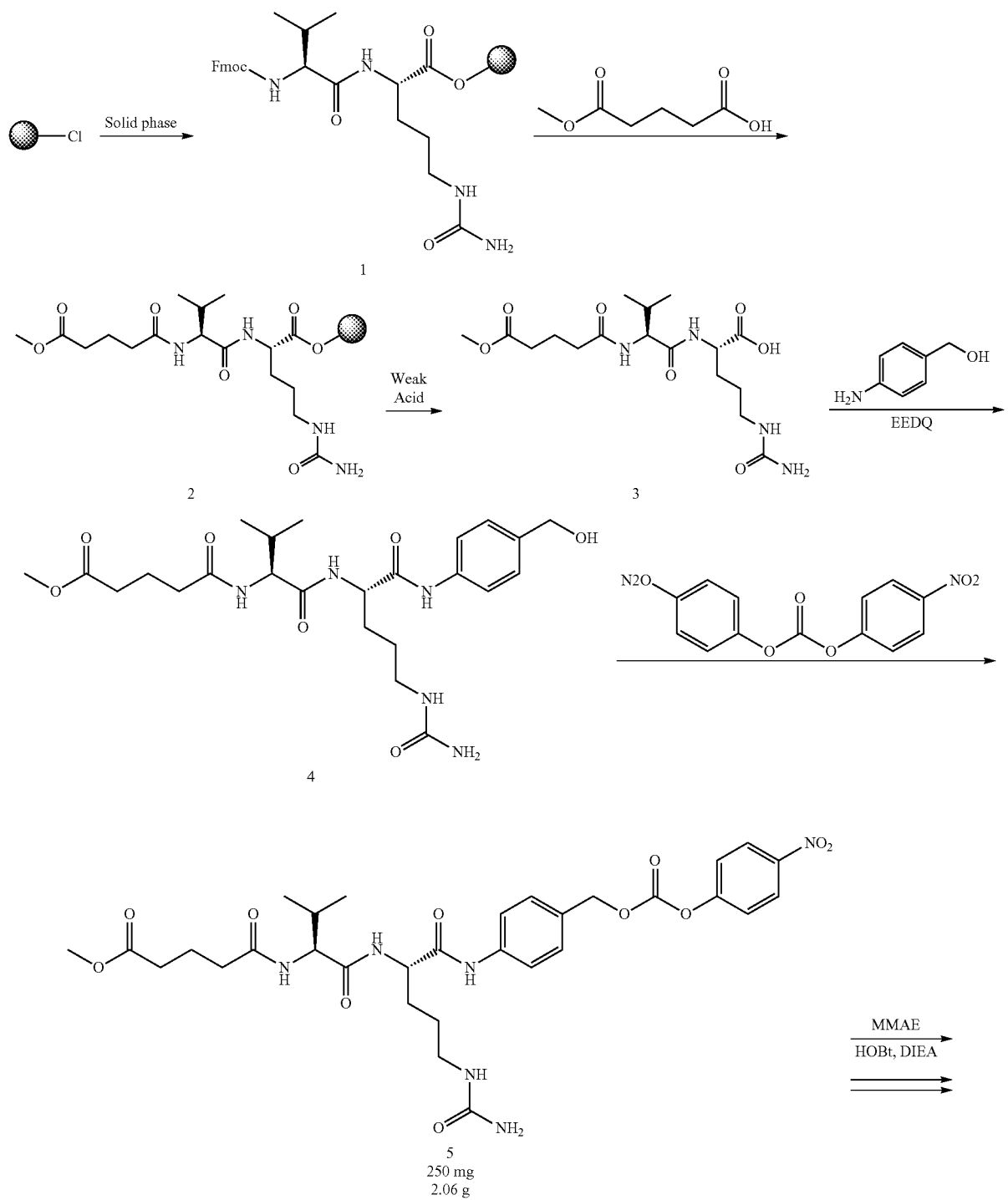

-continued
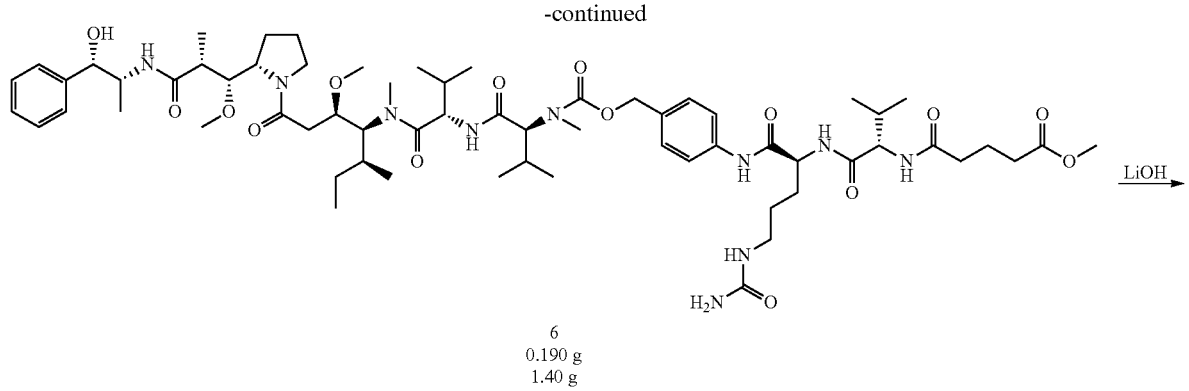
6
0.190 g
1.40 g
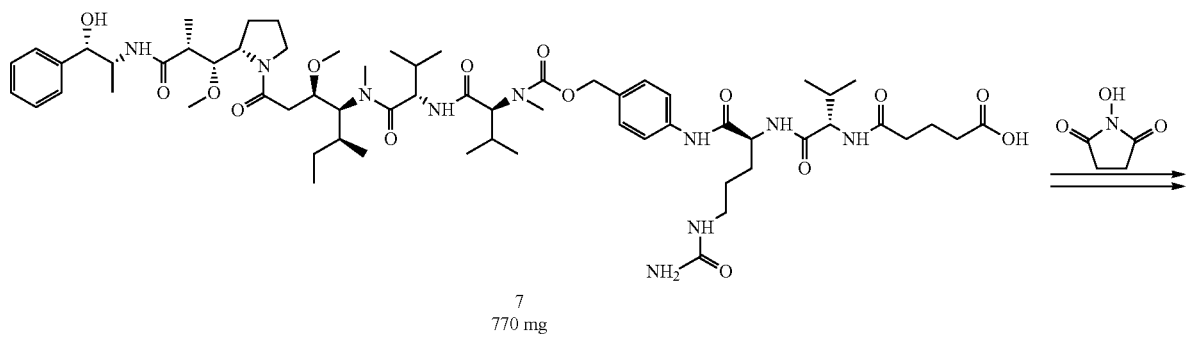
7
770 mg
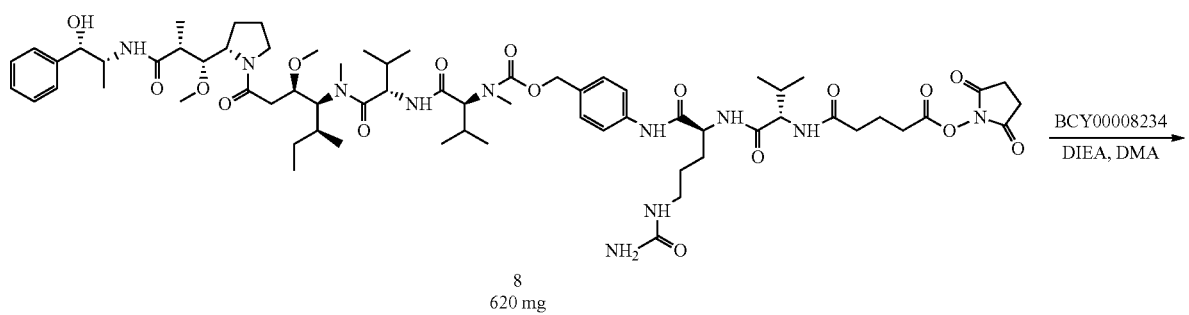
8
620 mg
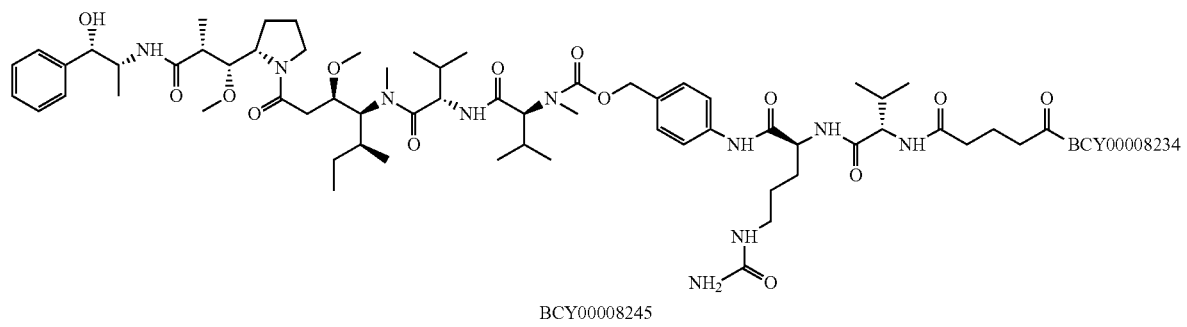
BCY00008245

Preparation of Compound 3

The compound 3 was synthesized by solid phase method.

Preparation of Compound 4

To a solution of compound 3 (1.3 g, 3.23 mmol, 1.0 eq) in DCM (10 mL) and MeOH (5 mL) was added EEDQ (1.60 g, 6.46 mmol, 2.0 eq) and (4-aminophenyl)methanol (517.16 mg, 4.20 mmol, 1.3 eq). The mixture was stirred at 20° C. for 16 hr. LC-MS showed compound 3 was consumed completely and one main peak with desired m/z was detected. The solvent was removed under reduced pressure. The residue was purified by flash silica gel chromatography (ISCO®; 40 g SepaFlash® Silica Flash Column, Eluent of 0~15% DCM/MeOH gradient @ 40 mL/min). Compound 4 (0.950 g, 1.87 mmol, 57.94% yield) was obtained as a yellow solid.

Preparation of Compound 5

To a solution of compound 4 (0.950 g, 1.87 mmol, 1.0 eq) in DMF (5 mL) was added DIEA (1.21 g, 9.36 mmol, 1.63 mL, 5.0 eq) and bis(4-nitrophenyl) carbonate (2.28 g, 7.49 mmol, 4.0 eq). The mixture was stirred at 20° C. for 1 hr. LC-MS showed compound 4 was consumed completely and one main peak with desired m/z was detected. The reaction was directly purified by prep-HPLC (neutral condition). Compound 5 (0.400 g, 594.64 μmol, 31.77% yield) was obtained as a white solid.

Preparation of Compound 6

To a solution of compound 5 (0.200 g, 297.32 μmol, 1.0 eq) in DMF (5 mL) was added HOBt (52.23 mg, 386.51 μmol, 1.3 eq) and DIEA (115.28 mg, 891.95 μmol, 155.36 μL, 3.0 eq), MMAE (192.12 mg, 267.59 μmol, 0.9 eq). The mixture was stirred at 20° C. for 16 hr. LC-MS showed compound 5 was consumed completely and one main peak with desired m/z was detected. The reaction was directly purified by prep-HPLC (neutral condition). Compound 6 (0.160 g, 127.84 μmol, 43.00% yield) was obtained as a white solid.

Preparation of Compound 7

To a solution of compound 6 (0.160 g, 127.84 μmol, 1.0 eq) in THF (3 mL) and H$_2$O (3 mL) was added LiOH.H$_2$O (26.82 mg, 639.21 μmol, 5.0 eq). The mixture was stirred at 20° C. for 1 hr. LC-MS showed compound 6 was consumed completely and one main peak with desired m/z was detected. The THF was removed under reduced pressure and adjusted the pH=7 by AcOH, the mixture was lyophilized. Compound 7 (0.130 g, 105.05 μmol, 82.17% yield) was obtained as a white solid.

Preparation of Compound 8

To a solution of compound 7 (36.27 mg, 315.15 μmol, 3.0 eq) in DMA (6 mL) and DCM (2 mL) was added EDCI (60.41 mg, 315.15 μmol, 3.0 eq). The mixture was stirred at 15° C. for 3 hr. LC-MS showed compound 7 was consumed completely and one main peak with desired m/z was detected. DCM was removed under reduced pressure. The reaction was directly purified by prep-HPLC (neutral condition). Compound 8 (0.095 g, 71.18 μmol, 67.76% yield) was obtained as a white solid.

Preparation of BCY8245

To a solution of BCY8234 (66.41 mg, 22.48 μmol, 1.0 eq) in DMA (4 mL) was added DIEA (8.72 mg, 67.44 μmol, 11.75 μL, 3.0 eq) and compound 8 (0.030 g, 22.48 μmol, 1.0 eq). The mixture was stirred at 20° C. for 16 hr. LC-MS showed BCY8234 was consumed completely and one main peak with desired m/z or desired mass was detected. The reaction was directly purified by prep-HPLC (TFA condition). Compound BCY8245 (0.0427 g, 10.16 μmol, 45.19% yield, 99.30% purity) was obtained as a white solid. Retention time=11.7 min. Mass found=1043.9 (M/4+H)

Biological Data

Nectin-4 Direct Binding Assay

Affinity of the peptides of the invention for human Nectin-4 (Ki) was determined using a fluorescence polarisation assay, in accordance with the methods disclosed in WO 2016/067035. Peptides of the invention with a fluorescent tag (either fluorescein, SIGMA or Alexa Fluor488™, Fisher Scientific) were diluted to 2.5 nM in PBS with 0.01% tween 20 or 50 mM HEPES with 100 mM NaCl and 0.01% tween pH 7.4 (both referred to as assay buffer). This was combined with a titration of protein in the same assay buffer as the peptide to give 1 nM peptide in a total volume of 25 μL in a black walled and bottomed low bind low volume 384 well plates, typically 5 μL assay buffer, 10 μL protein then 10 μL fluorescent peptide. One in two serial dilutions were used to give 12 different concentrations with top concentrations ranging from 500 nM for known high affinity binders to 10 μM for low affinity binders and selectivity assays. Measurements were conducted on a BMG PHERAstar FS equipped with an "FP 485 520 520" optic module which excites at 485 nm and detects parallel and perpendicular emission at 520 nm. The PHERAstar FS was set at 25° C. with 200 flashes per well and a positioning delay of 0.1 second, with each well measured at 5 to 10 minute intervals for 60 minutes. The gain used for analysis was determined for each tracer at the end of the 60 minutes where there was no protein in the well. Data was analysed using Systat Sigmaplot version 12.0. mP values were fit to a user defined quadratic equation to generate a Kd value: f=ymin+(ymax−ymin)/Lig*((x+Lig+Kd)/2−sqrt((((x+Lig+Kd)/2)^2)−(Lig*x))). "Lig" was a defined value of the concentration of tracer used.

Nectin-4 Competition Binding Assay

Peptides without a fluorescent tag were tested in competition with ACPFGCHTDWSWPIWCA-Sar6-K(FI) (SEQ ID NO: 2) and (Kd=5 nM—determined using the protocol above). Peptides were diluted to an appropriate concentration in assay buffer as described in the direct binding assay with a maximum of 5% DMSO, then serially diluted 1 in 2. Five μL of diluted peptide was added to the plate followed by 10 μL of human Nectin-4, then 10 μL fluorescent peptide added. Measurements were conducted as for the direct binding assay, however the gain was determined prior to the first measurement. Data analysis was in Systat Sigmaplot version 12.0 where the mP values were fit to a user defined cubic equation to generate a Ki value:

$$f=y \min+(y \max-y \min)/\text{Lig}*((\text{Lig}*((2*((K\text{lig}+K\text{comp}+\text{Lig}+\text{Comp}-\text{Prot}*c)^2-3*(K\text{comp}*(\text{Lig}-\text{Prot}*c)+K\text{lig}*(\text{Comp}-\text{Prot}*c)+K\text{lig}*K\text{comp}))^0.5*\text{COS}(\text{ARCCOS}((-2*(K\text{lig}+K\text{comp}+\text{Lig}+\text{Comp}-\text{Prot}*c)^3+9*(K\text{lig}+K\text{comp}+\text{Lig}+\text{Comp}-\text{Prot}*c)*(K\text{comp}*(\text{Lig}-\text{Prot}*c)+K\text{lig}*(\text{Comp}-\text{Prot}*c)+K\text{lig}*K\text{comp})-27*(-1*K\text{lig}*K\text{comp}*\text{Prot}*c))/(2*((((K\text{lig}+K\text{comp}+\text{Lig}+\text{Comp}-\text{Prot}*c)^2-3*(K\text{comp}*(\text{Lig}-\text{Prot}*c)+K\text{lig}*(\text{Comp}-\text{Prot}*c)+K\text{lig}*K\text{comp}))^0.5)))/3))-(K\text{lig}+K\text{comp}+\text{Lig}+\text{Comp}-\text{Prot}*c)))/((3*K\text{lig})+((2*((K\text{lig}+K\text{comp}+\text{Lig}+\text{Comp}-\text{Prot}*c)^2-3*(K\text{comp}*(\text{Lig}-\text{Prot}*c)+K\text{lig}*(\text{Comp}-\text{Prot}*c)+K\text{lig}*K\text{comp}))^0.5*\text{COS}(\text{ARCCOS}((-2*(K\text{lig}+K\text{comp}+\text{Lig}+\text{Comp}-\text{Prot}*c)^3+9*(K\text{lig}+K\text{comp}+\text{Lig}+\text{Comp}-\text{Prot}*c)*(K\text{comp}*(\text{Lig}-\text{Prot}*c)+K\text{lig}*(\text{Comp}-\text{Prot}*c)+K\text{lig}*K\text{comp})-27*(-1*K\text{lig}*K\text{comp}*\text{Prot}*c))/(2*((((K\text{lig}+K\text{comp}+\text{Lig}+\text{Comp}-\text{Prot}*c)^2-3*(K\text{comp}*(\text{Lig}-\text{Prot}*c)+K\text{lig}*(\text{Comp}-\text{Prot}*c)+K\text{lig}*K\text{comp}))^3)^0.5))/3))-(K\text{lig}+K\text{comp}+\text{Lig}+\text{Comp}-\text{Prot}*c)))).$$

"Lig", "KLig" and "Prot" were all defined values relating to: fluorescent peptide concentration, the Kd of the fluorescent peptide and Nectin concentration respectively.

Nectin-4 Biacore SPR Binding Assay

Biacore experiments were performed to determine $k_a$ ($M^{-1}s^{-1}$), $k_d$ ($s^{-1}$), $K_D$ (nM) values of monomeric peptides binding to human Necin-4 protein (obtained from Charles River).

Human Nectin-4 (residues Gly32-Ser349; NCBI RefSeq: NP_112178.2) with a gp67 signal sequence and C-terminal FLAG tag was cloned into pFastbac-1 and baculovirus made using standard Bac-to-Bac™ protocols (Life Technologies). Sf21 cells at $1 \times 10^6$ $ml^{-1}$ in Excell-420 medium (Sigma) at 27° C. were infected at an MOI of 2 with a P1 virus stock and the supernatant harvested at 72 hours. The supernatant was batch bound for 1 hour at 4° C. with Anti-FLAG M2 affinity agarose resin (Sigma) washed in PBS and the resin subsequently transferred to a column and washed extensively with PBS. The protein was eluted with 100 µg/ml FLAG peptide. The eluted protein was concentrated to 2 ml and loaded onto an S-200 Superdex column (GE Healthcare) in PBS at 1 ml/min. 2 ml fractions were collected and the fractions containing Nectin-4 protein were concentrated to 16 mg/ml.

The protein was randomly biotinylated in PBS using EZ-Link™ Sulfo-NHS-LC-LC-Biotin reagent (Thermo Fisher) as per the manufacturer's suggested protocol. The protein was extensively desalted to remove uncoupled biotin using spin columns into PBS.

For analysis of peptide binding, a Biacore 3000 instrument was used utilising a CM5 chip (GE Healthcare). Streptavidin was immobilized on the chip using standard amine-coupling chemistry at 25° C. with HBS-N (10 mM HEPES, 0.15 M NaCl, pH 7.4) as the running buffer. Briefly, the carboxymethyl dextran surface was activated with a 7 minute injection of a 1:1 ratio of 0.4 M 1-ethyl-3-(3-dimethylaminopropyl) carbodiimide hydrochloride (EDC)/ 0.1 M N-hydroxy succinimide (NHS) at a flow rate of 10 µl/min. For capture of streptavidin, the protein was diluted to 0.2 mg/ml in 10 mM sodium acetate (pH 4.5) and captured by injecting 120 µl of streptavidin onto the activated chip surface. Residual activated groups were blocked with a 7 minute injection of 1 M ethanolamine (pH 8.5) and biotinylated Nectin-4 captured to a level of 1,200-1,800 RU. Buffer was changed to PBS/0.05% Tween 20 and a dilution series of the peptides was prepared in this buffer with a final DMSO concentration of 0.5%. The top peptide concentration was 100 nM with 6 further 2-fold dilutions. The SPR analysis was run at 25° C. at a flow rate of 50 µl/min with 60 seconds association and dissociation between 400 and 1,200 seconds depending upon the individual peptide. Data were corrected for DMSO excluded volume effects. All data were double-referenced for blank injections and reference surface using standard processing procedures and data processing and kinetic fitting were performed using Scrubber software, version 2.0c (BioLogic Software). Data were fitted using simple 1:1 binding model allowing for mass transport effects where appropriate.

Certain peptide ligands of the invention were tested in the above mentioned Nectin-4 binding assays and the results are shown in Table 1:

TABLE 1

Competition Binding Data for Selected Peptide Ligands of the Invention

| Bicycle No. | $K_i$ (µM) | Number of Experiments |
|---|---|---|
| BCY8122 | 0.003 | 2 |
| BCY8126 | 0.0027 | 6 |

Certain bicyclic peptides of the invention were tested in the above mentioned SPR assay and the results are shown in Table 2:

TABLE 2

SPR Data for Selected Peptide Ligands of the Invention

| Bicycle No. | Human SPR Kd (nM) | n |
|---|---|---|
| BCY8122 | 0.89 | 1 |
| BCY8126 | 1.07 | 4 |
| BCY8116 | 0.372 | 1 | n = mean number of experiments

Certain bicyclic peptides of the invention were conjugated to cytotoxic agents and tested in the above mentioned SPR assay and the results are shown in Table 3:

TABLE 3

SPR Data for Selected BDCs of the Invention

| Bicyclic Drug Conjugate (BDC) No. | Peptide | Human SPR Kd (nM) |
|---|---|---|
| BCY8245 | MMAE-PABC-Cit-Val-Glutaryl-BCY8234 | 5.12 (n = 4) |
| BCY8549 | MMAE-PABC-cyclobutyl-(B-Ala)-BCY8234 | 1.44 (n = 1) |

In Vivo Studies

In each of Examples 1 to 5 and 9 the following methodology was adopted for each study:

Test and Postitive Control Articles

| Number | Physical Description | Molecular Weight | Purity | Storage Condition |
|---|---|---|---|---|
| BCY8245 | Lyophilised powder | 4173.85 | 99.60% | stored at −80° C. |
| BCY8549 | Lyophilised powder | 4157.81 | 95.70% | stored at −80° C. |

Experimental Methods and Procedures (i) Observations

All the procedures related to animal handling, care and the treatment in the study were performed according to the guidelines approved by the Institutional Animal Care and Use Committee (IACUC) of WuXi AppTec, following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss, eye/hair matting and any other abnormal effect as stated in the protocol. Death and observed clinical signs were recorded on the basis of the numbers of animals within each subset.

(ii) Tumor Measurements and the Endpoints

The major endpoint was to see if the tumor growth could be delayed or mice could be cured. Tumor volume was measured three times weekly in two dimensions using a caliper, and the volume was expressed in $mm^3$ using the formula: $V=0.5 \ a \times b^2$ where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day.

TGI was calculated for each group using the formula: TGI (%)=[1−($T_i$−$T_0$)/($V_i$−$V_0$)]×100; $T_i$ is the average tumor volume of a treatment group on a given day, $T_0$ is the average tumor volume of the treatment group on the day of treatment start, $V_i$ is the average tumor volume of the vehicle control group on the same day with $T_i$, and $V_0$ is the average tumor volume of the vehicle group on the day of treatment start.

(iii) Statistical Analysis

Summary statistics, including mean and the standard error of the mean (SEM), are provided for the tumor volume of each group at each time point.

Statistical analysis of difference in tumor volume among the groups was conducted on the data obtained at the best therapeutic time point after the final dose.

A one-way ANOVA was performed to compare tumor volume among groups, and when a significant F-statistics (a ratio of treatment variance to the error variance) was obtained, comparisons between groups were carried out with Games-Howell test. All data were analyzed using GraphPad Prism 5.0. $P<0.05$ was considered to be statistically significant.

Example 1: In Vivo Efficacy Test of BCY8245 in Treatment of NCI-H292 Xenograft (Non-Small Cell Lung Cancer (NSCLC) Model) in BALB/c Nude Mice 1. Study Objective The objective of the research was to evaluate the in vivo anti-tumor efficacy of BCY8245 in treatment of NCI-H292 xenograft model in BALB/c nude mice.

2. Experimental Design

| Group | Treatment | n | Dose (mg/kg) | Dosing Volume (μl/g) | Dosing Route | Schedule |
|---|---|---|---|---|---|---|
| 1 | Vehicle | 3 | — | 10 | iv | biw |
| 2 | BCY8245 | 3 | 1/3/5 | 10 | iv | qw |
| 3 | BCY8245 | 3 | 3 mg/kg | 10 | iv | qw |
| 4 | BCY8245 | 3 | 3 mg/kg | 10 | iv | biw |
| 5 | BCY8245 | 3 | 5 mg/kg | 10 | iv | qw |

Note:
n: animal number;
Dosing volume: adjust dosing volume based on body weight 10 μl/g.

3. Materials
3.1 Animals and Housing Condition
3.1.1. Animals
 Species: *Mus Musculus*
 Strain: Balb/c nude
 Age: 6-8 weeks
 Sex: female
 Body weight: 18-22 g
 Number of animals: 18 mice for BCY8245 plus spare
 Animal supplier: Shanghai LC Laboratory Animal Co., LTD.
3.1.2. Housing Condition
 The mice were kept in individual ventilation cages at constant temperature and humidity with 3 animals in each cage.
 Temperature: 20~26° C.
 Humidity 40-70%.
 Cages: Made of polycarbonate. The size is 300 mm×180 mm×150 mm. The bedding material is corn cob, which is changed twice per week.
 Diet: Animals had free access to irradiation sterilized dry granule food during the entire study period.
 Water: Animals had free access to sterile drinking water.
 Cage identification: The identification labels for each cage contained the following information: number of animals, sex, strain, the date received, treatment, study number, group number and the starting date of the treatment.
 Animal identification: Animals were marked by ear coding.

3.2 Test and Positive Control Articles

4. Experimental Methods and Procedures 4.1 Cell Culture

The NCI-H292 tumor cells will be maintained in medium supplemented with 10% heat inactivated fetal bovine serum at 37° C. in an atmosphere of 5% $CO_2$ in air. The tumor cells will be routinely subcultured twice weekly. The cells growing in an exponential growth phase will be harvested and counted for tumor inoculation.

4.2 Tumor Inoculation

Each mouse will be inoculated subcutaneously at the right flank with NCI-H292 tumor cells ($10×10^6$) in 0.2 ml of PBS for tumor development. The animals will be randomized and treatment will be started when the average tumor volume reaches approximately 158-406 $mm^3$. The test article administration and the animal numbers in each group are shown in the following experimental design table.

4.3 Testing Article Formulation Preparation

| Test article | Con. (mg/ml) | Formulation |
|---|---|---|
| Vehicle | — | 25 mM Histidine pH 7 10% sucrose |
| BCY8245 | 1 | Dissolve 1.61 mg BCY8245 with 1.604 ml buffer(vehicle) |
|  | 0.1 | Dilute 90 μl 1 mg/ml BCY8245 stock with 810 μl buffer(vehicle) |
|  | 0.3 | Dilute 270 μl 1 mg/ml BCY8245 stock with 630 μl buffer(vehicle) |
|  | 0.5 | Dilute 450 μl 1 mg/ml BCY8245 stock with 450 μl buffer(vehicle) |
| Vehicle | — | 25 mM Histidine pH 7 10% sucrose |
| BCY8245 | 1 | Dissolve 10.56 mg BCY8245 in 10.518 ml Histidine buffer |
| BCY8245 | 0.5 | Dilute 400 μl 1 mg/ml BCY8245 stock with 400 μl Histidine buffer |
| BCY8245 | 0.3 | Dilute 240 μl 1 mg/ml BCY8245 stock with 560 μl Histidine buffer |

4.4 Sample Collection

At the end of study, the plasma was collected at 5 min, 15 min, 30 min, 60 min and 120 min post last dosing.

5. Results 5.1 Tumor Growth Curves

Figure 2:
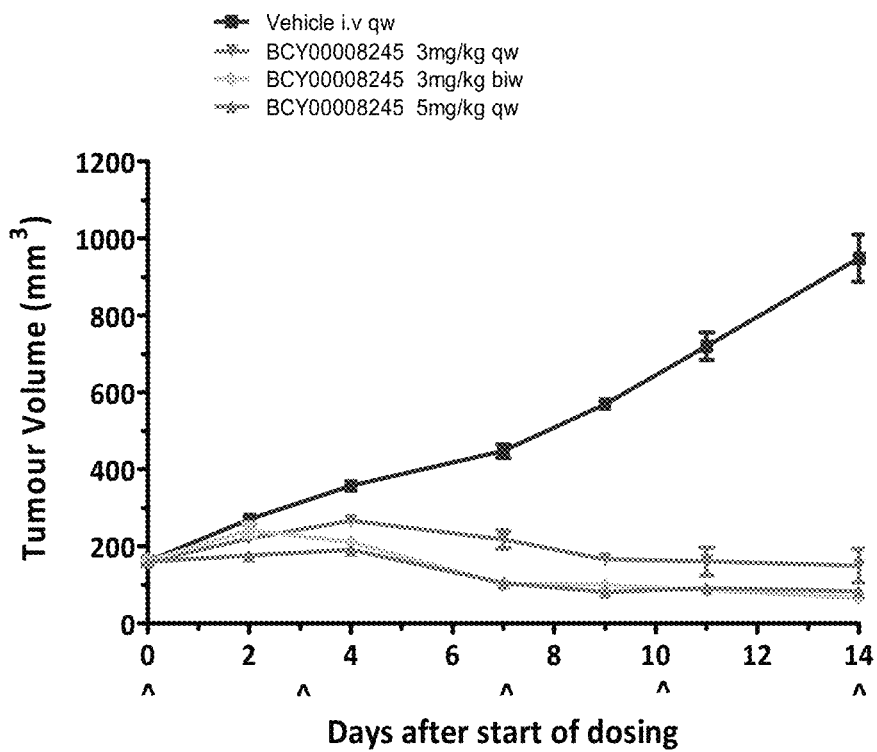

The tumor growth curves are shown in FIGS. 1 and 2.

5.2 Tumor Volume Trace

Mean tumor volume over time in female Balb/c nude mice bearing NCI-H292 xenograft is shown in the below Tables:

TABLE 4

Tumor volume trace over time

| Treatment | 0 | 2 | 4 | 7 | 9 | 11 | 14 | 16 |
|---|---|---|---|---|---|---|---|---|
| Vehicle, qw | 410 ± 77 | 516 ± 69 | 627 ± 61 | 931 ± 141 | 1118 ± 225 | 1208 ± 257 | 1495 ± 365 | 1743 ± 419 |
| BCY8245, 1/3/5 mpk, qw | 404 ± 65 | 391 ± 42 | 542 ± 14 | 721 ± 136 | 762 ± 115 | 607 ± 95 | 614 ± 89 | 626 ± 93 |

| Treatment | 18 | 21 | 23 | 25 | 28 | 30 | 32 | 35 |
|---|---|---|---|---|---|---|---|---|
| Vehicle, qw | 1950 ± 551 | 2149 ± 639 | | | | | | |
| BCY8245, 1/3/5 mpk, qw | 611 ± 93 | 654 ± 152 | 732 ± 139 | 755 ± 132 | 713 ± 114 | 762 ± 165 | 968 ± 290 | 1119 ± 216 |

TABLE 5

Tumor volume trace over time

| | Days after the start of treatment | | | | | | |
|---|---|---|---|---|---|---|---|
| Treatment | 0 | 2 | 4 | 7 | 9 | 11 | 14 |
| Vehicle, qw | 161 ± 2 | 270 ± 14 | 357 ± 14 | 448 ± 17 | 570 ± 16 | 720 ± 36 | 948 ± 61 |
| BCY8245, 3 mpk, qw | 160 ± 5 | 220 ± 11 | 266 ± 15 | 218 ± 23 | 167 ± 10 | 161 ± 36 | 149 ± 43 |
| BCY8245, 3 mpk, biw | 162 ± 13 | 243 ± 19 | 211 ± 12 | 101 ± 11 | 100 ± 8 | 87 ± 7 | 65 ± 3 |
| BCY8245, 5 mpk, qw | 160 ± 9 | 176 ± 7 | 191 ± 3 | 105 ± 8 | 82 ± 3 | 91 ± 14 | 83 ± 8 |

5.3 Tumor Growth Inhibition Analysis

Tumor growth inhibition rate for BCY8245 in the NCI-H292 xenograft model on day 14 was calculated based on tumor volume measurements.

TABLE 6

Tumor growth inhibition analysis

| Treatment | Tumor Volume (mm³)$^a$ | T/C$^b$ (%) | TGI (%) | P value compare with vehicle |
|---|---|---|---|---|
| Vehicle, qw | 2149 ± 639 | — | — | — |
| BCY8245, 1/3/5 mpk, qw | 654 ± 152 | 30.4 | 85.7 | p < 0.05 |

$^a$Mean ± SEM.
$^b$Tumor Growth Inhibition is calculated by dividing the group average tumor volume for the treated group by the group average tumor volume for the control group (T/C).

TABLE 7

Tumor growth inhibition analysis

| Treatment | Tumor Volume (mm³)$^a$ | T/C$^b$ (%) | TGI (%) | P value compared with vehicle |
|---|---|---|---|---|
| Vehicle, qw | 948 ± 61 | — | — | — |
| BCY8245, 3 mpk, qw | 149 ± 43 | 15.8 | 101.4 | p < 0.001 |

TABLE 7-continued

Tumor growth inhibition analysis

| Treatment | Tumor Volume (mm³)$^a$ | T/C$^b$ (%) | TGI (%) | P value compared with vehicle |
|---|---|---|---|---|
| BCY8245, 3 mpk, biw | 65 ± 3 | 6.9 | 112.2 | p < 0.001 |
| BCY8245, 5 mpk, qw | 83 ± 8 | 8.8 | 109.8 | p < 0.001 |

$^a$Mean ± SEM.
$^b$Tumor Growth Inhibition is calculated by dividing the group average tumor volume for the treated group by the group average tumor volume for the control group (T/C).

6. Results Summary and Discussion

In this study, the therapeutic efficacy of BCY8245 in the NCI-H292 xenograft model was evaluated. The measured tumor volumes of all treatment groups at various time points are shown in FIGS. 1 and 2 and Tables 4 to 7.

The mean tumor size of vehicle treated mice reached 879 mm³ on day 14.

BCY8245 at 1 mg/kg didn't produce significant antitumor activity, the test article showed obvious antitumor activity after increasing the dosage to 3 mg/kg from day 7, but the efficacy was not further improved after increasing the dosage to 5 mg/kg on day 21. In this study, all of the treatment animals showed continued bodyweight loss during the dosing schedule, this may be due to the tumor burden and the toxicity of test articles.

BCY8245 at 3 mg/kg, qw (TV=149 mm³, TGI=101.4%, p<0.001), 3 mg/kg, biw (TV=65 mm³, TGI=112.2%, p<0.001) and 5 mg/kg, qw (TV=83 mm³, TGI=109.8%, p<0.001) produced significant antitumor activity.

Example 2: In Vivo Efficacy Test of BCY7825, BCY8245, BCY8253, BCY8254 and BCY8255 in Treatment of HT-1376 Xenograft (Bladder Cancer Model) in CB17-SCID Mice 1. Study Objective The objective of the research is to evaluate the in vivo anti-tumor efficacy of test articles in treatment of HT-1376 xenograft in CB17-SCID mice.

2. Experimental Design

| Group | Treatment | n | Dose (mg/kg) | Dosing Volume (μl/g) | Dosing Route | Schedule |
| --- | --- | --- | --- | --- | --- | --- |
| 1 | Vehicle | 3 | — | 10 | iv | qw |
| 2 | BCY8245 | 3 | 1/3ᵃ mg/kg | 10 | iv | qw |
| 3 | Vehicle | 5 | — | 10 | iv | qw |
| 4 | BCY8245 | 3 | 3 mg/kg | 10 | iv | qw |
| 5 | BCY8245 | 3 | 3 mg/kg | 10 | iv | biw |
| 6 | BCY8245 | 3 | 5 mg/kg | 10 | iv | qw |

ᵃ1 mg/kg for the first week and 3 mg/kg for the following 2 weeks

3. Materials
3.1 Animals and Housing Condition
3.1.1. Animals
   Species: *Mus Musculus*
   Strain: CB17-SCID
   Age: 6-8 weeks
   Sex: female
   Body weight: 18-22 g
   Number of animals: 21-41 mice plus spare
   Animal supplier: Shanghai LC Laboratory Animal Co., LTD.
3.1.2. Housing Condition
   The mice were kept in individual ventilation cages at constant temperature and humidity with 3 or 5 animals in each cage.
   Temperature: 20~26° C.
   Humidity 40-70%.
   Cages: Made of polycarbonate. The size is 300 mm×180 mm×150 mm. The bedding material is corn cob, which is changed twice per week.
   Diet: Animals had free access to irradiation sterilized dry granule food during the entire study period.
   Water: Animals had free access to sterile drinking water.
   Cage identification: The identification labels for each cage contained the following information: number of animals, sex, strain, the date received, treatment, study number, group number and the starting date of the treatment.
   Animal identification: Animals were marked by ear coding.

4. Experimental Methods and Procedures
4.1 Cell Culture

The HT-1376 tumor cells were maintained in vitro as a monolayer culture in EMEM medium supplemented with 10% heat inactivated fetal bovine serum at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

4.2 Tumor Inoculation

Each mouse was inoculated subcutaneously at the right flank with HT-1376 tumor cells ($5×10^6$) in 0.2 ml of PBS with matrigel (1:1) for tumor development. Animals were randomized when the average tumor volume reached 153-164 mm³. The test article administration and the animal numbers in each group were shown in the experimental design table.

4.3 Testing Article Formulation Preparation

| Test article | Con. (mg/ml) | Formulation |
| --- | --- | --- |
| Vehicle | — | 25 mM Histidine pH 7 10% sucrose |
| BCY8245 | 0.1 | Dilute 90 μl 1 mg/ml BCY8245 stock with 810 μl buffer (vehicle) |
| BCY8245 | 0.3 | Dilute 270 μl 1 mg/ml BCY8245 stock with 630 μl buffer (vehicle) |
| Vehicle | — | 25 mM Histidine pH 7 10% sucrose |
| BCY8245 | 0.5 | Dilute 400 μl 1 mg/ml BCY8245 stock with 400 μl Histidine buffer |
| BCY8245 | 0.3 | Dilute 240 μl 1 mg/ml BCY8245 stock with 560 μl Histidine buffer |

4.4 Sample Collection

At the end of study, the plasma of group 2 was collected at 5 min, 15 min, 30 min, 60 min and 120 min post last dosing. The plasma of group 6 was collected at 5 min, 15 min, 30 min, 60 min and 120 min post last dosing. The tumor of group 6 was collected at 2 h post last dosing. The tumor of groups 4 and 5 were collected at 2 h post last dosing.

5. Results
5.1 Tumor Growth Curves

Figure 3:
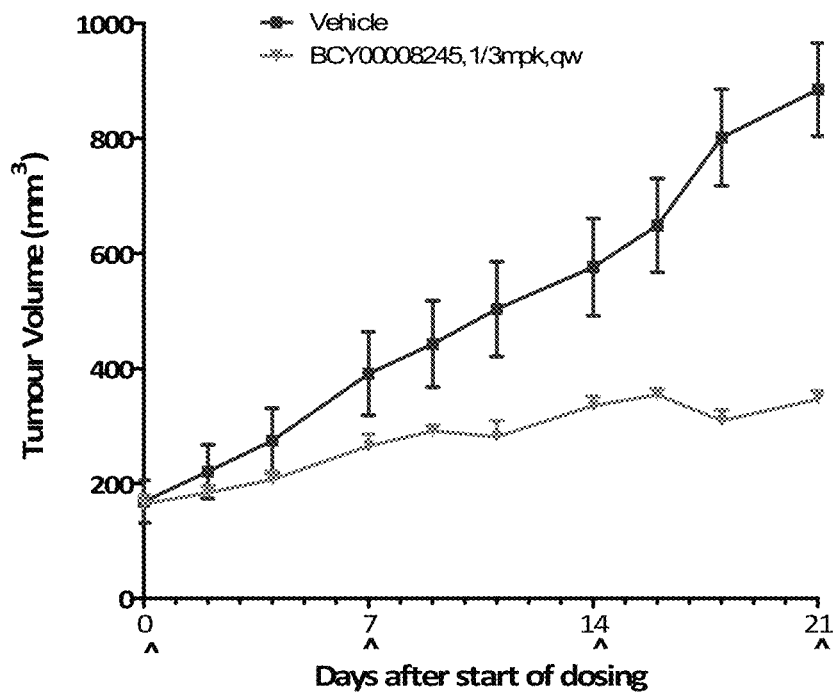
FIGS. 3 and 4: Tumor volume traces after administering BCY8245 to female CB17-SCID mice bearing HT-1376 xenograft.
Figure 4:
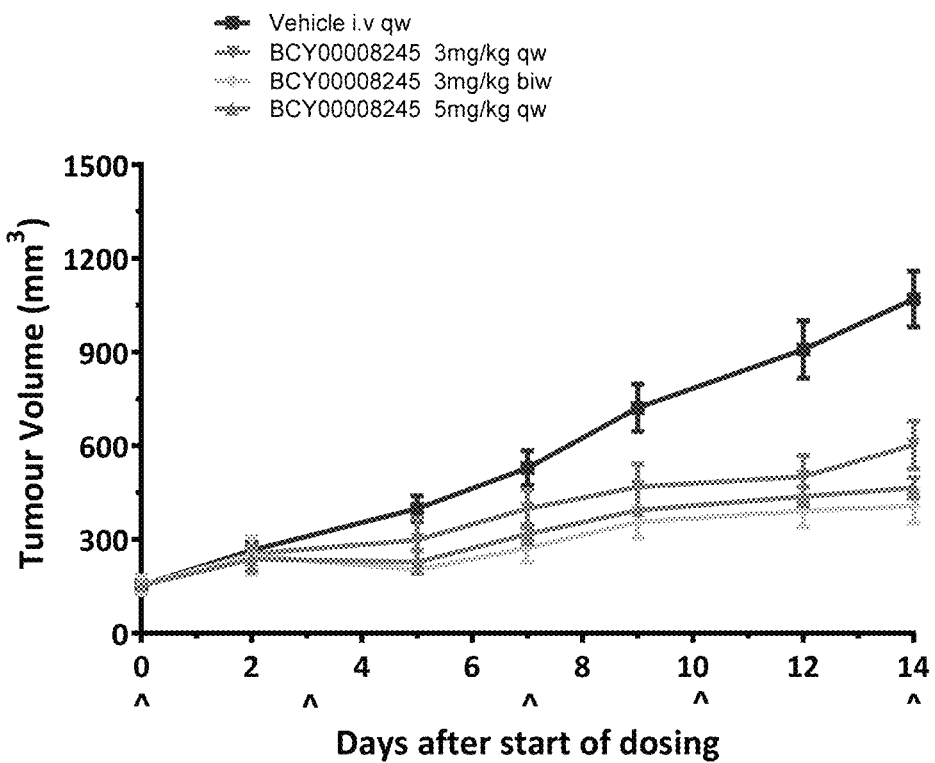

Tumor growth curves are shown in FIGS. 3 and 4.

5.2 Tumor Volume Trace

Mean tumor volume overtime in female CB17-SCID mice bearing HT-1376 xenograft is shown in Tables 8 and 9.

TABLE 8

Tumor volume trace over time

| Gr. Treatment | Days after the start of treatment | | | | | | | | | |
| --- | --- | --- | --- | --- | --- | --- | --- | --- | --- | --- |
| | 0 | 2 | 4 | 7 | 9 | 11 | 14 | 16 | 18 | 21 |
| 1 Vehicle, qw | 168 ± 37 | 220 ± 47 | 274 ± 56 | 391 ± 73 | 442 ± 75 | 503 ± 82 | 576 ± 84 | 649 ± 81 | 801 ± 84 | 884 ± 81 |
| 2 BCY8245, 1/3 mpk, qw | 164 ± 16 | 184 ± 12 | 206 ± 14 | 265 ± 21 | 291 ± 10 | 281 ± 28 | 335 ± 16 | 354 ± 11 | 309 ± 19 | 347 ± 14 |

TABLE 9

Tumor volume trace over time

| | | Days after the start of treatment | | | | | |
|---|---|---|---|---|---|---|---|
| Gr. | Treatment | 0 | 2 | 5 | 7 | 9 | 12 | 14 |
| 3 | Vehicle, qw | 153 ± 16 | 266 ± 30 | 398 ± 41 | 529 ± 56 | 721 ± 76 | 908 ± 91 | 1069 ± 90 |
| 4 | BCY8245, 3 mpk, qw | 153 ± 26 | 254 ± 53 | 298 ± 69 | 398 ± 61 | 468 ± 73 | 502 ± 67 | 603 ± 76 |
| 5 | BCY8245, 3 mpk, biw | 154 ± 30 | 248 ± 58 | 203 ± 15 | 273 ± 45 | 356 ± 50 | 391 ± 53 | 407 ± 53 |
| 6 | BCY8245, 5 mpk, qw | 153 ± 15 | 237 ± 41 | 228 ± 36 | 317 ± 31 | 394 ± 20 | 438 ± 31 | 465 ± 33 |

5.3 Tumor Growth Inhibition Analysis

Tumor growth inhibition rate for Test articles in the HT-1376 xenograft model was calculated based on tumor volume measurements at day 21 after the start of treatment.

TABLE 10

Tumor growth inhibition analysis

| Gr | Treatment | Tumor Volume (mm$^3$)$^a$ | T/C$^b$ (%) | TGI (%) | P value compared with vehicle |
|---|---|---|---|---|---|
| 1 | Vehicle, qw | 884 ± 81 | — | — | — |
| 2 | BCY8245, 3 mpk, qw | 347 ± 14 | 39.2 | 74.5 | p < 0.001 |

$^a$Mean ± SEM.
$^b$Tumor Growth Inhibition is calculated by dividing the group average tumor volume for the treated group by the group average tumor volume for the control group (T/C).

TABLE 11

Tumor growth inhibition analysis

| Gr | Treatment | Tumor Volume (mm$^3$)$^a$ | T/C$^b$ (%) | TGI (%) | P value compared with vehicle |
|---|---|---|---|---|---|
| 3 | Vehicle, qw | 1069 ± 90 | — | — | — |
| 4 | BCY8245, 3 mpk, qw | 603 ± 76 | 56.4 | 50.9 | p < 0.01 |
| 5 | BCY8245, 3 mpk, biw | 407 ± 53 | 38.1 | 72.3 | p < 0.001 |
| 6 | BCY8245, 5 mpk, qw | 465 ± 33 | 43.5 | 66.0 | p < 0.001 |

$^a$Mean ± SEM.
$^b$Tumor Growth Inhibition is calculated by dividing the group average tumor volume for the treated group by the group average tumor volume for the control group (T/C).

6. Results Summary and Discussion

Groups 1 and 2

In this study, the therapeutic efficacy of test articles in the HT-1376 xenograft model was evaluated. The measured tumor volumes of all treatment groups at various time points are shown in FIG. 3 and Tables 8 and 10.

The mean tumor size of vehicle treated mice reached 884 mm$^3$ on day 21. BCY8245 at 1 mg/kg produced slight antitumor activity, and better efficacy was found after increasing dosage to 3 mg/kg from day 7.

In this study, some mice treated with the test article at 3 mg/kg showed over 10% bodyweight loss.

Groups 3-6

In this study, the therapeutic efficacy of test articles in the HT-1376 xenograft model was evaluated. The measured tumor volumes of all treatment groups at various time points are shown in FIG. 4 and Tables 9 and 11.

BCY8245 at 3 mg/kg, qw (TV=603 mm$^3$, TGI=50.9%, p<0.01), 3 mg/kg, biw (TV=407 mm$^3$, TGI=72.3%, p<0.001) and 5 mg/kg, qw (TV=465 mm$^3$, TGI=66.0%, p<0.001) produced significant antitumor activity.

In this study, BCY8245 at 5 mg/kg qw caused over 10% animal bodyweight loss during the treatment schedule.

Example 3: In Vivo Efficacy Study of BCY8245 in Treatment of Panc2.13 Xenograft (Pancreatic Cancer Model) in Balb/c Nude Mice 1. Study Objective The objective of the research is to evaluate the in vivo anti-tumor efficacy of test articles in treatment of Panc2.13 xenograft in Balb/c nude mice.

2. Experimental Design

| Group | Treatment | n | Dose (mg/kg) | Dosing Volume (μl/g) | Dosing Route | Schedule |
|---|---|---|---|---|---|---|
| 1 | Vehicle | 5 | — | 10 | iv | qw |
| 2 | BCY8245 | 3 | 3 mg/kg | 10 | iv | qw |
| 3 | BCY8245 | 3 | 3 mg/kg | 10 | iv | biw |
| 4 | BCY8245 | 3 | 5 mg/kg | 10 | iv | qw |

3. Materials
3.1 Animals and Housing Condition
3.1.1 Animals
  Species: *Mus Musculus*
  Strain: Balb/c nude
  Age: 6-8 weeks
  Sex: female
  Body weight: 18-22 g
  Number of animals: 41 mice plus spare
  Animal supplier: Shanghai LC Laboratory Animal Co., LTD.
3.1.2. Housing Condition
  The mice were kept in individual ventilation cages at constant temperature and humidity with 3 or 5 animals in each cage.
  Temperature: 20~26° C.
  Humidity 40-70%.

Cages: Made of polycarbonate. The size is 300 mm×180 mm×150 mm. The bedding material is corn cob, which is changed twice per week.

Diet: Animals had free access to irradiation sterilized dry granule food during the entire study period.

Water: Animals had free access to sterile drinking water.

Cage identification: The identification labels for each cage contained the following information: number of animals, sex, strain, the date received, treatment, study number, group number and the starting date of the treatment.

Animal identification: Animals were marked by ear coding.

4. Experimental Methods and Procedures 4.1 Cell Culture

The Panc2.13 tumor cells will be maintained in RMPI1640 medium supplemented with 15% heat inactivated fetal bovine serum and 10 units/ml human recombinant insulin at 37° C. in an atmosphere of 5% $CO_2$ in air. The tumor cells will be routinely subcultured twice weekly. The cells growing in an exponential growth phase will be harvested and counted for tumor inoculation.

4.2 Tumor Inoculation

Each mouse was inoculated subcutaneously at the right flank with Panc2.13 tumor cells ($5×10^6$) with Matrigel (1:1) in 0.2 ml of PBS for tumor development. 41 animals were randomized when the average tumor volume reached 149 $mm^3$. The test article administration and the animal numbers in each group were shown in the experimental design table.

4.3 Testing Article Formulation Preparation

| Test article | Con. (mg/ml) | Formulation |
| --- | --- | --- |
| Vehicle | — | 25 mM Histidine pH 7 10% sucrose |
| BCY8245 | 0.5 | Dilute 400 μl 1 mg/ml BCY8245 stock with 400 μl Histidine buffer |
| BCY8245 | 0.3 | Dilute 240 μl 1 mg/ml BCY8245 stock with 560 μl Histidine buffer |

4.4 Sample Collection

At the end of study, the tumor of all groups were collected at 2 h post last dosing.

5. Results 5.1 Tumor Growth Curves

Figure 5:
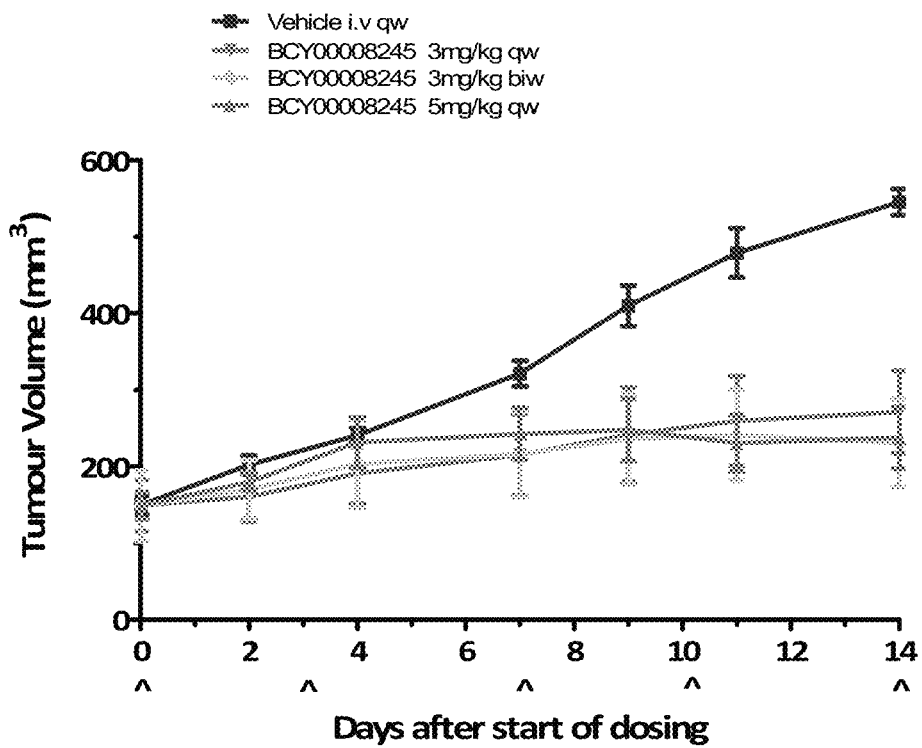
FIG. 5: Tumor volume trace after administering BCY8245 to female Balb/c nude mice bearing Panc2.13 xenograft.

The tumor growth curve is shown in FIG. 5.

5.2 Tumor Volume Trace

Mean tumor volume over time in female Balb/c nude mice bearing Panc2.13 xenograft is shown in Table 12.

TABLE 12

Tumor volume trace over time

| | | Days after the start of treatment | | | | | |
| --- | --- | --- | --- | --- | --- | --- | --- |
| Gr. Treatment | 0 | 2 | 4 | 7 | 9 | 11 | 14 |
| 1 Vehicle, qw | 149 ± 12 | 202 ± 12 | 240 ± 9 | 321 ± 17 | 410 ± 27 | 479 ± 32 | 545 ± 17 |
| 2 BCY8245, 3 mpk, qw | 149 ± 34 | 160 ± 33 | 191 ± 39 | 215 ± 53 | 242 ± 62 | 259 ± 59 | 271 ± 54 |
| 3 BCY8245, 3 mpk, biw | 148 ± 46 | 170 ± 38 | 204 ± 57 | 216 ± 56 | 236 ± 59 | 241 ± 60 | 231 ± 57 |
| 4 BCY8245, 5 mpk, qw | 149 ± 18 | 180 ± 11 | 231 ± 33 | 242 ± 34 | 248 ± 40 | 231 ± 37 | 238 ± 40 |

5.3 Tumor Growth Inhibition Analysis

Tumor growth inhibition rate for Test articles in the Panc2.13 xenograft model was calculated based on tumor volume measurements at day 14 after the start of treatment.

TABLE 13

Tumor growth inhibition analysis

| Gr | Treatment | Tumor Volume $(mm^3)^a$ | $T/C^b$ (%) | TGI (%) | P value compared with vehicle |
| --- | --- | --- | --- | --- | --- |
| 1 | Vehicle, qw | 545 ± 17 | — | — | — |
| 2 | BCY8245, 3 mpk, qw | 271 ± 54 | 49.6 | 69.2 | p < 0.01 |
| 3 | BCY8245, 3 mpk, biw | 231 ± 57 | 42.3 | 79.1 | p < 0.001 |
| 4 | BCY8245, 5 mpk, qw | 238 ± 40 | 43.6 | 77.5 | p < 0.001 |

$^a$Mean ± SEM.
$^b$Tumor Growth Inhibition is calculated by dividing the group average tumor volume for the treated group by the group average tumor volume for the control group (T/C).

6. Results Summary and Discussion

In this study, the therapeutic efficacy of test articles in the Panc2.13 xenograft model was evaluated. The measured tumor volumes of all treatment groups at various time points are shown in FIG. 5 and Tables 12 and 13.

BCY8245 at 3 mg/kg, qw (TV=271 $mm^3$, TGI=69.2%, p<0.01), 3 mg/kg, biw (TV=231 $mm^3$, TGI=79.1%, p<0.001) and 5 mg/kg, qw (TV=238 $mm^3$, TGI=77.5%, p<0.001) produced significant antitumor activity.

Example 4: In Vivo Efficacy Study of BCY8245 in Treatment of MDA-MB-468 Xenograft (Breast Cancer Model) in Balb/c Nude Mice 1. Study Objective The objective of the research is to evaluate the in vivo anti-tumor efficacy of BCY8245 in treatment of MDA-MB-468 xenograft in Balb/c nude mice.

2. Experimental Design

| Group | Treatment | n | Dose (mg/kg) | Dosing Volume (μl/g) | Dosing Route | Schedule |
| --- | --- | --- | --- | --- | --- | --- |
| 1 | Vehicle | 5 | — | 10 | iv | qw |
| 2 | BCY8245 | 3 | 3 mg/kg | 10 | iv | qw |

-continued

| Group | Treatment | n | Dose (mg/kg) | Dosing Volume (μl/g) | Dosing Route | Schedule |
|---|---|---|---|---|---|---|
| 3 | BCY8245 | 3 | 3 mg/kg | 10 | iv | biw |
| 4 | BCY8245 | 3 | 5 mg/kg | 10 | iv | qw |

3. Materials
3.1 Animals and Housing Condition
3.1.1 Animals
  Species: *Mus Musculus*
  Strain: Balb/c nude
  Age: 6-8 weeks
  Sex: female
  Body weight: 18-22 g
  Number of animals: 41 mice plus spare
  Animal supplier: Shanghai LC Laboratory Animal Co., LTD.
3.1.2. Housing Condition
  The mice were kept in individual ventilation cages at constant temperature and humidity with 3 or 5 animals in each cage.
  Temperature: 20~26° C.
  Humidity 40-70%.
  Cages: Made of polycarbonate. The size is 300 mm×180 mm×150 mm. The bedding material is corn cob, which is changed twice per week.
  Diet: Animals had free access to irradiation sterilized dry granule food during the entire study period.
  Water: Animals had free access to sterile drinking water.
  Cage identification: The identification labels for each cage contained the following information: number of animals, sex, strain, the date received, treatment, study number, group number and the starting date of the treatment.
  Animal identification: Animals were marked by ear coding.

4. Experimental Methods and Procedures
4.1 Cell Culture
The tumor cells were maintained in Leibovitz's L-15 medium supplemented with 10% heat inactivated fetal bovine serum at 37° C. in an atmosphere of 5% $CO_2$ in air. The tumor cells were routinely subcultured twice weekly. The cells growing in an exponential growth phase were harvested and counted for tumor inoculation.
4.2 Tumor Inoculation
Each mouse was inoculated subcutaneously at the right flank with MDA-MB-468 tumor cells ($10 \times 10^6$) in 0.2 ml of PBS supplemented with 50% matrigel for tumor development. 41 animals were randomized when the average tumor volume reached 196 mm$^3$. The test article administration and the animal numbers in each group were shown in the experimental design table.
4.3 Testing Article Formulation Preparation

| Test article | Con. (mg/ml) | Formulation |
|---|---|---|
| Vehicle | — | 25 mM Histidine pH 7 10% sucrose |
| BCY8245 | 1 | Dissolve 10.56 mg BCY8245 in 10.518 ml Histidine buffer |
| BCY8245 | 0.5 | Dilute 400 μl 1 mg/ml BCY8245 stock with 400 μl Histidine buffer |
| BCY8245 | 0.3 | Dilute 240 μl 1 mg/ml BCY8245 stock with 560 μl Histidine buffer |

Figure 6:
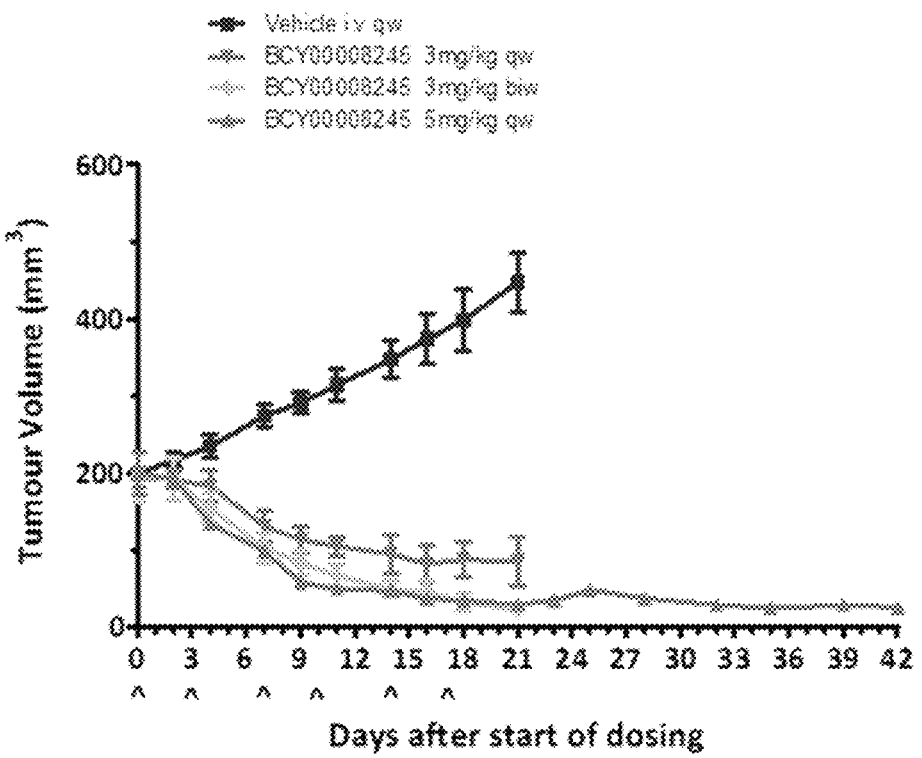
FIG. 6: Tumor volume trace after administering BCY8245 to female Balb/c nude mice bearing MDA-MB-468 xenograft.

4.4 Sample Collection
At the day 21 of study, the plasma of group 2 was collected at 5 min, 15 min, 30 min, 60 min and 120 min post last dosing. The tumors of groups 1 and 3 were collected at 2 h post last dosing. The animals in group 4 were kept running for another 21 days without any dosing, and the tumors of these groups were collected on day 42.
5. Results
5.1 Tumor Growth Curves
The tumor growth curve is shown in FIG. 6.
5.2 Tumor Volume Trace
Mean tumor volume over time in female Balb/c nude mice bearing MDA-MB-468 xenograft is shown in Tables 14 and 15.

TABLE 14

Tumor volume trace over time (Day 0 to day 21)

| | | Days after the start of treatment | | | | | | | | |
|---|---|---|---|---|---|---|---|---|---|---|
| Gr. | Treatment | 0 | 2 | 4 | 7 | 9 | 11 | 14 | 16 | 18 | 21 |
| 1 | Vehicle, qw | 199 ± 6 | 217 ± 9 | 235 ± 15 | 274 ± 14 | 291 ± 14 | 314 ± 20 | 348 ± 24 | 374 ± 33 | 398 ± 39 | 447 ± 39 |
| 2 | BCY8245, 3 mpk, qw | 194 ± 12 | 192 ± 26 | 184 ± 20 | 131 ± 20 | 113 ± 17 | 104 ± 13 | 94 ± 25 | 81 ± 23 | 87 ± 23 | 85 ± 31 |
| 3 | BCY8245, 3 mpk, biw | 195 ± 33 | 193 ± 27 | 154 ± 20 | 103 ± 20 | 83 ± 16 | 67 ± 14 | 49 ± 11 | 45 ± 14 | 32 ± 12 | 22 ± 4 |
| 4 | BCY8245, 5 mpk, qw | 199 ± 28 | 193 ± 11 | 135 ± 4 | 98 ± 5 | 58 ± 5 | 49 ± 5 | 47 ± 2 | 37 ± 4 | 35 ± 3 | 29 ± 3 |

TABLE 15

Tumor volume trace over time (Day 23 to day 42)

| | | Days after the start of treatment | | | | | | |
|---|---|---|---|---|---|---|---|---|
| Gr. | Treatment | 23 | 25 | 28 | 32 | 35 | 39 | 42 |
| 4 | BCY8245, 5 mpk, qw | 35 ± 5 | 48 ± 5 | 37 ± 7 | 28 ± 6 | 24 ± 4 | 28 ± 6 | 26 ± 6 |

5.3 Tumor Growth Inhibition Analysis

Tumor growth inhibition rate for test articles in the MDA-MB-468 xenograft model was calculated based on tumor volume measurements at day 21 after the start of the treatment.

TABLE 16

Tumor growth inhibition analysis

| Gr | Treatment | Tumor Volume | T/C[b] (%) | TGI (%) | P value with |
|---|---|---|---|---|---|
| 1 | Vehicle, qw | 447 ± 39 | — | — | — |
| 2 | BCY8245, 3 mpk, qw | 85 ± 31 | 18.9 | 144.2 | p < 0.001 |
| 3 | BCY8245, 3 mpk, biw | 22 ± 4 | 4.9 | 169.8 | p < 0.001 |
| 4 | BCY8245, 5 mpk, qw | 29 ± 3 | 6.6 | 168.4 | p < 0.001 |

[a]Mean ± SEM.
[b]Tumor Growth Inhibition is calculated by dividing the group average tumor volume for the treated group by the group average tumor volume for the control group (T/C).

6. Results Summary and Discussion

In this study, the therapeutic efficacy of test articles in the MDA-MB-468 xenograft model was evaluated. The measured tumor volumes of all treatment groups at various time points are shown in FIG. 6 and Tables 14 to 16.

BCY8245 at 3 mg/kg, qw (TV=85 mm$^3$, TGI=144.2%, p<0.001), 3 mg/kg, biw (TV=22 mm$^3$, TGI=169.8%, p<0.001) and 5 mg/kg, qw (TV=29 mm$^3$, TGI=168.4%, p<0.001) produced significant anti-tumor antitumor activity in dose or dose-frequency dependent manner.

The dosing of 5 mg/kg groups were suspended from day 21, the tumors didn't show any relapse during extra 3 weeks' monitoring schedule.

Example 5: In Vivo Efficacy Test of BCY8549 in Treatment of NCI-H292 Xenograft (Non-Small Cell Lung Cancer (NSCLC) Model) in BALB/c Nude Mice 1. Study Objective The objective of the research is to evaluate the in vivo anti-tumor efficacy of BCY8549 in treatment of NCI-H292 xenograft in Balb/c nude mice.

2. Experimental Design

| Group | Treatment | n | Dose (mg/kg) | Dosing Volume (μl/g) | Dosing Route | Schedule |
|---|---|---|---|---|---|---|
| 1 | Vehicle | 4 | — | 10 | iv | qw |
| 2 | BCY8549 | 3 | 3 | 10 | iv | qw |

3. Materials
3.1 Animals and Housing Condition
3.1.1. Animals
  Species: *Mus Musculus*
  Strain: Balb/c nude
  Age: 6-8 weeks
  Sex: female
  Body weight: 18-22 g
  Number of animals: 43 mice plus spare
  Animal supplier: Shanghai Lingchang Biotechnology Experimental Animal Co. Ltd 3.1.2. Housing Condition
  The mice were kept in individual ventilation cages at constant temperature and humidity with 3 or 4 animals in each cage.
  Temperature: 20~26° C.
  Humidity 40-70%.
  Cages: Made of polycarbonate. The size is 300 mm×180 mm×150 mm. The bedding material is corn cob, which is changed twice per week.
  Diet: Animals had free access to irradiation sterilized dry granule food during the entire study period.
  Water: Animals had free access to sterile drinking water.
  Cage identification: The identification labels for each cage contained the following information: number of animals, sex, strain, the date received, treatment, study number, group number and the starting date of the treatment.
  Animal identification: Animals were marked by ear coding.

4. Experimental Methods and Procedures
4.1 Cell Culture

The NCI-H292 tumor cells were maintained in vitro as a monolayer culture in RPMI-1640 medium supplemented with 10% heat inactivated fetal bovine serum at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

4.2 Tumor Inoculation

Each mouse was inoculated subcutaneously at the right flank with NCI-H292 tumor cells (10×10$^6$) in 0.2 ml of PBS for tumor development. 43 animals were randomized when the average tumor volume reached 168 mm$^3$. The test article administration and the animal numbers in each group were shown in the experimental design table.

Testing Article Formulation Preparation

| Treatment | Con. (mg/ml) | Formulation |
|---|---|---|
| Vehicle | — | 25 mM Histidine pH 7 10% sucrose |
| BCY8549 | 1 | Dissolved 2 mg BCY8549 with 1914 μl vehicle buffer |
| BCY8549 | 0.3 | Dilute 240 μl 1 mg/ml BCY8549 stock with 560 μl vehicle buffer |

4.4 Sample Collection

At the end of study, the plasma of group 2 mice was collected at 5 min, 15 min, 30 min, 1 h and 2 h post the last dosing.

5. Results
5.1 Tumor Growth Curves

Figure 7:
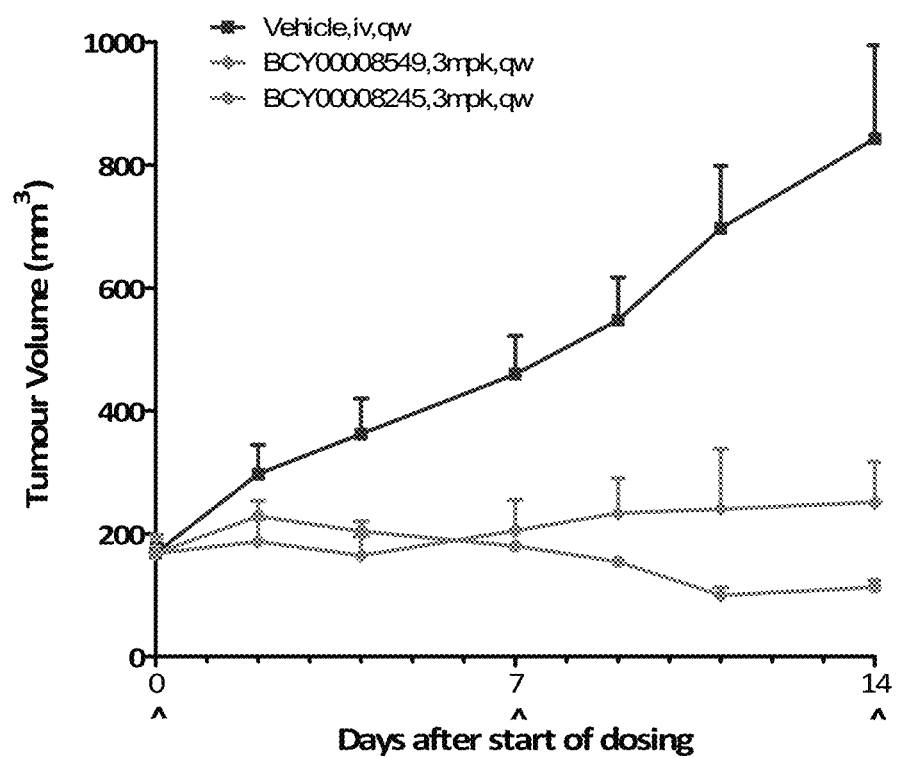
FIG. 7: Tumor volume trace after administering BCY8549 (with BCY8245 as control), to female BALB/c nude mice bearing NCI-H292 xenograft.
Figure 8:
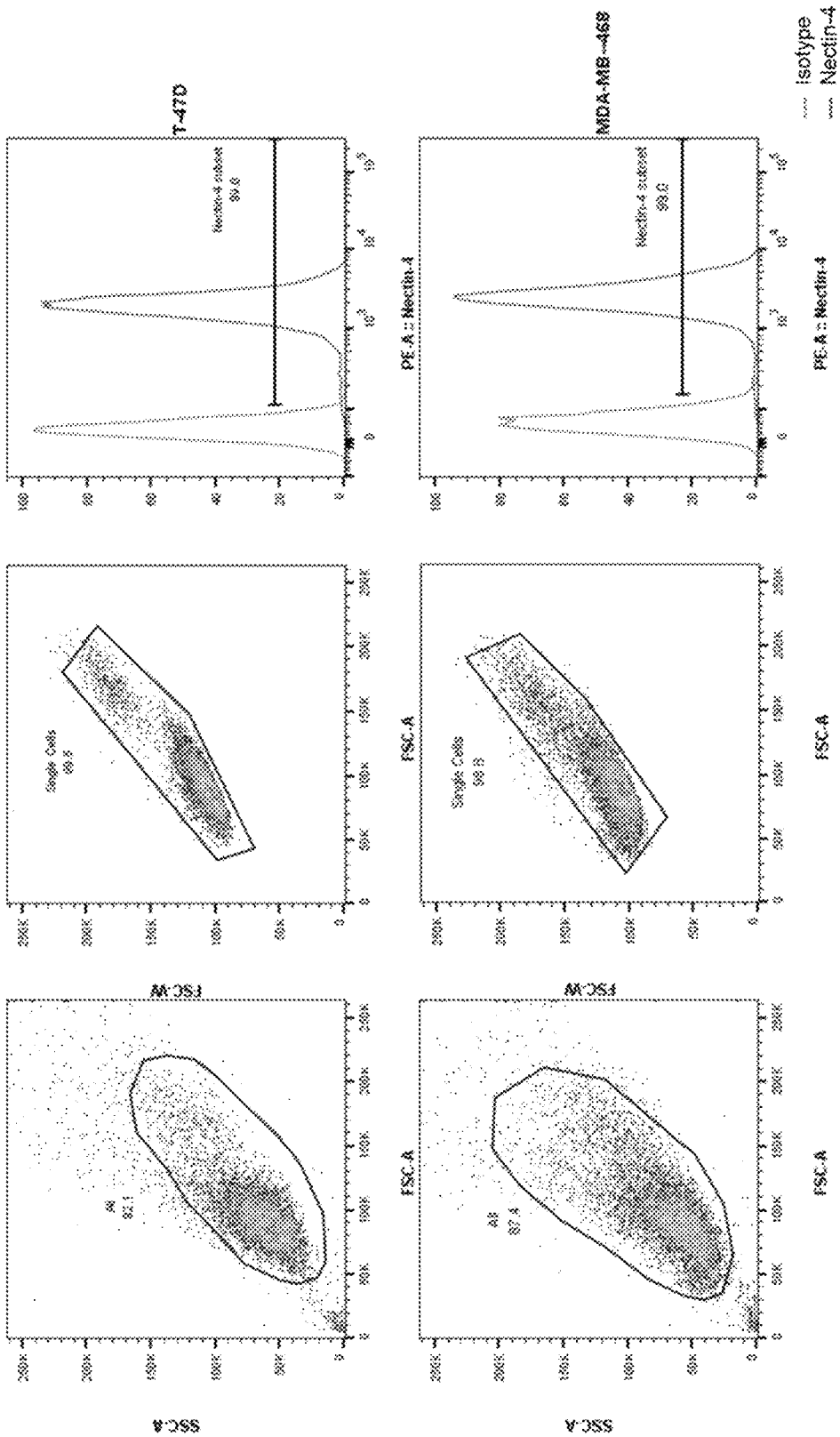
FIG. 8: Gating strategy for Nectin-4 in Breast (T-47D and MDA-MB-468).
Figure 9:
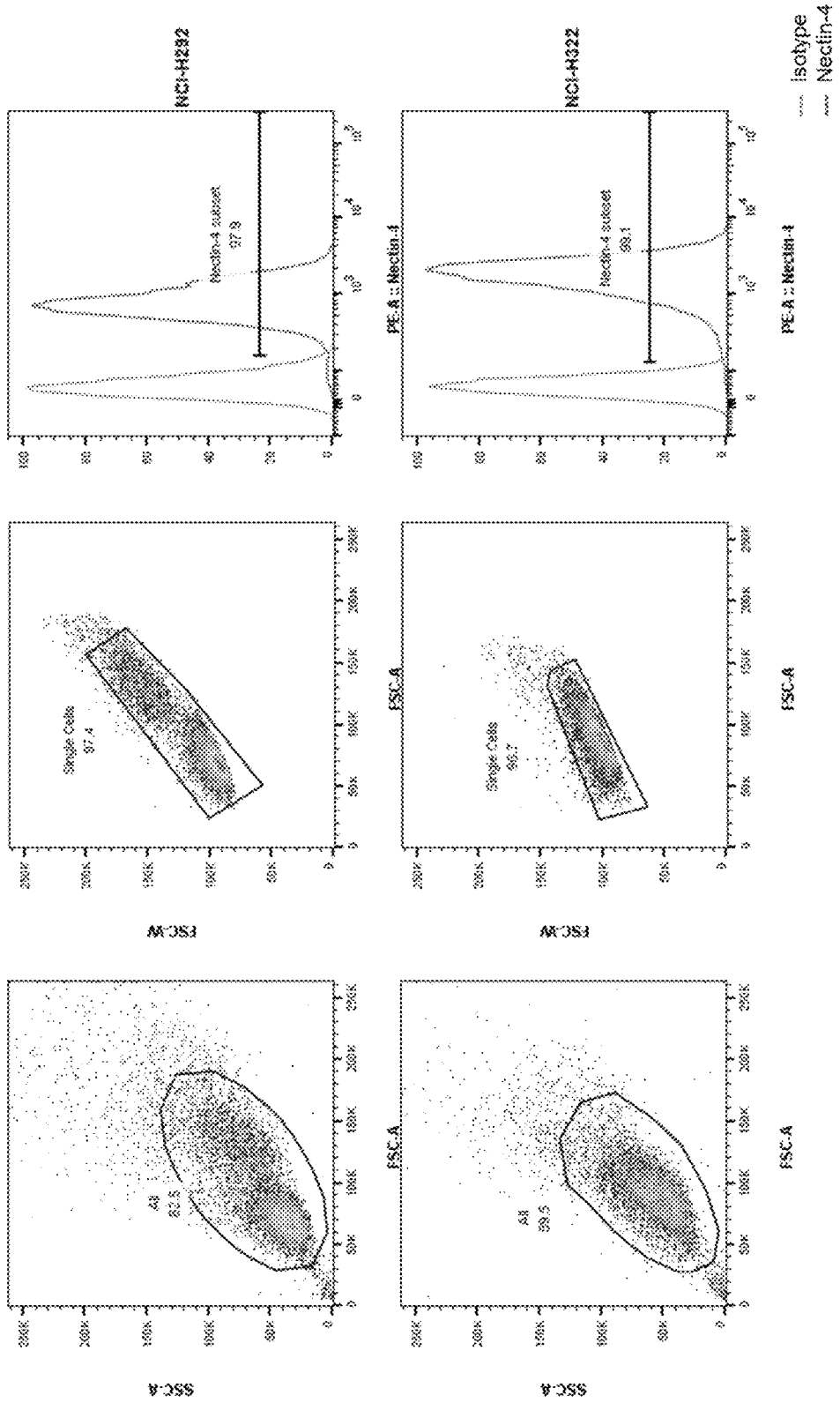
FIG. 9: Gating strategy for Nectin-4 in NCI-H292 and NCI-H322.
Figure 10:
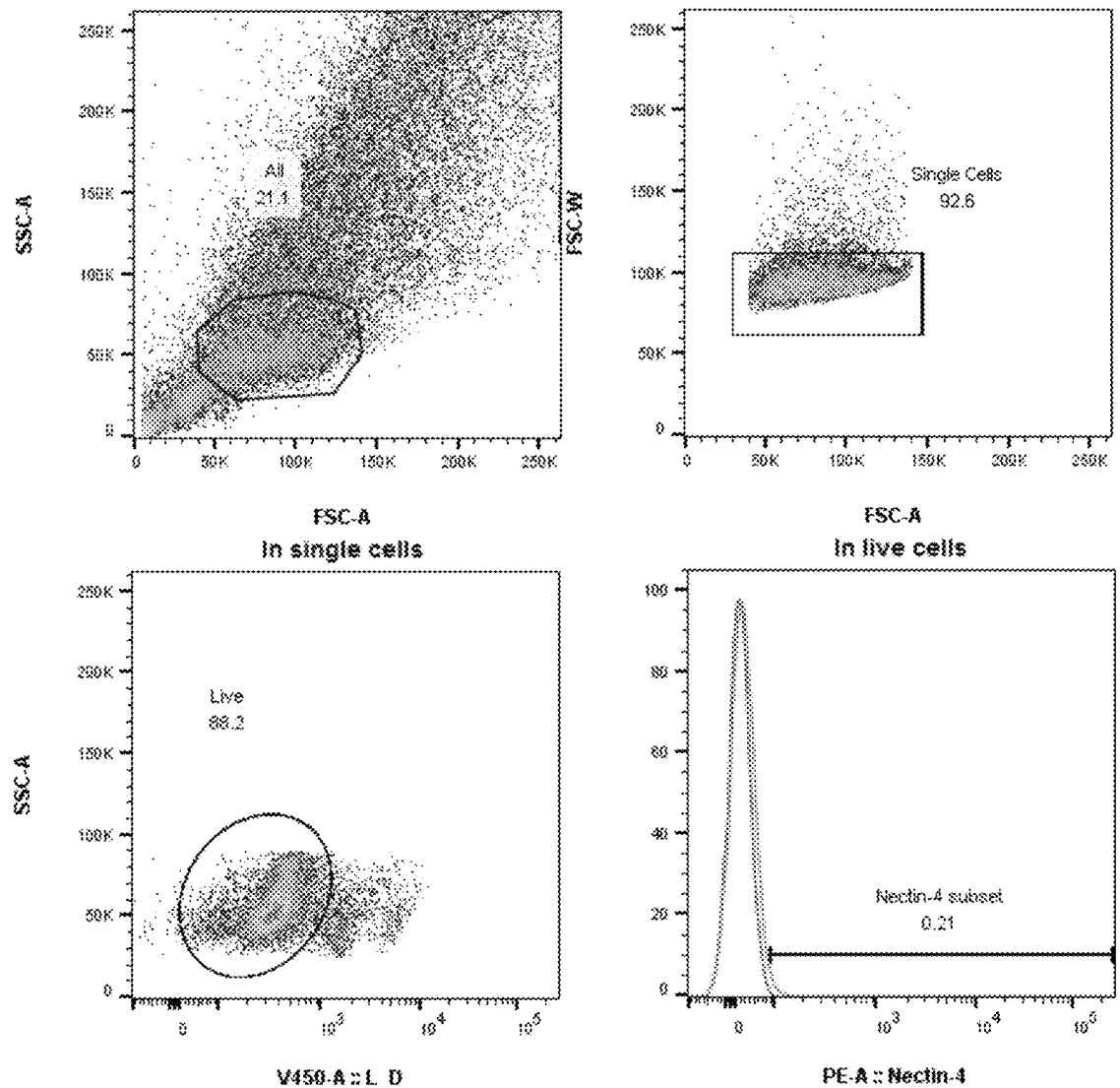
FIGS. 10 and 11: Gating strategy for Nectin-4 in NCI-H526 and HT1080, respectively.
Figure 11:
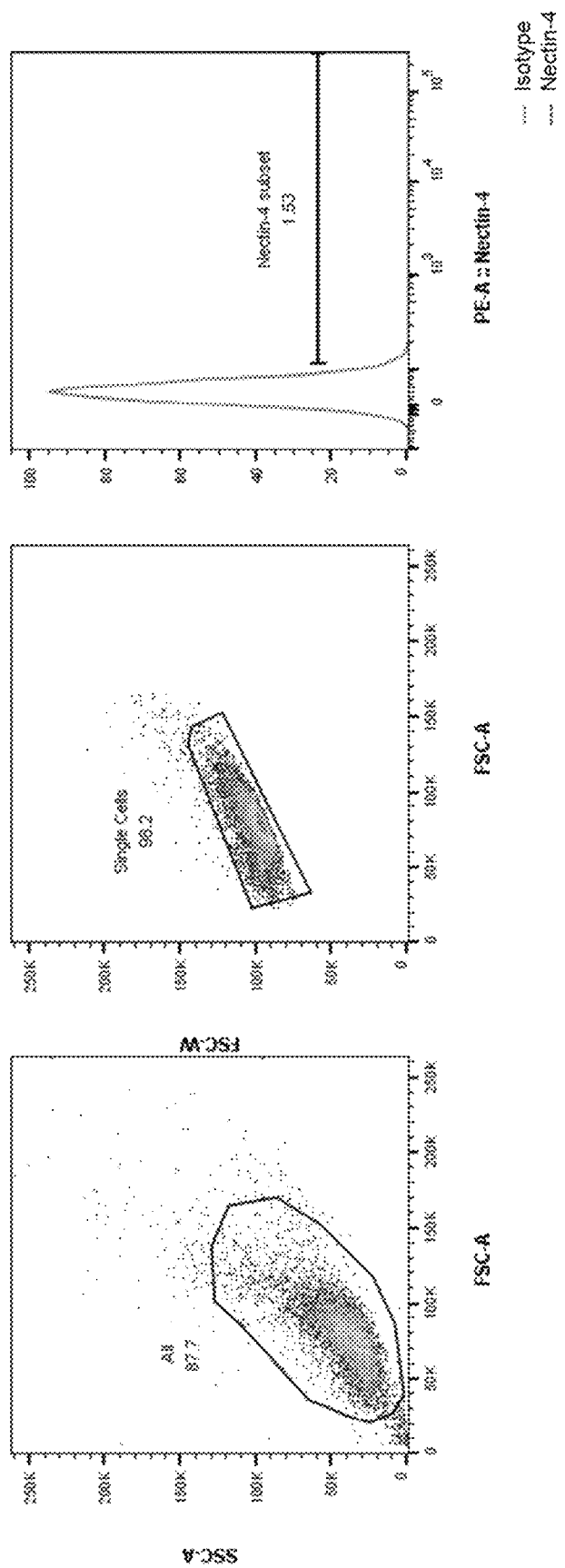
Figure 12:
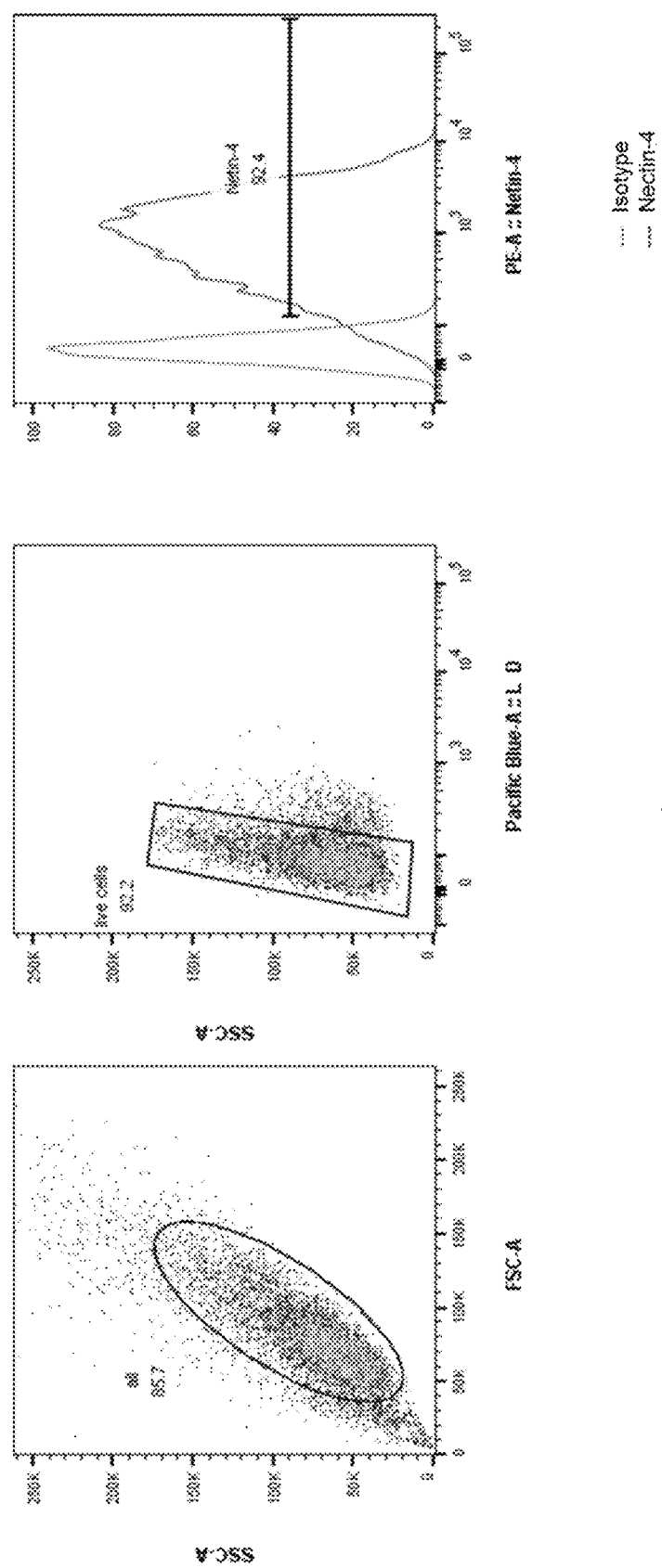
Figure 13:
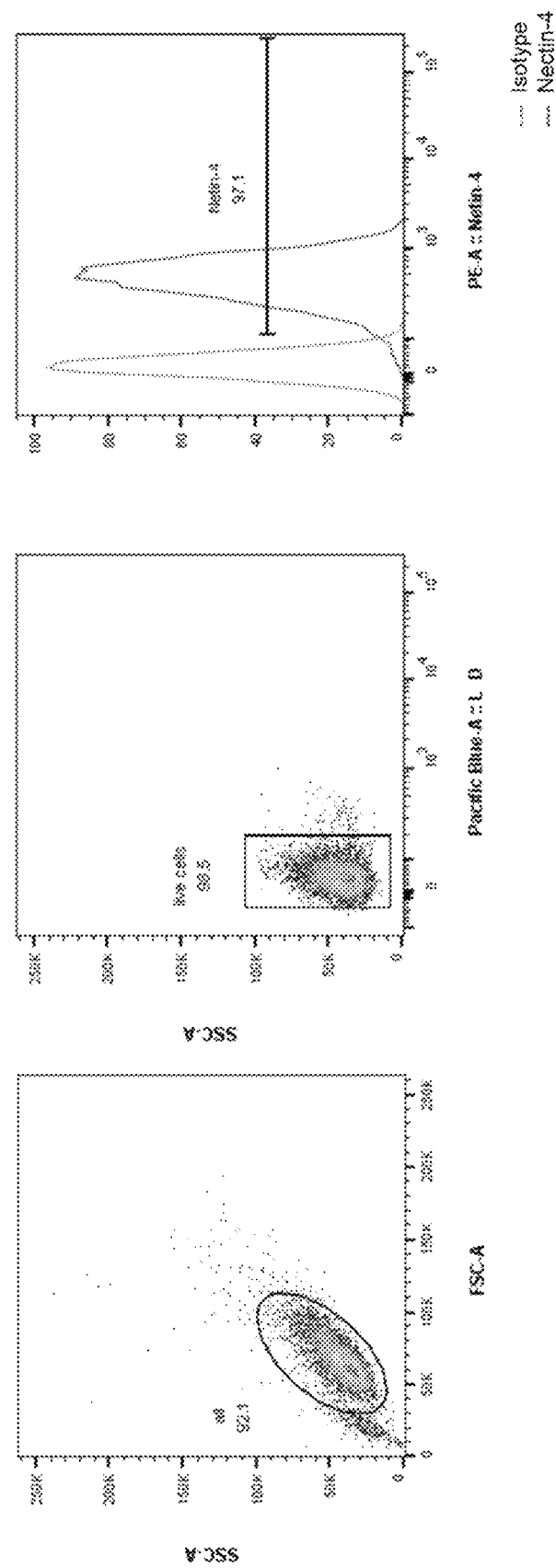
Figure 14A:
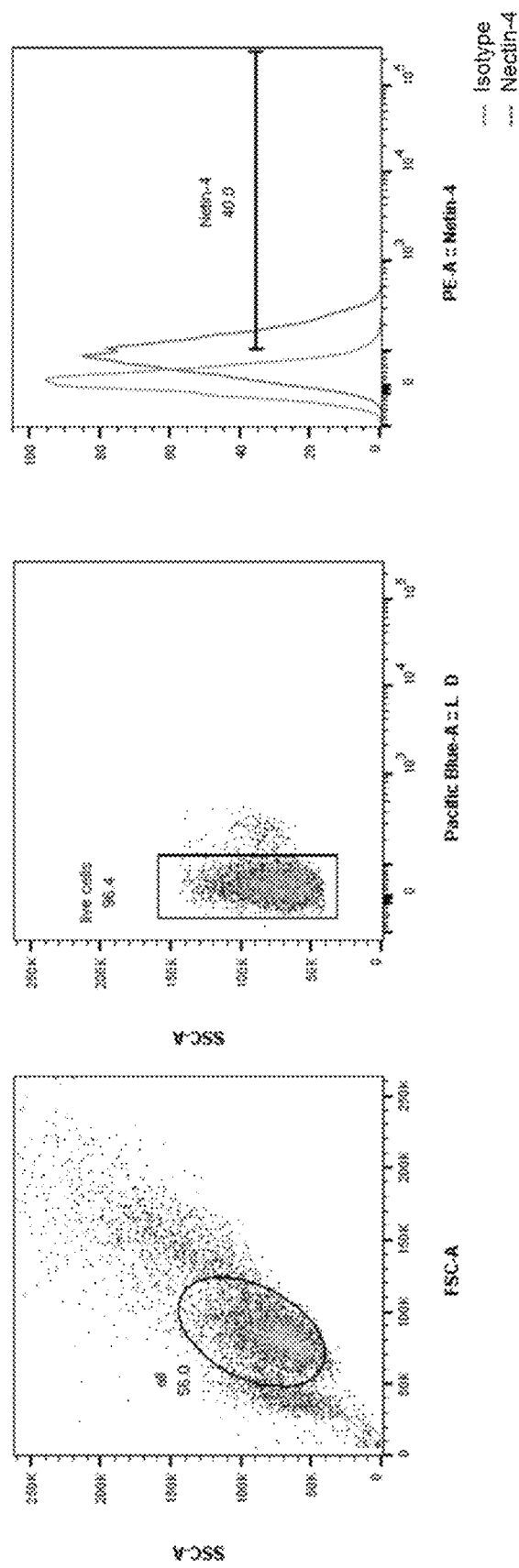
FIG. 14A and HCT-116.
Figure 14B:
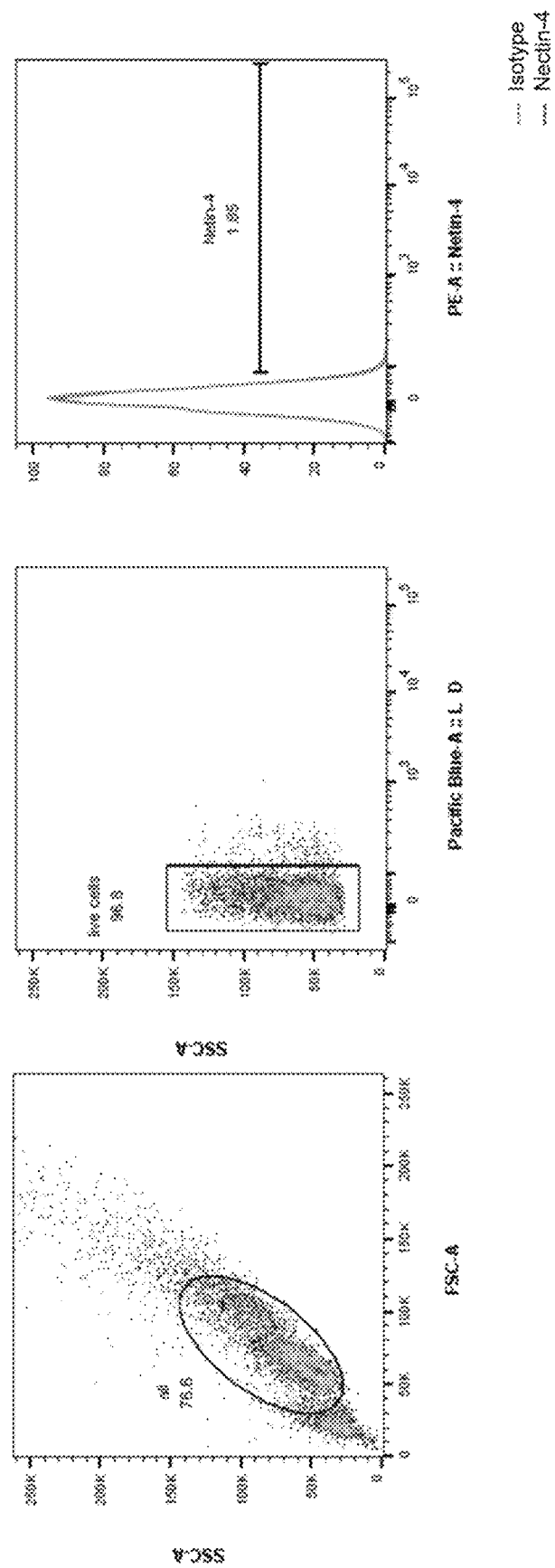
FIG. 14B), Lung cancer (A549.
Figure 15A:
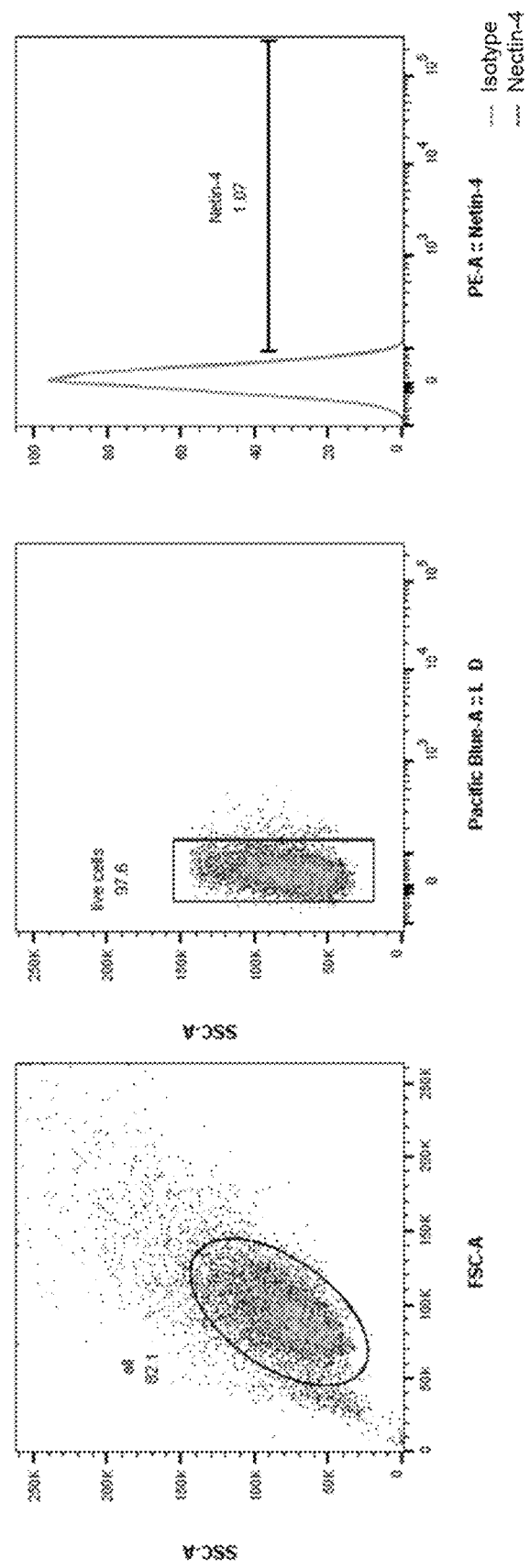
FIG. 15A, NCI-H292 and FIG. 15B, NCI-H358.
Figure 15B:
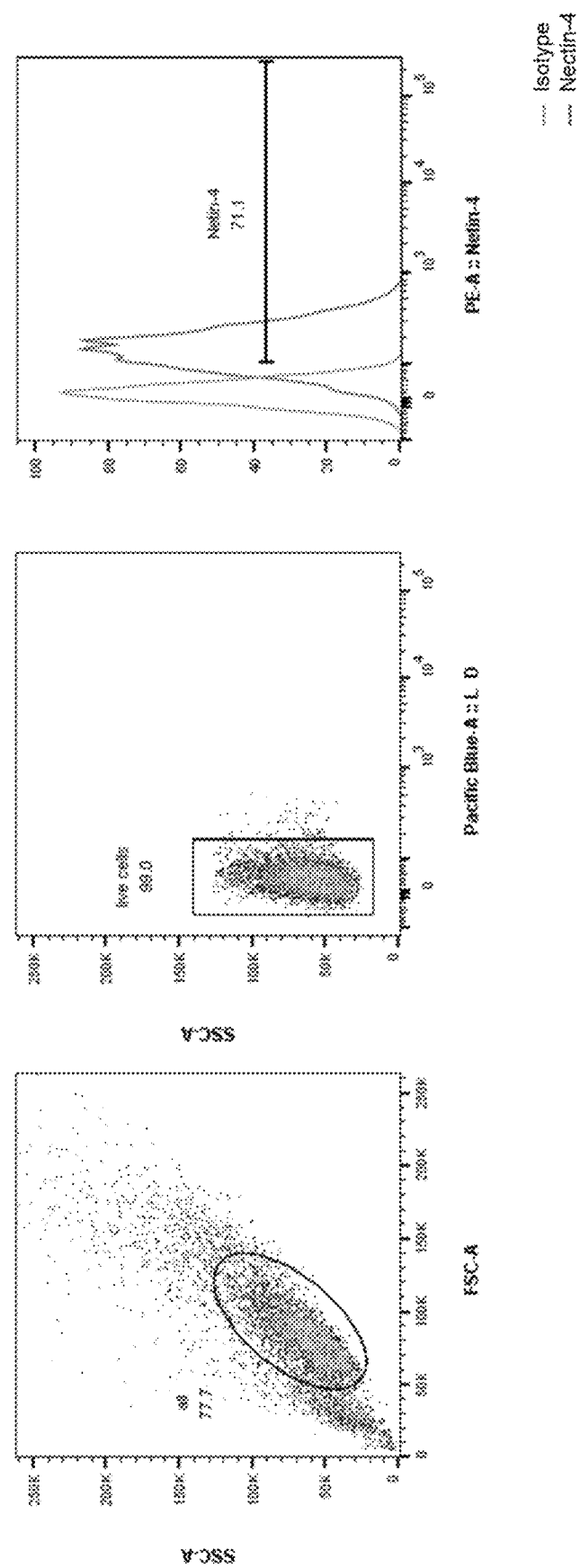
Figure 15C:
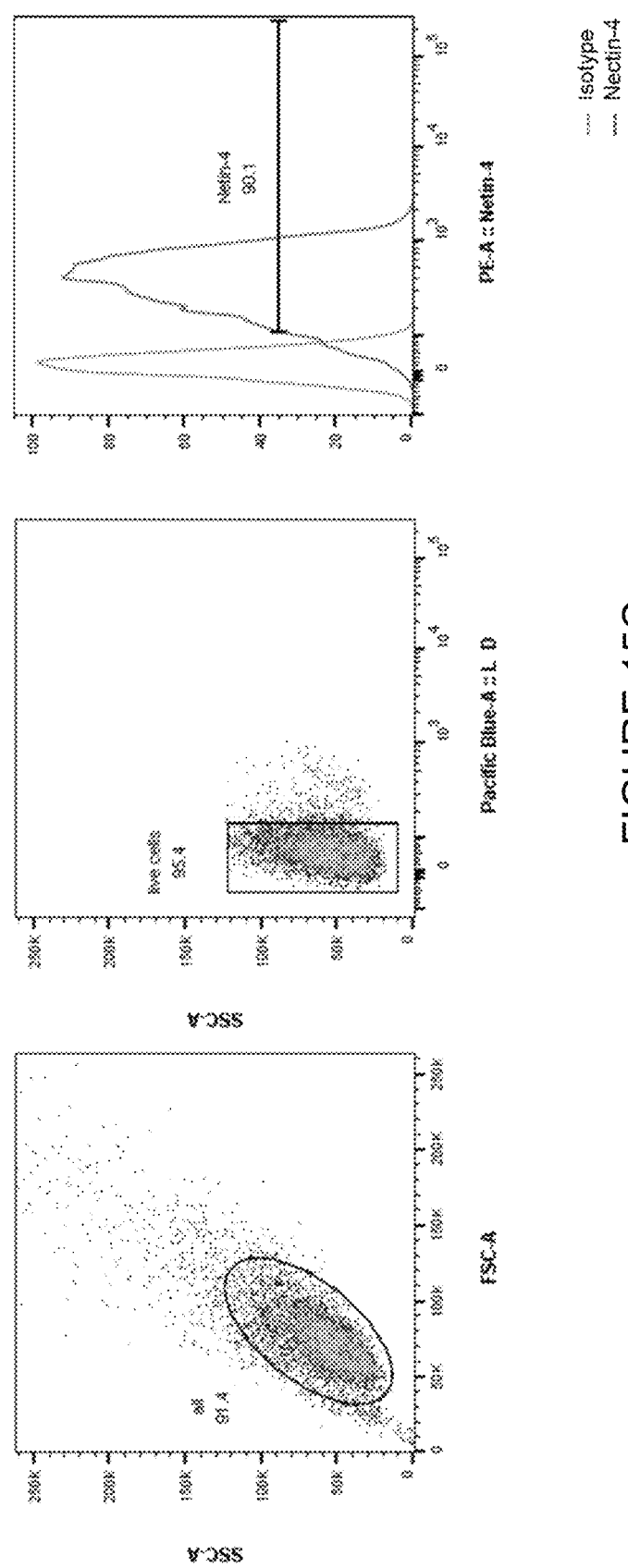
FIG. 15C and NCI-526.
Figure 15D:
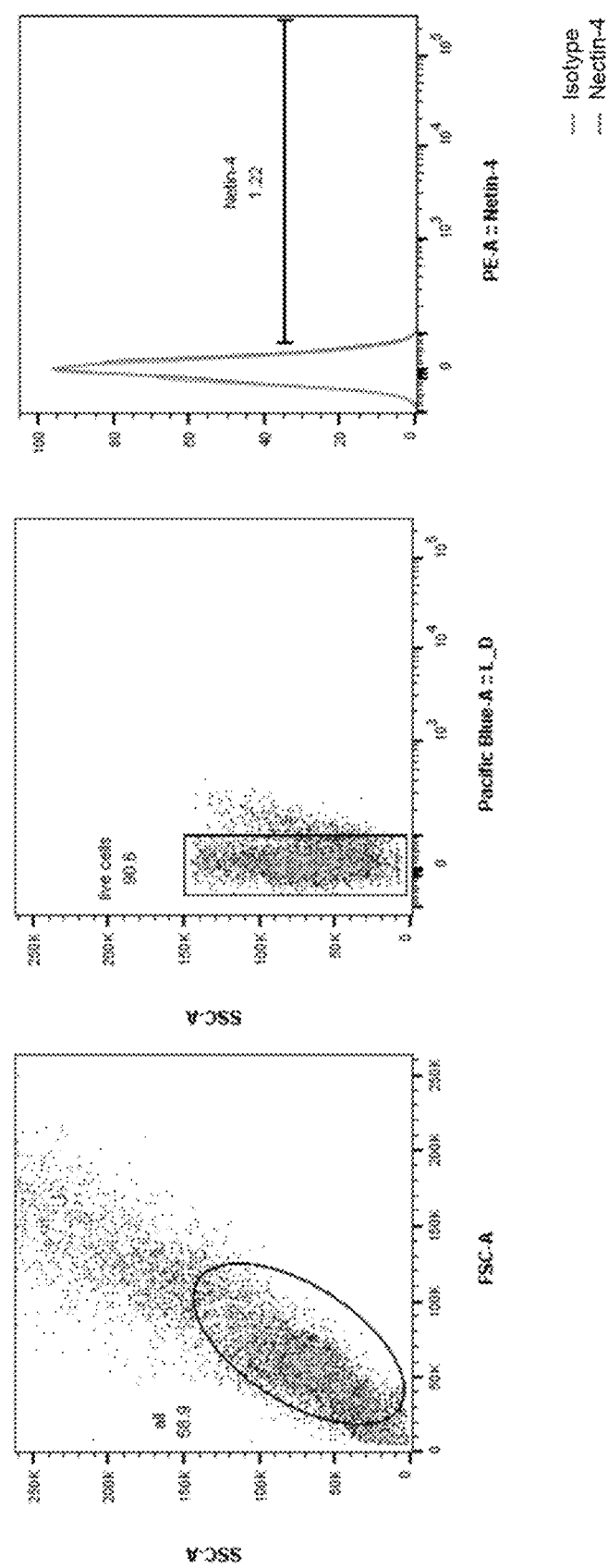
FIG. 15D), and Pancreas cancer (Panc02.13.
Figure 16:
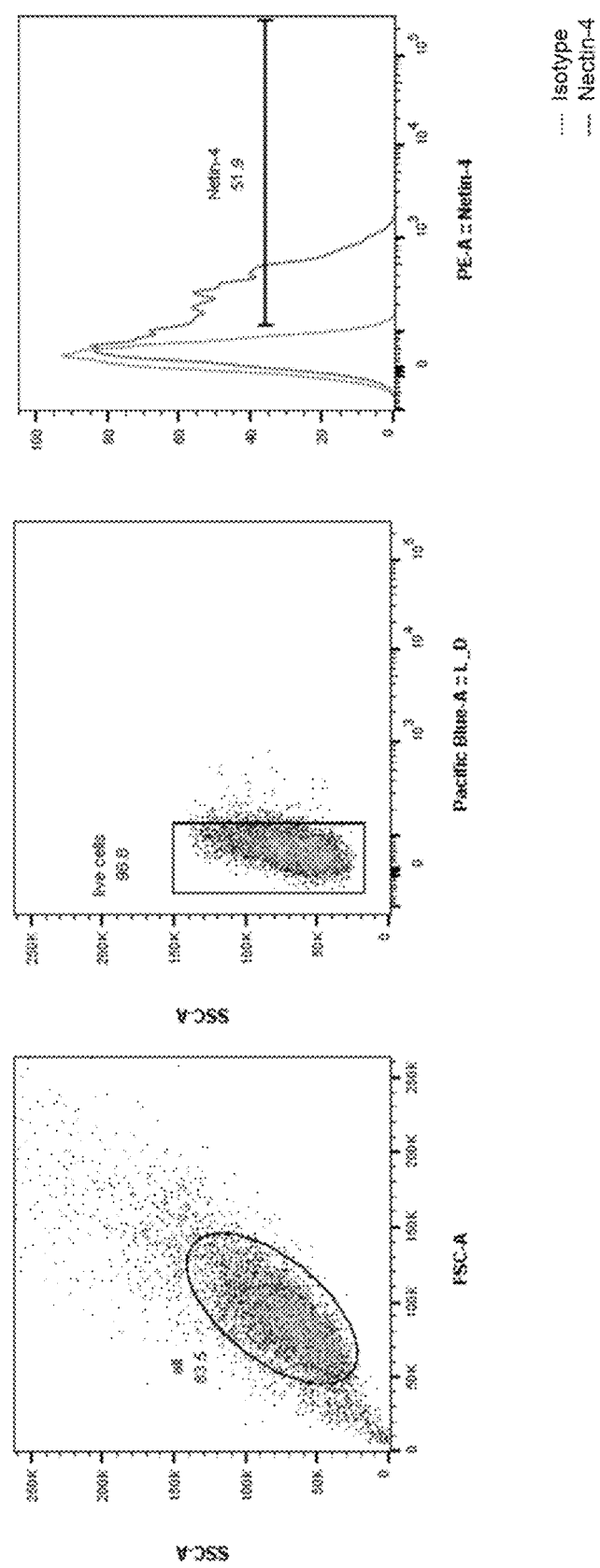

The tumor growth curve is shown in FIG. 7.

5.2 Tumor Volume Trace

Mean tumor volume over time in female Balb/c nude mice bearing NCI-H292 xenograft is shown in Table 17.

TABLE 17

Tumor volume trace over time

| | | Days after the start of treatment | | | | | | |
|---|---|---|---|---|---|---|---|---|
| Gr. | Treatment | 0 | 2 | 4 | 7 | 9 | 11 | 14 |
| 1 | Vehicle, qw | 168 ± 16 | 297 ± 48 | 362 ± 58 | 460 ± 62 | 548 ± 69 | 697 ± 102 | 843 ± 152 |
| 2 | BCY8549, 3 mpk, qw | 168 ± 30 | 187 ± 36 | 164 ± 31 | 205 ± 50 | 234 ± 57 | 240 ± 98 | 251 ± 66 |
| 3 | BCY8550, 3 mpk, qw | 167 ± 18 | 208 ± 21 | 237 ± 16 | 324 ± 35 | 421 ± 35 | 489 ± 44 | 545 ± 77 |
| 4 | BCY8783, 3 mpk, qw | 167 ± 28 | 182 ± 27 | 161 ± 40 | 137 ± 19 | 135 ± 22 | 97 ± 20 | 97 ± 19 |
| 5 | BCY8784, 3 mpk, qw | 167 ± 36 | 165 ± 28 | 111 ± 19 | 121 ± 12 | 123 ± 8 | 99 ± 10 | 94 ± 7 |

5.3 Tumor Growth Inhibition Analysis

Tumor growth inhibition rate for test articles in the NCI-H292 xenograft model was calculated based on tumor volume measurements at day 14 after the start of treatment. The measured tumor volume of all treatment groups at various time points are shown in FIG. 7 and Tables 17 and 18.

TABLE 18

Tumor growth inhibition analysis

| Gr | Treatment | Tumor Volume (mm$^3$)[a] | T/C[b] (%) | TGI (%) | P value |
|---|---|---|---|---|---|
| 1 | Vehicle, qw | 843 ± 152 | — | — | — |
| 2 | BCY8549, 3 mpk, qw | 251 ± 66 | 29.8 | 87.7 | p < 0.05 |

[a]Mean ± SEM.
[b]Tumor Growth Inhibition is calculated by dividing the group average tumor volume for the treated group by the group average tumor volume for the control group (T/C).

6. Results Summary and Discussion

In this study, the therapeutic efficacy of BCYs in the NCI-H292 xenograft model was evaluated. The measured tumor volume of all treatment groups at various time points are shown in FIG. 7 and Tables 17 and 18.

The mean tumor size of vehicle treated mice reached 843 mm$^3$ on day 14. BCY8549 at 3 mg/kg showed significant anti-tumor activity. In this study, all mice maintained body-weight well.

Example 6: Investigation of Association Between Copy Number Variation (CNV) and Gene Expression for Nectin-4 from Multiple Tumour Types Methods 1. Select all studies in cBioPortal (http://www.cbioportal.org/) and search for NECTIN4.
   (a) Remove provisional studies.
   (b) Deselect studies with overlapping samples to prevent sample bias (based on warning in cBioPortal)—always keep PanCancer study if this is an option.
   (c) Studies selected for analysis (Table 19).

TABLE 19

Studies analysed from cBioPortal and units in study

| Study Name | Units |
|---|---|
| Breast Cancer (METABRIC, Nature 2012 & Nat Commun 2016) | mRNA expression (microarray) |
| Breast Invasive Carcinoma (TCGA, PanCancer Atlas) | mRNA Expression Batch Normalized/Merged from Illumina HiSeq_RNASeqV2 syn4976369 |
| Uterine Corpus Endometrial Carcinoma (TCGA, PanCancer Atlas) | mRNA Expression Batch Normalized/Merged from Illumina HiSeq_RNASeqV2 syn4976369 |
| Bladder Urothelial Carcinoma (TCGA, PanCancer Atlas) | RSEM (Batch normalized from Illumina HiSeq_RNASeqV2) |
| Lung Adenocarcinoma (TCGA, PanCancer Atlas) | mRNA Expression, RSEM (Batch normalized from HiSeq_RNASeqV2) |
| Cervical Squamous Cell Carcinoma (TCGA, PanCancer Atlas) | RSEM (Batch normalized from Illumina HiSeq_RNASeqV2) |
| Lung Squamous Cell Carcinoma (TCGA, PanCancer Atlas) | mRNA Expression Batch Normalized/Merged from Illumina HiSeq_RNASeqV2 syn4976369 |
| Head and Neck Squamous Cell Carcinoma (TCGA, PanCancer Atlas) | mRNA Expression, RSEM (Batch normalized from HiSeq_RNASeqV2) |
| Pancreatic Adenocarcinoma (TCGA, PanCancer Atlas) | mRNA Expression Batch Normalized/Merged from Illumina HiSeq_RNASeqV2 syn4976369 |
| Thyroid Carcinoma (TCGA, PanCancer Atlas) | mRNA Expression Batch Normalized/Merged from Illumina HiSeq_RNASeqV2 syn4976369 |
| Colon Adenocarcinoma (TCGA, PanCancer Atlas) | RSEM (Batch normalized from Illumina HiSeq_RNASeqV2) |
| Thymoma (TCGA, PanCancer Atlas) | mRNA Expression Batch Normalized/Merged from Illumina HiSeq_RNASeqV2 syn4976369 |
| Sarcoma (TCGA, PanCancer Atlas) | mRNA Expression Batch Normalized/Merged from Illumina HiSeq_RNASeqV2 syn4976369 |
| Stomach Adenocarcinoma (TCGA, PanCancer Atlas) | mRNA Expression Batch Normalized/Merged from Illumina HiSeq_RNASeqV2 syn4976369 |

TABLE 19-continued

Studies analysed from cBioPortal and units in study

| Study Name | Units |
| --- | --- |
| Prostate Adenocarcinoma (TCGA, PanCancer Atlas) | mRNA Expression, RSEM (Batch normalized from Illumina HiSeq_RNASeqV2) |
| Kidney Chromophobe (TCGA, PanCancer Atlas) | mRNA Expression, RSEM (Batch normalized from Illumina HiSeq_RNASeqV2) |
| Rectum Adenocarcinoma (TCGA, PanCancer Atlas) | mRNA Expression Batch Normalized/Merged from Illumina HiSeq_RNASeqV2 syn4976369 |
| Metastatic Prostate Cancer, SU2C/PCF Dream Team (Robinson et al., Cell 2015) | mRNA expression/capture (RNA Seq RPKM) |
| Pheochromocytoma and Paraganglioma (TCGA, PanCancer Atlas) | mRNA Expression Batch Normalized/Merged from Illumina HiSeq_RNASeqV2 syn4976369 |
| Kidney Renal Clear Cell Carcinoma (TCGA, PanCancer Atlas) | mRNA Expression, RSEM (Batch normalized from Illumina HiSeq_RNASeqV2) |
| Prostate Adenocarcinoma (Fred Hutchinson CRC, Nat Med 2016) | mRNA expression |
| Colorectal Adenocarcinoma (TCGA, Nature 2012) | RNA Seq RPKM |
| Ovarian Serous Cystadenocarcinoma (TCGA, PanCancer Atlas) | mRNA Expression Batch Normalized/Merged from Illumina HiSeq_RNASeqV2 syn4976369 |
| Kidney Renal Papillary Cell Carcinoma (TCGA, PanCancer Atlas) | mRNA Expression, RSEM (Batch normalized from Illumina HiSeq_RNASeqV2) |
| Brain Lower Grade Glioma (TCGA, PanCancer Atlas) | RSEM (Batch normalized from Illumina HiSeq_RNASeqV2) |
| Esophageal Adenocarcinoma (TCGA, PanCancer Atlas) | RSEM (Batch normalized from Illumina HiSeq_RNASeqV2) |
| Adrenocortical Carcinoma (TCGA, PanCancer Atlas) | RSEM (Batch normalized from Illumina HiSeq_RNASeqV2) |
| Glioblastoma Multiforme (TCGA, PanCancer Atlas) | mRNA Expression, RSEM (Batch normalized from Illumina HiSeq_RNASeqV2) |
| Prostate Adenocarcinoma (MSKCC, Cancer Cell 2010) | mRNA Expression |
| Uterine Carcinosarcoma (TCGA, PanCancer Atlas) | mRNA Expression Batch Normalized/Merged from Illumina HiSeq_RNASeqV2 syn4976369 |
| Acute Myeloid Leukemia (TCGA, PanCancer Atlas) | mRNA Expression, RSEM (Batch normalized from Illumina HiSeq_RNASeqV2) |
| Skin Cutaneous Melanoma (TCGA, PanCancer Atlas) | mRNA Expression Batch Normalized/Merged from Illumina HiSeq_RNASeqV2 syn4976369 |
| Mesothelioma (TCGA, PanCancer Atlas) | mRNA Expression Batch Normalized/Merged from Illumina HiSeq_RNASeqV2 syn4976369 |
| Cholangiocarcinoma (TCGA, PanCancer Atlas) | RSEM (Batch normalized from Illumina HiSeq_RNASeqV2) |
| Pediatric Acute Lymphoid Leukemia - Phase II (TARGET, 2018) | NECTIN4: mRNA expression (RNA-Seq RPKM) |
| Diffuse Large B-Cell Lymphoma (TCGA, PanCancer Atlas) | mRNA Expression, RSEM (Batch normalized from Illumina HiSeq_RNASeqV2) |
| Cancer Cell Line Encyclopedia (Novartis/Broad, Nature 2012) | mRNA expression (microarray) |
| Uveal Melanoma (TCGA, PanCancer Atlas) | mRNA Expression Batch Normalized/Merged from Illumina HiSeq_RNASeqV2 syn4976369 |
| Pediatric Wilms' Tumor (TARGET, 2018) | NECTIN4: mRNA expression (RNA-Seq RPKM) |
| Testicular Germ Cell Tumors (TCGA, PanCancer Atlas) | mRNA Expression Batch Normalized/Merged from Illumina HiSeq_RNASeqV2 syn4976369 |
| Liver Hepatocellular Carcinoma (TCGA, PanCancer Atlas) | NECTIN4: mRNA Expression, RSEM (Batch normalized from Illumina HiSeq_RNASeqV2) |

2. Export CNV and RNA expression data from cBioPortal.
3. Test if CNVs are statistically significantly associated with changes in mRNA expression for Nectin-4 (log 2 not applied).
   (a) Run non-parametric Kruskal-Wallis test in GraphPad Prism (7.04) and R/R studio (threshold for significance: $p<0.01$).
      (i) GraphPad Prism: set up column table, run non-parametric test with no matching or pairing and do not assume Gaussian distribution.
      (ii) Packages used in R:
         1. XLConnect
         2. dplyr
         3. Kruskal-Wallis Rank Sum Test: Kruskal.test.
4. Adjust for multiple comparisons (include all possible comparisons even if n=1 within a group) in R/Rstudio using Dunn's test (threshold for significance: $p<0.025$).
   (a) dunn.test with multiple comparison method="bonferonni".

Results

The results are shown in Table 20 below. Across 41 publicly available TCGA datasets that report both tumor CNV and mRNA gene expression data for Nectin-4, there are many indications where cases have been reported with either Nectin-4 copy number gains (2-3 copies) or amplifications (>3 copies). In addition, separate cases have been demonstrated to have shallow deletions (<2 copies) with rare reports of tumors containing deep deletions consistent with greater than 1 copy loss or biallelic Nectin-4 loss. Indications where amplifications were detected most frequently were breast cancer (10-22%), bladder cancer (20%), lung cancer (5-7%) and hepatocellular carcinoma (8%). Indications with most frequent copy number losses were kidney chromophobe (77%), renal clear cell carcinoma (RCC) (6.5%), sarcoma (10%), colon cancer (10%), head and neck cancer (7%) and lung squamous cancer. These data indicate that there are a range of CNV within and across tumor indications and a diversity of copy number patterns across different indications.

In addition to CNVs within the TCGA dataset the median Nectin-4 mRNA expression level per indication covers approximately $2^{10}$ range. Therefore, given the range of Nectin-4 mRNA expression levels and the CNVs observed across and within tumor types statistical testing was performed to identify potential associations between Nectin-4 mRNA levels and Nectin-4 CNVs within individual TCGA datasets/indications. Tumors per indication were allocated to 1 of 5 classes:
  a) Deep deletion;
  b) Shallow deletion;
  c) Diploid;
  d) Gain; or
  e) Amplification.

Kruskall-Wallis testing was then performed to detect if the distributions of mRNA expression values per classes differed between classes (P<0.01). For those TCGA data sets with P<0.01 and to identify which classes were different to one another post hoc testing was performed by calculating Z-statistics with adjusted P-values calculated (Bonferonni). For simplicity of interpretation pair-wise comparisons vs. diploid per indication were reviewed (although all pair-wise P-values were calculated). 18/41 TCGA studies met Kruskall-Wallis P<0.01 & Bonferonni P<0.025 for Gain vs. Diploid and/or Amplification vs. Diploid comparisons indicating an association of increased Nectin-4 mRNA expression with increased Nectin-4 copy number. These 18 studies represented 14 independent tumor histologies:
  breast, uterine, bladder, lung adenocarcinoma, lung squamous, cervical, head and neck, pancreatic, thyroid, colorectal, thymoma, sarcoma, renal clear cell carcinoma (RCC) and stomach.

In addition, 6 studies have decreased mRNA expression associated with copy number loss. Four of these six studies not only showed an association between CNV loss and reduced expression, but also reported CNV gains associated with high expression:
  stomach, lung squamous, colon and thyroid.

Whereas two indications, kidney chromophobe and prostate cancer only reported associations with CNV loss and low transcript abundance. Additionally, there was a separate prostate cancer study (Metastatic Prostate Cancer, SU2C/PCF Dream Team (Robinson et al., Cell 2015)) that showed copy number gains associated with high expression (relative to diploid).

These observations of tumor CNV loss and gain with mRNA expression levels may represent the mechanism behind Nectin-4 tumor protein expression in those indications where such associations were observed. Clearly there are indications where CNVs do not appear to impact mRNA expression levels in a predictable pattern such as hepatocellular carcinoma. In vivo preclinical efficacy with certain Nectin-4 bicyclic drug conjugates of the invention has been demonstrated to correlate with Nectin-4 protein expression as measured by IHC. Therefore, if tumor Nectin-4 CNVs associate with mRNA levels and predict protein expression levels it is formally possible that patients with tumors containing copy number increases (gain or amplification) may be more likely to respond to Nectin-4 bicyclic drug conjugates of the invention. If patients could be identified with increased CNV in Nectin-4 then this information could be used to select patients for treatment with Nectin-4 bicyclic drug conjugates of the invention.

TABLE 20

Results of Investigation of Association between Copy Number Variation (CNV) and gene expression for Nectin-4

| Study name | Units | Number of samples/group (n = X) | | | | | Kruskal-Wallis Test | | Pairwise Comparison, Z statistic (adjusted p-value), Bonferonni | | |
|---|---|---|---|---|---|---|---|---|---|---|---|
| | | Deep deletion | Shallow deletion | Diploid | Gain | Amplification | Kruskal-Wallis Statistic | p-value | Deep Deletion - Diploid | Diploid - Shallow deletion | Diploid - Gain | Amplification - Diploid |
| Breast Cancer (METABRIC, Nature 2012 & Nat Commun 2016) | mRNA expression (microarray) | 0 | 11 | 745 | 706 | 404 | 380.4 | <2.2e-16 | N/A | 0.568782 (1.0000) | -11.89096 (0.0000)* | 18.85085 (0.0000)* |
| Breast Invasive Carcinoma (TCGA, PanCancer Atlas) | mRNA Expression Batch Normalized/Merged from Illumina HiSeq_RNASeq V2 syn4976369 | 0 | 13 | 244 | 640 | 97 | 219.5 | <2.2e-16 | N/A | 1.186089 (0.7068) | -12.30176 (0.0000)* | 12.07432 (0.0000)* |
| Uterine Corpus Endometrial Carcinoma (TCGA, PanCancer Atlas) | mRNA Expression Batch Normalized/Merged from Illumina HiSeq_RNASeq V2 syn4976369 | 0 | 5 | 274 | 210 | 18 | 76.392 | <2.2e-16 | N/A | 1.130854 (0.7743) | -7.274308 (0.0000*) | 5.601260 (0.0000)* |
| Bladder Urothelial Carcinoma (TCGA, PanCancer Atlas) | RSEM (Batch normalized from Illumina HiSeq_RNASeq V2) | 0 | 16 | 171 | 145 | 70 | 67.078 | 1.80E-14 | N/A | 0.060907 (1.0000) | -3.323839 (0.0027)* | 8.054269 (0.0000)* |
| Lung Adenocarcinoma (TCGA, PanCancer Atlas) | mRNA Expression, RSEM (Batch normalized from Illumina HiSeq_RNASeq V2) | 0 | 9 | 129 | 332 | 33 | 59.578 | 7.24E-13 | N/A | 0.237200 (1.0000) | -6.244156 (0.0000)* | 6.247228 (0.0000)* |
| Cervical Squamous Cell Carcinoma (TCGA, PanCancer Atlas) | RSEM (Batch normalized from Illumina HiSeq_RNASeq V2) | 0 | 7 | 115 | 147 | 6 | 51.372 | 4.08E-11 | N/A | 1.093749 (0.8222) | -6.170067 (0.0000)* | 3.815296 (0.0004)* |

TABLE 20-continued

Results of Investigation of Association between Copy Number Variation (CNV) and gene expression for Nectin-4

| Study name | Units | Number of samples/group (n = X) | | | | | Knuskal-Wallis Test | | Pairwise Comparison, Z statistic (adjusted p-value), Bonferonni | | |
|---|---|---|---|---|---|---|---|---|---|---|---|
| | | Deep deletion | Shallow deletion | Diploid | Gain | Amplification | Knuskal-Wallis Statistic | p-value | Deep Deletion - Diploid | Diploid - Shallow deletion | Diploid - Gain | Amplification - Diploid |

| Study name | Units | Deep deletion | Shallow deletion | Diploid | Gain | Amplification | KW Statistic | p-value | Deep Deletion - Diploid | Diploid - Shallow deletion | Diploid - Gain | Amplification - Diploid |
|---|---|---|---|---|---|---|---|---|---|---|---|---|
| Lung Squamous Cell Carcinoma (TCGA, PanCancer Atlas) | mRNA Expression Batch Normalized/Merged from Illumina HiSeq_RNASeq V2 syn4976369 | 0 | 22 | 199 | 222 | 23 | 42.128 | 3.77E-09 | N/A | 2.819759 (0.0144)* | -3.034709 (0.0072)* | 4.860629 (0.0000)* |
| Head and Neck Squamous Cell Carcinoma (TCGA, PanCancer Atlas) | mRNA Expression, RSEM (Batch normalized from Illumina HiSeq_RNASeq V2) | 0 | 32 | 330 | 122 | 4 | 37.81 | 3.10E-08 | N/A | 1.736867 (0.2472) | -4.848550 (0.0000)* | 3.033083 (0.0073)* |
| Pancreatic Adenocarcinoma (TCGA, PanCancer Atlas) | mRNA Expression Batch Normalized/Merged from Illumina HiSeq_RNASeq V2 syn4976369 | 0 | 7 | 105 | 50 | 6 | 36.863 | 4.92E-08 | N/A | 1.333193 (0.5474) | -4.388701 (0.0000)* | 4.166401 (0.0001)* |
| Thyroid Carcinoma (TCGA, PanCancer Atlas) | mRNA Expression Batch Normalized/Merged from Illumina HiSeq_RNASeq V2 syn4976369 | 0 | 3 | 451 | 26 | 0 | 31.882 | 1.19E-07 | N/A | 2.486724 (0.0193)* | -5.021279 (0.0000)* | N/A |
| Colon Adenocarcinoma (TCGA, PanCancer Atlas) | RSEM (Batch normalized from Illumina HiSeq_RNASeq V2) | 0 | 40 | 266 | 80 | 2 | 31.309 | 7.32E-07 | N/A | 3.811621 (0.0004)* | -2.987223 (0.0084)* | 1.759508 (0.2355) |
| Thymoma (TCGA, PanCancer Atlas) | mRNA Expression Batch Normalized/Merged from Illumina HiSeq_RNASeq V2 syn4976369 | 0 | 0 | 95 | 22 | 2 | 26.213 | 2.03E-06 | N/A | N/A | -4.962115 (0.0000)* | 1.567541 (0.1755) |

TABLE 20-continued

Results of Investigation of Association between Copy Number Variation (CNV) and gene expression for Nectin-4

| Study name | Units | Number of samples/group (n = X) | | | | | Kruskal-Wallis Test | | Pairwise Comparison, Z statistic (adjusted p-value), Bonferonni | | | |
|---|---|---|---|---|---|---|---|---|---|---|---|---|
| | | Deep deletion | Shallow deletion | Diploid | Gain | Amplification | Kruskal-Wallis Statistic | p-value | Deep Deletion - Diploid | Diploid - Shallow deletion | Diploid - Gain | Amplification - Diploid |
| Sarcoma (TCGA, PanCancer Atlas) | mRNA Expression Batch Normalized/Merged from Illumina HiSeq_RNASeq V2 syn4976369 | 0 | 22 | 120 | 74 | 14 | 26.831 | 6.39E-06 | N/A | -0.410850 (1.0000) | -4.582047 (0.0000)* | 3.106262 (0.0057)* |
| Stomach Adenocarcinoma (TCGA, PanCancer Atlas) | mRNA Expression Batch Normalized/Merged from Illumina HiSeq_RNASeq V2 syn4976369 | 0 | 11 | 253 | 134 | 9 | 19.096 | 0.0002611 | N/A | 2.835658 (0.0137)* | -2.921683 (0.0104)* | -0.265333 (1.0000) |
| Prostate Adenocarcinoma (TCGA, PanCancer Atlas) | mRNA Expression, RSEM (Batch normalized from Illumina HiSeq_RNASeq V2) | 3 | 15 | 437 | 29 | 3 | 19.125 | 0.0007426 | -2.532734 (0.0566) | 3.202764 (0.0068)* | -1.351661 (0.8824) | 0.509151 (1.0000) |
| Kidney Chromophobe (TCGA, PanCancer Atlas) | mRNA Expression, RSEM (Batch normalized from Illumina HiSeq_RNASeq V2) | 0 | 50 | 14 | 1 | 0 | 13.851 | 0.0009823 | N/A | 3.609735 (0.0005)* | -0.058395 (1.0000) | N/A |
| Rectum Adenocarcinoma (TCGA, PanCancer Atlas) | mRNA Expression Batch Normalized/Merged from Illumina HiSeq_RNASeq V2 syn4976369 | 0 | 11 | 91 | 33 | 1 | 14.056 | 0.00283 | N/A | 1.050760 (0.8801) | -2.951363 (0.0095)* | 1.809506 (0.2111) |
| Metastatic Prostate Cancer, SU2C/PCF Dream Team (Robinson et al., Cell 2015) | mRNA expression/capture (RNA Seq RPKM) | 0 | 3 | 75 | 37 | 2 | 12.336 | 0.006317 | N/A | 0.040058 (1.0000) | -3.420479 (0.0019)* | -0.362109 (1.0000) |

TABLE 20-continued

Results of Investigation of Association between Copy Number Variation (CNV) and gene expression for Nectin-4

| Study name | Units | Number of samples/group (n = X) | | | | | Kruskal-Wallis Test | | Pairwise Comparison, Z statistic (adjusted p-value), Bonferonni | | | |
|---|---|---|---|---|---|---|---|---|---|---|---|---|
| | | Deep deletion | Shallow deletion | Diploid | Gain | Amplification | Kruskal-Wallis Statistic | p-value | Deep Deletion - Diploid | Diploid - Shallow deletion | Diploid - Gain | Amplification - Diploid |
| Pheochromocytoma and Paraganglioma (TCGA, PanCancer Atlas) | mRNA Expression Batch Normalized/Merged from Illumina HiSeq_RNASeq V2 syn4976369 | 0 | 14 | 123 | 19 | 5 | 11.573 | 0.008998 | N/A | -1.271308 (0.6109) | -2.597791 (0.0281) | 2.201970 (0.0830) |
| Kidney Renal Clear Cell Carcinoma (TCGA, PanCancer Atlas) | mRNA Expression, RSEM (Batch normalized from Illumina HiSeq_RNASeq V2) | 0 | 22 | 297 | 32 | 1 | 11.314 | 0.01014 | N/A | -0.748380 (1.0000) | -2.996852 (0.0082)* | 1.502464 (0.3989)* |
| Prostate Adenocarcinoma (Fred Hutchinson CRC, Nat Med 2016) | mRNA expression | 0 | 1 | 59 | 66 | 7 | 9.8842 | 0.01958 | N/A | 0.677737 (1.0000) | -0.409530 (1.0000) | 3.028793 (0.0074)* |
| Colorectal Adenocarcinoma (TCGA, Nature 2012) | RNA Seq RPKM | 0 | 4 | 153 | 34 | 2 | 9.4054 | 0.02 | N/A | 0.062894 (1.0000) | -1.860678 (0.1884) | 2.514653 (0.0357) |
| Ovarian Serous Cystadenocarcinoma (TCGA, PanCancer Atlas) | mRNA Expression Batch Normalized/Merged from Illumina HiSeq_RNASeq V2 syn4976369 | 0 | 7 | 75 | 117 | 2 | 9.3101 | 0.02544 | N/A | 1.589035 (0.3362) | -2.168253 (0.0904) | 0.062706 (1.0000) |
| Kidney Renal Papillary Cell Carcinoma (TCGA, PanCancer Atlas) | mRNA Expression, RSEM (Batch normalized from Illumina HiSeq_RNASeq V2) | 1 | 19 | 239 | 15 | 0 | 9.1134 | 0.02782 | 1.607764 (0.3237) | -0.569938 (1.0000) | -2.552083 (0.0321) | N/A |
| Brain Lower Grade Glioma (TCGA, PanCancer Atlas) | RSEM (Batch normalized from Illumina HiSeq_RNASeq V2) | 0 | 11 | 462 | 32 | 2 | 4.769 | 0.1895 | N/A | 0.462462 (1.0000) | -1.718955 (0.2569) | 1.261960 (0.6209) |

TABLE 20-continued

Results of Investigation of Association between Copy Number Variation (CNV) and gene expression for Nectin-4

| Study name | Units | Number of samples/group (n = X) | | | | | Kruskal-Wallis Test | | Pairwise Comparison, Z statistic (adjusted p-value), Bonferonni | | | |
|---|---|---|---|---|---|---|---|---|---|---|---|---|
| | | Deep deletion | Shallow deletion | Diploid | Gain | Amplification | Kruskal-Wallis Statistic | p-value | Deep Deletion - Diploid | Diploid - Shallow deletion | Diploid - Gain | Amplification - Diploid |
| Esophageal Adenocarcinoma (TCGA, PanCancer Atlas) | RSEM (Batch normalized from Illumina HiSeq_RNASeq V2) | 0 | 8 | 78 | 86 | 9 | 4.267 | 0.234 | N/A | 0.747441 (1.0000) | −0.768855 (1.0000) | 1.756911 (0.2368) |
| Adrenocortical Carcinoma (TCGA, PanCancer Atlas) | RSEM (Batch normalized from Illumina HiSeq_RNASeq V2) | 0 | 9 | 54 | 11 | 2 | 4.0298 | 0.2583 | N/A | 0.157281 (1.0000) | −0.131234 (1.0000) | 1.984800 (0.1415) |
| Glioblastoma Multiforme (TCGA, PanCancer Atlas) | mRNA Expression, RSEM (Batch normalized from Illumina HiSeq_RNASeq V2) | 0 | 3 | 115 | 27 | 0 | 2.6252 | 0.2691 | N/A | 0.180194 (1.0000) | −1.593755 (0.1665) | N/A |
| Prostate Adenocarcinoma (MSKCC, Cancer Cell 2010) | mRNA Expression | 0 | 3 | 78 | 4 | 0 | 2.181 | 0.3361 | N/A | 1.423206 (0.2320) | 0.454433 (0.9743) | N/A |
| Uterine Carcinosarcoma (TCGA, PanCancer Atlas) | mRNA Expression Batch Normalized/Merged from Illumina HiSeq_RNASeq V2 syn4976369 | 0 | 4 | 14 | 37 | 1 | 3.308 | 0.3465 | N/A | 0.104285 (1.0000) | −0.539065 (1.0000) | 1.764353 (0.2330) |
| Acute Myeloid Leukemia (TCGA, PanCancer Atlas) | mRNA Expression, RSEM (Batch normalized from Illumina HiSeq_RNASeq V2) | 0 | 0 | 163 | 2 | 0 | 0.82638 | 0.3633 | N/A | N/A | 0.909052 (0.1817) | N/A |
| Skin Cutaneous Melanoma (TCGA, PanCancer Atlas) | mRNA Expression Batch Normalized/Merged from Illumina HiSeq_RNASeq V2 syn4976369 | 1 | 19 | 146 | 189 | 8 | 3.6483 | 0.4557 | −0.898187 (1.0000) | −1.116994 (1.0000) | −1.235317 (1.0000) | 0.900287 (1.0000) |

TABLE 20-continued

Results of Investigation of Association between Copy Number Variation (CNV) and gene expression for Nectin-4

| Study name | Units | Number of samples/group (n = X) | | | | | Kruskal-Wallis Test | | Pairwise Comparison, Z statistic (adjusted p-value), Bonferonni | | | |
|---|---|---|---|---|---|---|---|---|---|---|---|---|
| | | Deep deletion | Shallow deletion | Diploid | Gain | Amplification | Kruskal-Wallis Statistic | p-value | Deep Deletion - Diploid | Diploid - Shallow deletion | Diploid - Gain | Amplification - Diploid |
| Mesothelioma (TCGA, PanCancer Atlas) | mRNA Expression Batch Normalized/Merged from Illumina HiSeq_RNASeq V2 syn4976369 | 0 | 2 | 56 | 23 | 1 | 2.3747 | 0.4984 | N/A | -1.426445 (0.4612) | 0.418206 (1.0000) | 0.143440 (1.0000) |
| Cholangiocarcinoma (TCGA, Pan Cancer Atlas) | mRNA Expression, RSEM (Batch normalized from Illumina HiSeq_RNASeq V2) | 0 | 0 | 13 | 18 | 5 | 1.3058 | 0.5205 | N/A | N/A | -0.653051 (0.7706) | 1.121055 (0.3934) |
| Pediatric Acute Lymphoid Leukemia - Phase II (TARGET, 2018) | NECTIN4: mRNA expression (RNA-Seq RPKM) | 0 | 4 | 66 | 10 | 1 | 2.2337 | 0.5253 | N/A | 0.133399 (1.0000) | -0.504875 (1.0000) | -1.375728 (0.5067) |
| Diffuse Large B-Cell Lymphoma (TCGA, PanCancer Atlas) | mRNA Expression, RSEM (Batch normalized from Illumina HiSeq_RNASeq V2) | 0 | 2 | 25 | 9 | 1 | 1.4939 | 0.6837 | N/A | 0.374642 (1.0000) | 1.170326 (0.7256) | -0.405844 (1.0000) |
| Cancer Cell Line Encyclopedia (Novartis/Broad, Nature 2012) | mRNA expression (microarray) | 1 | 112 | 396 | 319 | 49 | 1.9013 | 0.7539 | -0.398204 (1.0000) | 0.562427 (1.0000) | -0.847920 (1.0000) | -0.379251 (1.0000) |
| Uveal Melanoma (TCGA, PanCancer Atlas) | mRNA Expression Batch Normalized/Merged from Illumina HiSeq_RNASeq V2 syn4976369 | 0 | 0 | 72 | 8 | 0 | 0.067914 | 0.7944 | N/A | N/A | -0.260603 (0.3972) | N/A |
| Pediatric Wilms' Tumor (TARGET, 2018) | NECTIN4: mRNA expression (RNA-Seq RPKM) | 0 | 1 | 50 | 46 | 4 | 0.78538 | 0.853 | N/A | 0.165021 (1.0000) | -0.815915 (1.0000) | -0.090701 (1.0000) |

TABLE 20-continued

Results of Investigation of Association between Copy Number Variation (CNV) and gene expression for Nectin-4

| Study name | Units | Number of samples/group (n = X) | | | | Kruskal-Wallis Test | | Pairwise Comparison, Z statistic (adjusted p-value), Bonferonni | | |
| --- | --- | --- | --- | --- | --- | --- | --- | --- | --- | --- |
| | | Deep deletion | Shallow deletion | Diploid | Gain | Amplification | Kruskal-Wallis Statistic | p-value | Deep Deletion - Diploid | Diploid - Shallow deletion | Diploid - Gain | Amplification - Diploid |
| Testicular Germ Cell Tumors (TCGA, PanCancer Atlas) | mRNA Expression Batch Normalized/Merged from Illumina HiSeq_RNASeq V2 syn4976369 | 0 | 1 | 76 | 67 | 0 | 0.14279 | 0.9311 | N/A | −0.366969 (1.0000) | 0.061216 (1.0000) | N/A |
| Liver Hepatocellular Carcinoma (TCGA, PanCancer Atlas) | NECTIN4: mRNA Expression, RSEM (Batch normalized from Illumina HiSeq_RNASeq V2) | 0 | 1 | 89 | 224 | 34 | 0.2908 | 0.9618 | N/A | 0.082418 (1.0000) | 0.188961 (1.0000) | 0.363341 (1.0000) |

Example 7: Expression Analysis of Nectin-4 in 6 Cell Lines

1. Study Objective

The objective of the study was to evaluate the expression of Nectin-4 in 6 cell lines by flow cytometry, including 2 Breast cancer (T-47D, MDA-MB-468), 3 Lung cancer (NCI-H292, NCI-H322, NCI-H526) and 1 fibrosarcoma (HT-1080) cell lines).

2. Panel Design

Panel for FCM in T-47D, MDA-MB-468, NCI-H292, NCI-H322 and HT-1080

| Fluorochrome | Blank | Isotype | Panel |
|---|---|---|---|
| PE | — | Isotype ctrl | Nectin-4 |

Panel for NCI-H526

| Fluorochrome | Blank | Isotype | Panel |
|---|---|---|---|
| PE | — | Isotype ctrl | Nectin-4 |
| BV421 | Live/Dead | Live/Dead | Live/Dead |

3. Material
3.1. Sample
Cell Lines List

| Item | Cell lines | Cancer Type | Vendor | Culture Properties | Culture Media |
|---|---|---|---|---|---|
| 1 | T-47D | Breast cancer | ATCC-HTB-133 | adherent | RPMI-1640 + 0.2 Units/ml bovine insulin + 10% FBS |
| 2 | MDA-MB-468 | Breast cancer | ATCC-HTB-132 | adherent | Leibovitz's L-15 + 10% FBS |
| 3 | NCI-H292 | Lung | 91091815 | adherent | RPMI-1640 + 10% FBS |
| 4 | NCI-H322 | Lung | 95111734 | adherent | RPMI-1640 + 2 mM Glutamine + 10% FBS |
| 5 | NCI-H526 | Lung | CRL-5811 | round clusters in suspension | RPMI-1640 + 10% FBS |
| 6 | HT1080 | Fibrosarcoma | ECACC-85111505 | adherent | EMEM + 2 mM Glutamine + 1% Non Essential Amino Acids (NEAA) + 10% FBS |

3.2. Reagents
Antibodies and Kit for Flow Cytometry Analysis

| Fluorescence | Marker | Catalog | Provider | Comment |
|---|---|---|---|---|
| PE | Nectin-4 | FAB2659P | R&D | AAAO0217021 |
| PE | Isotype control IgG2b | IC0041P | R&D | From BICY-20161117A |

DPBS (Corning-21-031-CV)
Staining buffer (eBioscience-00-4222)
Fixation buffer (BD-554655)

3.3. Instruments
Eppendorf Centrifuge 5810R
BD FACS Canto Flow Cytometer (BD)

4. Experimental Methods and Procedures
4.1. Sample Collection

Harvest the cell lines growing in an exponential growth phase. Count cells by haemocytometer with Trypan blue staining. Centrifuge the cells at 400×g for 5 min at 4° C., wash cells for two times with staining buffer, and suspend the cells in staining buffer to $1\times10^7$/mL.

4.2. Antibody Staining

1) Aliquoted 100 μL cell suspension to each well of a 96-well V-plate.
2) Added Isotype control or antibodies into suspension cells and incubated for 30 min at 4° C. in the dark.
3) Washed cells 2× by centrifugation at 400×g for 5 min at 4° C. and discarded supernatant.
4) Resuspended cells with 100 μL fixation buffer and incubated for 30 min at 4° C. in the dark.
5) Washed cells 2× by centrifugation at 300×g for 5 min at 4° C. and removed supernatant
6) Resuspended cells in 400 μL staining buffer.
7) Analyzed the FACS data using FlowJo V10 software.

4.3. Data Analysis

All the FACS data was analyzed by Flowjo V10 software and Graphpad Prism or Excel software.

5. Results
5.1 Gate Strategy for Panel

Gating strategy for Nectin-4 is shown in FIGS. 8-11.

5.2. Data Analysis
5.2.1. Viability of Cell Lines

The viability of cell lines was as below.

| No. | Cell line | Cancer Type | Viability | Viable cells/million |
|---|---|---|---|---|
| 1 | T-47D | Breast | 98.1 | 8.6 |
| 2 | MDA-MB-468 | Breast | 98.7 | 5.3 |
| 3 | NCI-H292 | Lung | 98.7 | 10.4 |
| 4 | NCI-H322 | Lung | 98.5 | 6.6 |
| 5 | NCI-H526 | Lung | 79.9 | 4.0 |
| 6 | HT1080 | Fibrosarcoma | 98.0 | 14.7 |

5.2.2. The Positive Expression of Nectin-4 in Cell Lines

Positive expression and MFI of Nectin-4 in 6 cell lines were as list.

| No. | Cell line | Nectin-4 | MFI-Isotype | MFI-Panel |
|---|---|---|---|---|
| 1 | T-47D | 99.0% | 132 | 1808 |
| 2 | MDA-MB-468 | 99.0% | 184 | 2324 |
| 3 | NCI-H292 | 97.9% | 180 | 729 |
| 4 | NCI-H322 | 99.1% | 145 | 1655 |
| 5 | NCI-H526 | 0.21% | 104 | 91.3 |
| 6 | HT1080 | 1.53% | 134 | 134 |

6. Discussion

There was a high expression of Nectin-4 in Breast cancer T-47D (99.0%), MDA-MB-468 (99.0%) and lung cancer NCI-H292 (97.9%), NCI-H322 (99.1%). In NCI-H526 and HT-1080, no expression of Nectin-4 was found.

Example 8: Expression Analysis of Nectin-4 in 9 CDX Cell Lines by Flow Cytometry

1. Study Objective

The objective of this project is to evaluate the surface expression of Nectin-4 (PVRL-4) in 9 cell lines, including 1 Breast cancer (MDA-MB-468), 4 Lung cancer (NCI-H292, NCI-H358, NCI-H526, A549), 1 Pancreatic cancer (Panc02.13), 2 Colorectal cancer (HCT-116, HT-29) and 1 Bladder cancer (HT1376) cell lines.

2. Panel Design

Panel for FCM in 9 Cell Lines

| Fluorochrome | Blank | Isotype | Panel |
|---|---|---|---|
| PE | — | Isotype control IgG2b | Nectin-4 |
| BV421 | Live/Dead | Live/Dead | Live/Dead |

3. Materials 3.1 Samples

Cell Lines List

| Item | Cell Line | Cancer Type | Vendor | Culture Properties | Culture Media |
|---|---|---|---|---|---|
| 1 | HT1376 | Bladder | ATCC-CRL-1472 | adherent | EMEM + 10% FBS |
| 2 | MDA-MB-468 | Breast | ATCC-HTB-132 | adherent | Leibovitz's L-15 + 10% FBS |
| 3 | HCT-116 | Colorectal | ATCC-CCL-247 | adherent | RPMI 1640 + 10% FBS |
| 4 | HT-29 | Colorectal | ATCC-HTB-38 | adherent | McCoy's 5a + 10% FBS |
| 5 | A549 | Lung | ATCC-CCL-185 | adherent | F-12K + 10% FBS |
| 6 | NCI-H292 | Lung | ECACC-91091815 | suspension | RPMI 1640 + 10% FBS |
| 7 | NCI-H358 | Lung | ECACC-95111733 | adherent | RPMI 1640 + 10% FBS |
| 8 | NCI-526 | Lung | ATCC-CRL-5811 | adherent | RPMI 1640 + 10% FBS |
| 9 | Panc02.13 | Pancreas | ATCC-CRL-2554 | adherent | RPMI-1640 + 15% FBS + 5 ug/ml human insulin |

3.2. Reagents

1) DPBS (Corning, 21-031-CV)
2) Trypsin 0.25% (Invitrogen-25200072)
3) Staining buffer (eBioscience, 00-4222)
4) Fixation buffer (BD, 554655)
5) Antibody

| Fluorescence | Marker | Catalog | Vendor | Comment |
|---|---|---|---|---|
| PE | Nectin-4 | FAB2659P | R&D | AAAO0217021 |
| PE | Mouse IgG2b | IC0041P | R&D | |
| BV421 | Live/Dead | L34964 | Invitrogen | — |

3.3. Instruments

Eppendorf Centrifuge 5810R

BD FACS Canto Flow Cytometer (BD)

4. Experimental Methods and Procedures 4.1 Cell Culture

Cell Thawing

1) Cleaned the frozen vials with 70% alcohol and quickly thawed vials in 37° C. water bath.
2) Centrifuged cell suspension at approximately 1000 rpm for 5 minutes, removed the supernatant and added pre-warming medium into the flasks.
3) Incubated culture flasks at 37° C., 5% $CO_2$ incubator.

Cell Passage

1) Warmed medium and trypsin in 37° C. water bath.
2) Removed culture medium and rinsed the cell layer with DPBS.
3) Added 5 mL 0.25% trypsin solution to flask and diluted trypsin with 5 mL medium.
4) Centrifuged cell suspension at 1000 rpm for 5 min.
5) Added 15 mL fresh medium and re-suspended cells by pipetting gently.
6) Added appropriate cell suspension to new culture flasks.
7) Incubated culture flasks at 37° C., 5% $CO_2$ incubator.

4.2. Samples Collection

Harvested the cell lines growing in an exponential growth phase. Counted cells with Trypan blue staining. Centrifuged the cells at 400×g for 5 min at 4° C., washed cells with staining buffer for twice, and suspended the cells in staining buffer to $5×10^6$/mL.

4.3. Antibody Staining

Aliquoted 100 μL cell suspension to each well of a 96-well V-plate. Added Isotype control or antibodies into suspension cells and incubated for 30 min at 4° C. in the dark. Washed cells 2 times by centrifugation at 400×g for 5 min at 4° C. and discarded supernatant. Re-suspended cells in 300 μL staining buffer. Analyzed the FACS data using Flow Jo V10 software.

4.4. Data Analysis

All the FACS data was analyzed by Flow Jo V10 software and GraphPad Prism or Excel software.

5. Results 5.1. Gate Strategy for Panel

Gating strategy for Nectin-4 is shown in FIGS. 12-16.

5.2. Data Analysis

Positive expression and MFI of Nectin-4 in 9 cell lines were as list.

| No. | Cell Line | Nectin-4 | MFI-Isotype | MFI-Panel |
|---|---|---|---|---|
| 1 | HT1376 | 92.4% | 36.2 | 803 |
| 2 | MDA-MB-468 | 97.1% | 28.9 | 460 |
| 3 | HCT-116 | 1.85% | 14.5 | 15.6 |
| 4 | HT-29 | 40.0% | 20.5 | 88.3 |
| 5 | A549 | 1.07% | 20.5 | 21.6 |
| 6 | NCI-H292 | 71.1% | 22.9 | 149 |
| 7 | NCI-H358 | 90.1% | 26.5 | 361 |
| 8 | NCI-526 | 1.22% | 8.33 | 12.1 |
| 9 | Panc02.13 | 51.9% | 36.2 | 128 |

6. Discussion

There was a high expression of Nectin-4 in Bladder cancer HT-1376 (92.4%), Breast cancer MDA-MB-468 (97.1%) and lung cancer NCI-H358 (90.1%). A medium expression of Nectin-4 was found in HT-29 (40.0%), NCI-H292 (71.1%) and Panc02.13 (51.9%). In HCT-116, A549 and NCI-526, no expression of Nectin-4 was found. This data will be used to guide model selection for efficacy studies.

Example 9: In Vivo Efficacy Studies

Example 9.1: In Vivo Efficacy Study of Test Articles in Treatment of A549 Xenograft in Balb/c Nude Mice 1. Study Objective The objective of the research is to evaluate the in vivo anti-tumor efficacy of test articles in treatment of A549 xenograft in Balb/c nude mice.

2. Experimental Design

| Group | Treatment | n | Dose (mg/kg) | Dosing Volume (µl/g) | Dosing Route | Schedule |
|---|---|---|---|---|---|---|
| 1 | Vehicle | 5 | — | 10 | iv | qw |
| 2 | BCY8245 | 3 | 3 mg/kg | 10 | iv | qw |
| 3 | BCY8245 | 3 | 3 mg/kg | 10 | iv | biw |
| 4 | BCY8245 | 3 | 5 mg/kg | 10 | iv | qw |

3. Materials
Animals and Housing Condition
3.1.1. Animals
Species: *Mus Musculus*
Strain: Balb/c nude
Age: 6-8 weeks
Sex: female
Body weight: 18-22 g
Number of animals: 41 mice plus spare
3.1.2. Housing Condition The mice were kept in individual ventilation cages at constant temperature and humidity with 3 or 5 animals in each cage.
Temperature: 20~26° C.
Humidity 40-70%.

Cages: Made of polycarbonate. The size is 300 mm×180 mm×150 mm. The bedding material is corn cob, which is changed twice per week.
Diet: Animals had free access to irradiation sterilized dry granule food during the entire study period.
Water: Animals had free access to sterile drinking water.
Cage identification: The identification labels for each cage contained the following information: number of animals, sex, strain, the date received, treatment, study number, group number and the starting date of the treatment.
Animal identification: Animals were marked by ear coding.

4. Experimental Methods and Procedures
4.1. Cell Culture

The A549 tumor cells were maintained in vitro as a monolayer culture in F-12K medium supplemented with 10% heat inactivated fetal bovine serum at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

4.2. Tumor Inoculation

Each mouse was inoculated subcutaneously at the right flank with A549 tumor cells ($5\times10^6$) in 0.2 ml of PBS for tumor development. 41 animals were randomized when the average tumor volume reached 158 $mm^3$. The test article administration and the animal numbers in each group were shown in the experimental design table.

4.3. Testing Article Formulation Preparation

| Test article | Con. (mg/ml) | Formulation |
|---|---|---|
| Vehicle | — | 25 mM Histidine pH 7 10% sucrose |
| BCY8245 | 0.5 | Dilute 400 µl 1 mg/ml BCY8245 stock with 400 µl Histidine buffer |
| BCY8245 | 0.3 | Dilute 240 µl 1 mg/ml BCY8245 stock with 560 µl Histidine buffer |

4.4. Sample Collection

At the end of study, the tumor of all groups were collected at 2 h post last dosing.

5. Results
5.1. Tumor Growth Curves

Figure 17:
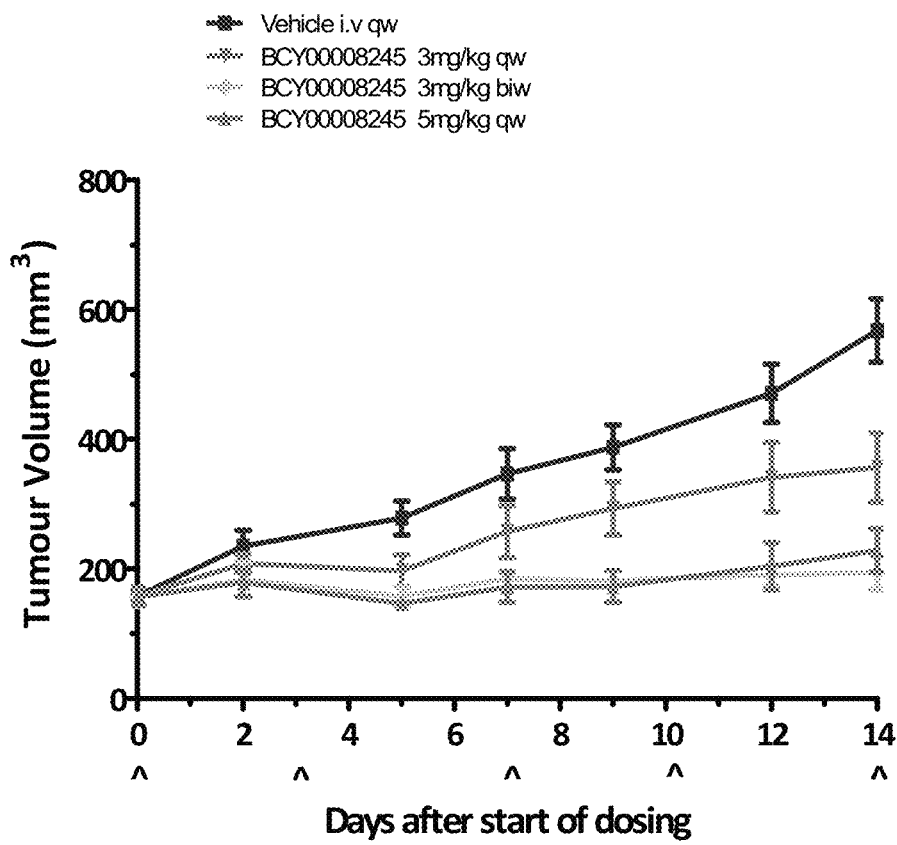
FIG. 17: Tumor volume trace after administering BCY8245 to female Balb/c nude mice bearing A549 xenograft.

The tumor growth curve is shown in FIG. 17.

5.2. Tumor Volume Trace

Mean tumor volume over time in female Balb/c nude mice bearing A549 xenograft is shown in Table 21.

TABLE 21

Tumor volume trace over time

| | Days after the start of treatment | | | | | | |
|---|---|---|---|---|---|---|---|
| Gr. Treatment | 0 | 2 | 5 | 7 | 9 | 12 | 14 |
| 1 Vehicle, qw | 158 ± 13 | 235 ± 24 | 278 ± 26 | 346 ± 39 | 387 ± 35 | 471 ± 45 | 568 ± 49 |
| 2 BCY8245, 3 mpk, qw | 157 ± 10 | 208 ± 15 | 197 ± 25 | 257 ± 40 | 293 ± 41 | 341 ± 54 | 356 ± 53 |
| 3 BCY8245, 3 mpk, biw | 157 ± 14 | 183 ± 27 | 158 ± 16 | 184 ± 6 | 182 ± 8 | 190 ± 15 | 194 ± 27 |
| 4 BCY8245, 5 mpk, qw | 157 ± 14 | 179 ± 22 | 147 ± 10 | 172 ± 23 | 173 ± 24 | 204 ± 36 | 228 ± 33 |

5.3. Tumor Growth Inhibition Analysis

Tumor growth inhibition rate for test articles in the A549 xenograft model was calculated based on tumor volume measurements at day 14 after the start of treatment.

TABLE 22

Tumor growth inhibition analysis

| Gr | Treatment | Tumor Volume $(mm^3)^a$ | $T/C^b$ (%) | TGI (%) | P value compared with vehicle |
|---|---|---|---|---|---|
| 1 | Vehicle, qw | 568 ± 49 | — | — | — |
| 2 | BCY8245, 3 mpk, qw | 356 ± 53 | 62.8 | 51.4 | p < 0.05 |
| 3 | BCY8245, 3 mpk, biw | 194 ± 27 | 34.2 | 90.8 | p < 0.001 |

TABLE 22-continued

Tumor growth inhibition analysis

| Gr | Treatment | Tumor Volume (mm³)[a] | T/C[b] (%) | TGI (%) | P value compared with vehicle |
|---|---|---|---|---|---|
| 4 | BCY8245, 5 mpk, qw | 228 ± 33 | 40.2 | 82.6 | p < 0.001 |

[a]Mean ± SEM.
[b]Tumor Growth Inhibition is calculated by dividing the group average tumor volume for the treated group by the group average tumor volume for the control group (T/C).

6. Results Summary and Discussion

In this study, the therapeutic efficacy of test articles in the A549 xenograft model was evaluated. The measured tumor volumes of all treatment groups at various time points are shown in FIG. 17 and Tables 21 and 22.

The mean tumor size of vehicle treated mice reached 568 mm³ on day 14. BCY8245 at 3 mg/kg, qw (TV=356 mm³, TGI=51.4%, p<0.05), 3 mg/kg, biw (TV=194 mm³, TGI=90.8%, p<0.01) and 5 mg/kg, qw (TV=228 mm³, TGI=82.6%, p<0.001) produced significant anti-tumor anti-tumor activity in dose or dose-frequency dependent manner.

Animals in BCY8245 groups maintained the bodyweight well. In this cell line, which shows minimal expression of Nectin-4 in FACS studies, tumor growth is restrained by BCY8245 but the tumor does not undergo regression, emphasising the target driven requirement for optimal efficacy.

Example 9.2: In Vivo Efficacy Study of Test Articles in Treatment of HCT116 Xenograft in Balb/c Nude Mice 1. Study Objective The objective of the research is to evaluate the in vivo anti-tumor efficacy of test articles in treatment of HCT116 xenograft in Balb/c nude mice.

2. Experimental Design

| Group | Treatment | n | Dose (mg/kg) | Dosing Volume (μl/g) | Dosing Route | Schedule |
|---|---|---|---|---|---|---|
| 1 | Vehicle | 5 | — | 10 | iv | qw |
| 2 | BCY8245 | 3 | 3 | 10 | iv | qw |
| 3 | BCY8245 | 3 | 3 | 10 | iv | biw |
| 4 | BCY8245 | 3 | 5 | 10 | iv | qw |

3. Materials
3.1. Animals and Housing Condition
3.1.1. Animals
Species: *Mus Musculus*
Strain: Balb/c nude
Age: 6-8 weeks
Sex: female
Body weight: 18-22 g
Number of animals: 41 mice plus spare 3.1.2. Housing Condition The mice were kept in individual ventilation cages at constant temperature and humidity with 3 or 5 animals in each cage.
Temperature: 20~26° C.
Humidity 40-70%.
Cages: Made of polycarbonate. The size is 300 mm×180 mm×150 mm. The bedding material is corn cob, which is changed twice per week.
Diet: Animals had free access to irradiation sterilized dry granule food during the entire study period.
Water: Animals had free access to sterile drinking water.
Cage identification: The identification labels for each cage contained the following information: number of animals, sex, strain, the date received, treatment, study number, group number and the starting date of the treatment.
Animal identification: Animals were marked by ear coding.

4. Experimental Methods and Procedures
4.1 Cell Culture

The HCT116 cells were maintained in medium supplemented with 10% heat inactivated fetal bovine serum at 37° C. in an atmosphere of 5% $CO_2$ in air. The tumor cells were routinely subcultured twice weekly. The cells growing in an exponential growth phase were harvested and counted for tumor inoculation.

4.2. Tumor Inoculation

Each mouse was inoculated subcutaneously at the right flank with HCT116 tumor cells ($5.0 \times 10^6$) in 0.2 ml of PBS for tumor development. 41 animals were randomized when the average tumor volume reached 166 mm³. The test article administration and the animal numbers in each group were shown in the experimental design table.

4.3. Testing Article Formulation Preparation

| Test article | Con. (mg/ml) | Formulation |
|---|---|---|
| Vehicle | — | 25 mM Histidine pH 7 10% sucrose |
| BCY8245 | 0.5 | Dilute 400 μl 1 mg/ml BCY8245 stock with 400 μl Histidine buffer |
| BCY8245 | 0.3 | Dilute 240 μl 1 mg/ml BCY8245 stock with 560 μl Histidine buffer |

4.4. Sample Collection

At the end of study on day 14, tumors from group 1 and 2 were collected for FFPE. For group 4, plasma were collected at 5 min, 15 min, 30 min, 60 min and 120 min post dosing. Tumors were also collected and stored at −80° C.

5. Results
5.1. Tumor Growth Curves

Figure 18:
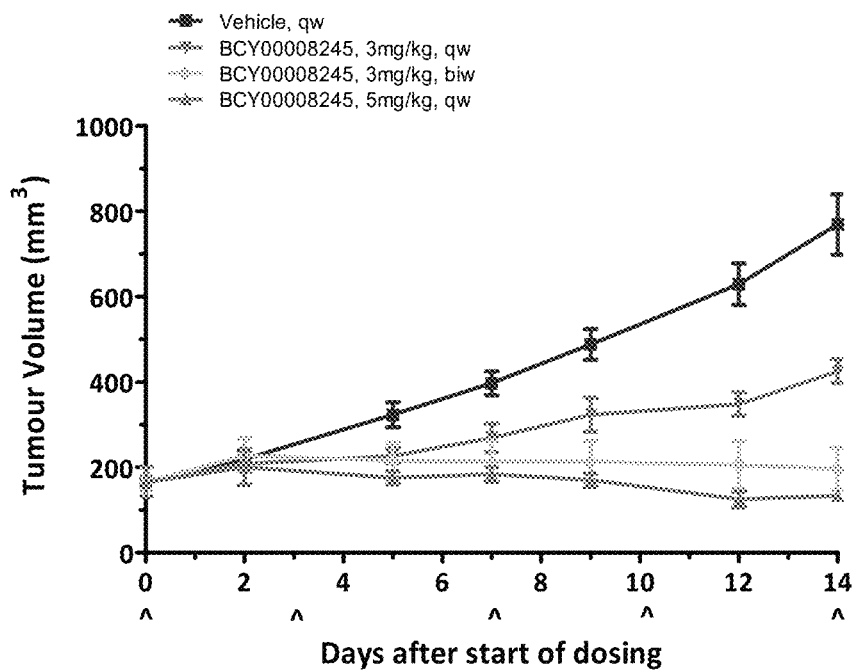
FIG. 18: Tumor volume trace after administering BCY8245 to female Balb/c nude mice bearing HCT116 xenograft.

The tumor growth curve is shown in FIG. 18.

5.2. Tumor Volume Trace

Mean tumor volume over time in female Balb/c nude mice bearing HCT116 xenograft is shown in Table 23.

TABLE 23

Tumor volume trace over time

| Group | Treatment | Days after the start of treatment | | | | | | |
|---|---|---|---|---|---|---|---|---|
| | | 0 | 2 | 4 | 7 | 9 | 12 | 14 |
| 1 | Vehicle, qw | 166 ± 12 | 219 ± 21 | 323 ± 29 | 397 ± 28 | 488 ± 36 | 630 ± 49 | 769 ± 71 |
| 2 | BCY8245, 3 mpk, qw | 167 ± 11 | 209 ± 13 | 227 ± 17 | 269 ± 33 | 324 ± 39 | 348 ± 27 | 425 ± 28 |

TABLE 23-continued

Tumor volume trace over time

| | | Days after the start of treatment | | | | | | |
|---|---|---|---|---|---|---|---|---|
| Group | Treatment | 0 | 2 | 4 | 7 | 9 | 12 | 14 |
| 3 | BCY8245, 3 mpk, biw | 166 ± 18 | 229 ± 40 | 215 ± 42 | 213 ± 49 | 213 ± 48 | 206 ± 55 | 197 ± 50 |
| 4 | BCY8245, 5 mpk, qw | 166 ± 35 | 201 ± 42 | 176 ± 15 | 183 ± 17 | 170 ± 16 | 125 ± 18 | 134 ± 12 |

5.3. Tumor Growth Inhibition Analysis

Tumor growth inhibition rate for test articles in the HCT116 xenograft model was calculated based on tumor volume measurements at day 14 after the start of the treatment.

TABLE 24

Tumor growth inhibition analysis

| Group | Treatment | Tumor Volume $(mm^3)^a$ | $T/C^b$ (%) | TGI (%) | P value |
|---|---|---|---|---|---|
| 1 | Vehicle, qw | 769 ± 71 | — | — | — |
| 2 | BCY8245, 3 mpk, qw | 425 ± 28 | 55.2 | 57.1 | p < 0.001 |
| 3 | BCY8245, 3 mpk, biw | 197 ± 50 | 25.6 | 94.9 | p < 0.001 |
| 4 | BCY8245, 5 mpk, qw | 134 ± 12 | 17.4 | 105.2 | p < 0.001 |

$^a$Mean ± SEM;
$^b$Tumor Growth Inhibition is calculated by dividing the group average tumor volume for the treated group by the group average tumor volume for the control group (T/C).

6. Results Summary and Discussion

In this study, the therapeutic efficacy of test articles in the HCT116 xenograft model was evaluated. The measured tumor volumes of all treatment groups at various time points are shown in FIG. 18 and Tables 23 and 24.

The mean tumor size of vehicle treated mice reached 769 mm$^3$ on day 14 after the start of treatment. BCY8245 at 3 mg/kg, qw (TV=425 mm$^3$, TGI=57.1%, p<0.001), 3 mg/kg, biw (TV=197 mm$^3$, TGI=94.9%, p<0.001) and 5 mg/kg, qw (TV=134 mm$^3$, TGI=105.2%, p<0.001) produced significant anti-tumor antitumor activity in dose or dose-frequency dependent manner.

In this study, animals in all of 5 mg/kg qw groups lost over average 10% bodyweight.

In this cell line, which shows minimal expression of Nectin-4 in FACS studies, tumor growth is restrained by BCY8245 but the tumor does not undergo regression, emphasising the target driven requirement for optimal efficacy.

Example 9.3: In Vivo Efficacy Study of Test Articles in Treatment of HT-1376 Xenograft in CB17-SCID Mice 1. Study Objective The objective of the research is to evaluate the in vivo anti-tumor efficacy of test articles in treatment of HT-1376 xenograft in CB17-SCID mice.

2. Experimental Design

| Group | Treatment | n | Dose (mg/kg) | Dosing Volume (μl/g) | Dosing Route | Schedule |
|---|---|---|---|---|---|---|
| 1 | Vehicle | 5 | — | 10 | iv | qw |
| 2 | BCY8245 | 3 | 3 mg/kg | 10 | iv | qw |
| 3 | BCY8245 | 3 | 3 mg/kg | 10 | iv | biw |
| 4 | BCY8245 | 3 | 5 mg/kg | 10 | iv | qw |

3. Materials 3.1 Animals and Housing Condition 3.1.1. Animals

Species: *Mus Musculus*

Strain: CB17-SCID

Age: 6-8 weeks

Sex: female

Body weight: 18-22 g

Number of animals: 41 mice plus spare 3.1.2. Housing Condition

The mice were kept in individual ventilation cages at constant temperature and humidity with 3 or 5 animals in each cage.

Temperature: 20~26° C.

Humidity 40-70%.

Cages: Made of polycarbonate. The size is 300 mm×180 mm×150 mm. The bedding material is corn cob, which is changed twice per week.

Diet: Animals had free access to irradiation sterilized dry granule food during the entire study period.

Water: Animals had free access to sterile drinking water.

Cage identification: The identification labels for each cage contained the following information: number of animals, sex, strain, the date received, treatment, study number, group number and the starting date of the treatment.

Animal identification: Animals were marked by ear coding.

4. Experimental Methods and Procedures 4.1 Cell Culture

The HT-1376 tumor cells will be maintained in EMEM medium supplemented with 10% heat inactivated fetal bovine serum at 37° C. in an atmosphere of 5% $CO_2$ in air. The tumor cells will be routinely subcultured twice weekly. The cells growing in an exponential growth phase will be harvested and counted for tumor inoculation.

4.2 Tumor Inoculation

Each mouse was inoculated subcutaneously at the right flank with HT-1376 tumor cells (5×10$^6$) with Matrigel (1:1) in 0.2 ml of PBS for tumor development. 41 animals were randomized when the average tumor volume reached 153 mm$^3$. The test article administration and the animal numbers in each group were shown in the experimental design table.

4.3. Testing Article Formulation Preparation

| Test article | Con. (mg/ml) | Formulation |
|---|---|---|
| Vehicle | — | 25 mM Histidine pH 7 10% sucrose |
| BCY8245 | 0.5 | Dilute 400 μl 1 mg/ml BCY8245 stock with 400 μl Histidine buffer |
| BCY8245 | 0.3 | Dilute 240 μl 1 mg/ml BCY8245 stock with 560 μl Histidine buffer |

4.4. Sample Collection

At the end of study, the plasma of group 4 was collected at 5 min, 15 min, 30 min, 60 min and 120 min post last dosing. The tumor of group 4 was collected at 2 h post last dosing. The tumor of groups 1, 2 and 3 were collected at 2 h post last dosing.

Figure 19:
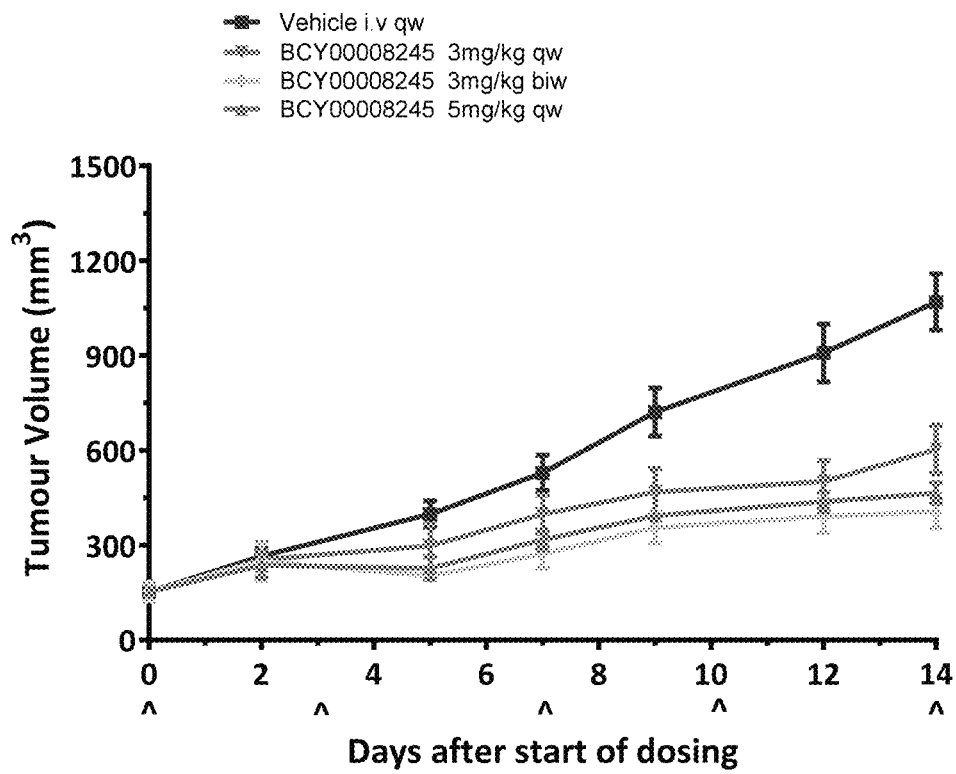
FIG. 19: Tumor volume trace after administering BCY8245 to female CB17-SCID mice bearing HT-1376 xenograft.

5. Results
5.1. Tumor Growth Curves
The tumor growth curve is shown in FIG. 19.
5.2. Tumor Volume Trace
Mean tumor volume over time in female CB17-SCID mice bearing HT-1376 xenograft is shown in Table 25.

TABLE 25

Tumor volume trace over time

| | | Days after the start of treatment | | | | | |
|---|---|---|---|---|---|---|---|
| Gr. | Treatment | 0 | 2 | 5 | 7 | 9 | 12 | 14 |
| 1 | Vehicle, qw | 153 ± 16 | 266 ± 30 | 398 ± 41 | 529 ± 56 | 721 ± 76 | 908 ± 91 | 1069 ± 90 |
| 2 | BCY8245, 3 mpk, qw | 153 ± 26 | 254 ± 53 | 298 ± 69 | 398 ± 61 | 468 ± 73 | 502 ± 67 | 603 ± 76 |
| 3 | BCY8245, 3 mpk, biw | 154 ± 30 | 248 ± 58 | 203 ± 15 | 273 ± 45 | 356 ± 50 | 391 ± 53 | 407 ± 53 |
| 4 | BCY8245, 5 mpk, qw | 153 ± 15 | 237 ± 41 | 228 ± 36 | 317 ± 31 | 394 ± 20 | 438 ± 31 | 465 ± 33 |

5.3. Tumor Growth Inhibition Analysis

Tumor growth inhibition rate for Test articles in the HT-1376 xenograft model was calculated based on tumor volume measurements at day 14 after the start of treatment.

TABLE 26

Tumor growth inhibition analysis

| Gr | Treatment | Tumor Volume (mm³)[a] | T/C[b] (%) | TGI (%) | P value compared with vehicle |
|---|---|---|---|---|---|
| 1 | Vehicle, qw | 1069 ± 90 | — | — | — |
| 2 | BCY8245, 3 mpk, qw | 603 ± 76 | 56.4 | 50.9 | p < 0.01 |
| 3 | BCY8245, 3 mpk, biw | 407 ± 53 | 38.1 | 72.3 | p < 0.001 |
| 4 | BCY8245, 5 mpk, qw | 465 ± 33 | 43.5 | 66.0 | p < 0.001 |

[a]Mean ± SEM.
[b]Tumor Growth Inhibition is calculated by dividing the group average tumor volume for the treated group by the group average tumor volume for the control group (T/C).

6. Results Summary and Discussion

In this study, the therapeutic efficacy of test articles in the HT-1376 xenograft model was evaluated. The measured tumor volumes of all treatment groups at various time points are shown in FIG. 19 and Tables 25 and 26.

The mean tumor size of vehicle treated mice reached 1069 mm³ on day 14. BCY8245 at 3 mg/kg, qw (TV=603 mm³, TGI=50.9%, p<0.01), 3 mg/kg, biw (TV=407 mm³, TGI=72.3%, p<0.001) and 5 mg/kg, qw (TV=465 mm³, TGI=66.0%, p<0.001) produced significant antitumor activity. In this study, BCY8245 at 5 mg/kg qw caused over 10% animal bodyweight loss during the treatment schedule.

Example 9.4: In Vivo Efficacy Study of Test Articles in Treatment of MDA-MB-468 Xenograft in Balb/c Nude Mice

1. Study Objective
The objective of the research is to evaluate the in vivo anti-tumor efficacy of test articles in treatment of MDA-MB-468 xenograft in Balb/c nude mice.

2. Experimental Design

| Group | Treatment | n | Dose (mg/kg) | Dosing Volume (μl/g) | Dosing Route | Schedule |
|---|---|---|---|---|---|---|
| 1 | Vehicle | 5 | — | 10 | iv | qw |
| 2 | BCY8245 | 3 | 3 mg/kg | 10 | iv | qw |
| 3 | BCY8245 | 3 | 3 mg/kg | 10 | iv | biw |
| 4 | BCY8245 | 3 | 5 mg/kg | 10 | iv | qw |

3. Materials
3.1. Animals and Housing Condition
3.1.1. Animals
Species: *Mus Musculus*
Strain: Balb/c nude
Age: 6-8 weeks
Sex: female
Body weight: 18-22 g
Number of animals: 41 mice plus spare
3.1.2. Housing Condition
The mice were kept in individual ventilation cages at constant temperature and humidity with 3 or 5 animals in each cage.
Temperature: 20~26° C.
Humidity 40-70%.
Cages: Made of polycarbonate. The size is 300 mm×180 mm×150 mm. The bedding material is corn cob, which is changed twice per week.
Diet: Animals had free access to irradiation sterilized dry granule food during the entire study period.
Water: Animals had free access to sterile drinking water.

Cage identification: The identification labels for each cage contained the following information: number of animals, sex, strain, the date received, treatment, study number, group number and the starting date of the treatment.

Animal identification: Animals were marked by ear coding.

4. Experimental Methods and Procedures 4.1. Cell Culture

The tumor cells were maintained in Leibovitz's L-15 medium supplemented with 10% heat inactivated fetal bovine serum at 37° C. in an atmosphere of 5% $CO_2$ in air. The tumor cells were routinely subcultured twice weekly. The cells growing in an exponential growth phase were harvested and counted for tumor inoculation.

4.2. Tumor Inoculation

Each mouse was inoculated subcutaneously at the right flank with MDA-MB-468 tumor cells ($10 \times 10^6$) in 0.2 ml of PBS supplemented with 50% matrigel for tumor development. 41 animals were randomized when the average tumor volume reached 196 mm³. The test article administration and the animal numbers in each group were shown in the experimental design table.

4.3. Testing Article Formulation Preparation

| Test article | Con. (mg/ml) | Formulation |
|---|---|---|
| Vehicle | — | 25 mM Histidine pH 7 10% sucrose |
| BCY8245 | 1 | Dissolve 10.56 mg BCY8245 in 10.518 ml Histidine buffer |
| BCY8245 | 0.5 | Dilute 400 µl 1 mg/ml BCY8245 stock with 400 µl Histidine buffer |
| BCY8245 | 0.3 | Dilute 240 µl 1 mg/ml BCY8245 stock with 560 µl Histidine buffer |

4.4. Sample Collection

At the day 21 of study, the plasma of group 2 was collected at 5 min, 15 min, 30 min, 60 min and 120 min post last dosing. The tumors of groups 1 and 3 were collected at 2 h post last dosing. The animals in group 4 were kept running for another 21 days without any dosing, and the tumors of these groups were collected on day 42.

5. Results 5.1. Tumor Growth Curves

Figure 20:
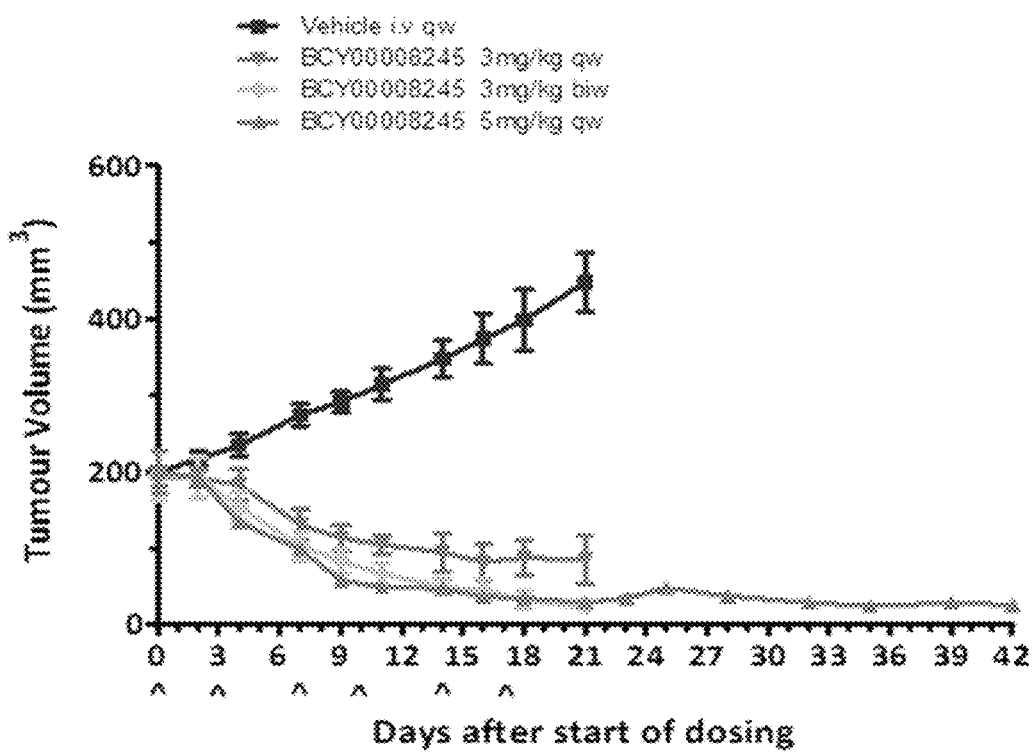
FIG. 20: Tumor volume trace after administering BCY8245 to female Balb/c nude mice bearing MDA-MB-468 xenograft.

The tumor growth curve is shown in FIG. 20.

5.2. Tumor Volume Trace

Mean tumor volume over time in female Balb/c nude mice bearing MDA-MB-468 xenograft is shown in Table 27 and 28.

5.3. Tumor Growth Inhibition Analysis

Tumor growth inhibition rate for test articles in the MDA-MB-468 xenograft model was calculated based on tumor volume measurements at day 21 after the start of the treatment.

TABLE 27

Tumor volume trace over time (Day 0 to day 21)

| Gr. | Treatment | 0 | 2 | 4 | 7 | 9 | 11 | 14 | 16 | 18 | 21 |
|---|---|---|---|---|---|---|---|---|---|---|---|
| 1 | Vehicle, qw | 199 ± 6 | 217 ± 9 | 235 ± 15 | 274 ± 14 | 291 ± 14 | 314 ± 20 | 348 ± 24 | 374 ± 33 | 398 ± 39 | 447 ± 39 |
| 2 | BCY8245, 3 mpk, qw | 194 ± 12 | 192 ± 26 | 184 ± 20 | 131 ± 20 | 113 ± 17 | 104 ± 13 | 94 ± 25 | 81 ± 23 | 87 ± 23 | 85 ± 31 |
| 3 | BCY8245, 3 mpk, biw | 195 ± 33 | 193 ± 27 | 154 ± 20 | 103 ± 20 | 83 ± 16 | 67 ± 14 | 49 ± 11 | 45 ± 14 | 32 ± 12 | 22 ± 4 |
| 4 | BCY8245, 5 mpk, qw | 199 ± 28 | 193 ± 11 | 135 ± 4 | 98 ± 5 | 58 ± 5 | 49 ± 5 | 47 ± 2 | 37 ± 4 | 35 ± 3 | 29 ± 3 |

TABLE 28

Tumor volume trace over time (Day 23 to day 42)

| Gr. | Treatment | 23 | 25 | 28 | 32 | 35 | 39 | 42 |
|---|---|---|---|---|---|---|---|---|
| 4 | BCY8245, 5 mpk, qw | 35 ± 5 | 48 ± 5 | 37 ± 7 | 28 ± 6 | 24 ± 4 | 28 ± 6 | 26 ± 6 |

TABLE 29

Tumor growth inhibition analysis

| Gr | Treatment | Tumor Volume | T/C[b] (%) | TGI (%) | P value with |
|---|---|---|---|---|---|
| 1 | Vehicle, qw | 447 ± 39 | — | — | — |
| 2 | BCY8245, 3 mpk, qw | 85 ± 31 | 18.9 | 144.2 | p < 0.001 |
| 3 | BCY8245, 3 mpk, biw | 22 ± 4 | 4.9 | 169.8 | p < 0.001 |
| 4 | BCY8245, 5 mpk, qw | 29 ± 3 | 6.6 | 168.4 | p < 0.001 |

[a]Mean ± SEM.
[b]Tumor Growth Inhibition is calculated by dividing the group average tumor volume for the treated group by the group average tumor volume for the control group (T/C).

6. Results Summary and Discussion

In this study, the therapeutic efficacy of test articles in the MDA-MB-468 xenograft model was evaluated. The measured tumor volumes of all treatment groups at various time points are shown in FIG. 20 and Tables 27 to 29.

The mean tumor size of vehicle treated mice reached 447 mm$^3$ on day 21. BCY8245 at 3 mg/kg, qw (TV=85 mm$^3$, TGI=144.2%, p<0.001), 3 mg/kg, biw (TV=22 mm$^3$, TGI=169.8%, p<0.001) and 5 mg/kg, qw (TV=29 mm$^3$, TGI=168.4%, p<0.001) produced significant anti-tumor antitumor activity in dose or dose-frequency dependent manner.

The dosing of 5 mg/kg groups were suspended from day 21, the tumors didn't show any relapse during extra 3 weeks' monitoring schedule. In this cell line, which shows high expression of Nectin-4 in FACS studies, BCY8245 causes regression of the tumor emphasizing the target driven nature of optimal efficacy.

Example 9.5: In Vivo Efficacy Study of Test Articles in Treatment of NCI-H292 Xenograft in Balb/c Nude Mice 1. Study Objective The objective of the research is to evaluate the in vivo anti-tumor efficacy of test articles in treatment of NCI-H292 xenograft in Balb/c nude mice.

2. Experimental Design

| Group | Treatment | n | Dose (mg/kg) | Dosing Volume (µl/g) | Dosing Route | Schedule |
|---|---|---|---|---|---|---|
| 1 | Vehicle | 5 | — | 10 | iv | qw |
| 2 | BCY8245 | 3 | 3 mg/kg | 10 | iv | qw |
| 3 | BCY8245 | 3 | 3 mg/kg | 10 | iv | biw |
| 4 | BCY8245 | 3 | 5 mg/kg | 10 | iv | qw |

3. Materials
3.1. Animals and Housing Condition
3.1.1. Animals
Species: *Mus Musculus*
Strain: Balb/c nude
Age: 6-8 weeks
Sex: female
Body weight: 18-22 g
Number of animals: 41 mice plus spare 3.1.2. Housing Condition The mice were kept in individual ventilation cages at constant temperature and humidity with 3 or 5 animals in each cage.

Temperature: 20~26° C.

Humidity 40-70%.

Cages: Made of polycarbonate. The size is 300 mm×180 mm×150 mm. The bedding material is corn cob, which is changed twice per week.

Diet: Animals had free access to irradiation sterilized dry granule food during the entire study period.

Water: Animals had free access to sterile drinking water.

Cage identification: The identification labels for each cage contained the following information: number of animals, sex, strain, the date received, treatment, study number, group number and the starting date of the treatment.

Animal identification: Animals were marked by ear coding.

4. Experimental Methods and Procedures
4.1. Cell Culture

The NCI-H292 tumor cells were maintained in vitro as a monolayer culture in RPMI-1640 medium supplemented with 10% heat inactivated fetal bovine serum at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

4.2. Tumor Inoculation

Each mouse was inoculated subcutaneously at the right flank with NCI-H292 tumor cells (10×10$^6$) in 0.2 ml of PBS for tumor development. 41 animals were randomized when the average tumor volume reached 162 mm$^3$. The test article administration and the animal numbers in each group were shown in the experimental design table.

4.3. Testing Article Formulation Preparation

| Test article | Con. (mg/ml) | Formulation |
|---|---|---|
| Vehicle | — | 25 mM Histidine pH 7 10% sucrose |
| BCY8245 | 1 | Dissolve 10.56 mg BCY8245 in 10.518 ml Histidine buffer |
| BCY8245 | 0.5 | Dilute 400 µl 1 mg/ml BCY8245 stock with 400 µl Histidine buffer |
| BCY8245 | 0.3 | Dilute 240 µl 1 mg/ml BCY8245 stock with 560 µl Histidine buffer |

4.4. Sample Collection

At the end of study, the tumor of all groups were collected at 2 h post last dosing.

5. Results
5.1 Tumor Growth Curves

Figure 21:
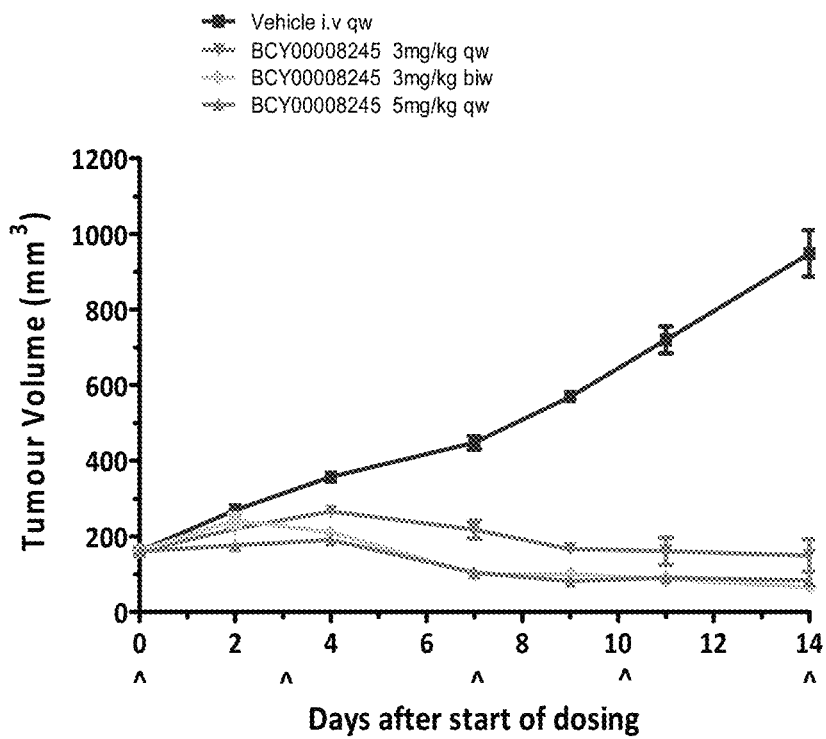
FIG. 21: Tumor volume trace after administering BCY8245 to female Balb/c nude mice bearing NCI-H292 xenograft.

The tumor growth curve is shown in FIG. 21.

5.2. Tumor Volume Trace

Mean tumor volume over time in female Balb/c nude mice bearing NCI-H292 xenograft is shown in Table 30.

TABLE 30

Tumor volume trace over time

| | | Days after the start of treatment | | | | | |
|---|---|---|---|---|---|---|---|
| Gr. | Treatment | 0 | 2 | 4 | 7 | 9 | 11 | 14 |
| 1 | Vehicle, qw | 161 ± 2 | 270 ± 14 | 357 ± 14 | 448 ± 17 | 570 ± 16 | 720 ± 36 | 948 ± 61 |
| 2 | BCY8245, 3 mpk, qw | 160 ± 5 | 220 ± 11 | 266 ± 15 | 218 ± 23 | 167 ± 10 | 161 ± 36 | 149 ± 43 |
| 3 | BCY8245, 3 mpk, biw | 162 ± 13 | 243 ± 19 | 211 ± 12 | 101 ± 11 | 100 ± 8 | 87 ± 7 | 65 ± 3 |
| 4 | BCY8245, 5 mpk, qw | 160 ± 9 | 176 ± 7 | 191 ± 3 | 105 ± 8 | 82 ± 3 | 91 ± 14 | 83 ± 8 |

5.3. Tumor Growth Inhibition Analysis

Tumor growth inhibition rate for test articles in the NCI-H292 xenograft model was calculated based on tumor volume measurements at day 14 after the start of treatment.

TABLE 31

Tumor growth inhibition analysis

| Gr | Treatment | Tumor Volume (mm³)$^a$ | T/C$^b$ (%) | TGI (%) | P value compared with vehicle |
|---|---|---|---|---|---|
| 1 | Vehicle, qw | 948 ± 61 | — | — | — |
| 2 | BCY8245, 3 mpk, qw | 149 ± 43 | 15.8 | 101.4 | p < 0.001 |
| 3 | BCY8245, 3 mpk, biw | 65 ± 3 | 6.9 | 112.2 | p < 0.001 |
| 4 | BCY8245, 5 mpk, qw | 83 ± 8 | 8.8 | 109.8 | p < 0.001 |

$^a$Mean ± SEM.
$^b$Tumor Growth Inhibition is calculated by dividing the group average tumor volume for the treated group by the group average tumor volume for the control group (T/C).

6. Results Summary and Discussion

In this study, the therapeutic efficacy of test articles in the NCI-H292 xenograft model was evaluated. The measured tumor volumes of all treatment groups at various time points are shown in FIG. 21 and Tables 30 and 31.

The mean tumor size of vehicle treated mice reached 948 mm³ on day 14. BCY8245 at 3 mg/kg, qw (TV=149 mm³, TGI=101.4%, p<0.001), 3 mg/kg, biw (TV=65 mm³, TGI=112.2%, p<0.001) and 5 mg/kg, qw (TV=83 mm³, TGI=109.8%, p<0.001) produced significant antitumor activity.

All of the test articles at 3 mg/kg, qw, 3 mg/kg, biw and 5 mg/kg, qw showed comparable antitumor activity, the efficacy didn't further improve when increasing the dosage or dose-frequency.

In this study, mice in all groups maintained the body-weight well.

In this cell line, which shows high expression of Nectin-4 in FACS studies, BCY8245 causes regression of the tumor emphasizing the target driven nature of optimal efficacy.

Example 9.6: In Vivo Efficacy Study of Test Articles in Treatment of NCI-H526 Xenograft in Balb/c Nude Mice 1. Study Objective The objective of the research is to evaluate the in vivo anti-tumor efficacy of test articles in treatment of NCI-H526 xenograft in Balb/c nude mice.

2. Experimental Design

| Group | Treatment | n | Dose (mg/kg) | Dosing Volume (µl/g) | Dosing Route | Schedule |
|---|---|---|---|---|---|---|
| 1 | Vehicle | 3 | — | 10 | iv | qw |
| 2 | BCY8245 | 3 | 3 | 10 | iv | qw |
| 3 | BCY8245 | 3 | 3 | 10 | iv | biw |
| 4 | BCY8245 | 3 | 5 | 10 | iv | qw |

3. Materials
3.1. Animals and Housing Condition
3.1.1. Animals
Species: *Mus Musculus*
Strain: Balb/c nude
Age: 6-8 weeks
Sex: female
Body weight: 18-22 g
Number of animals: 21 mice plus spare
3.1.2. Housing Condition
The mice were kept in individual ventilation cages at constant temperature and humidity with 3 animals in each cage.
Temperature: 20~26° C.
Humidity 40-70%.
Cages: Made of polycarbonate. The size is 300 mm×180 mm×150 mm. The bedding material is corn cob, which is changed twice per week.
Diet: Animals had free access to irradiation sterilized dry granule food during the entire study period.
Water: Animals had free access to sterile drinking water.
Cage identification: The identification labels for each cage contained the following information: number of animals, sex, strain, the date received, treatment, study number, group number and the starting date of the treatment.
Animal identification: Animals were marked by ear coding.
4. Experimental Methods and Procedures
4.1 Cell Culture
The NCI-H526 cells were maintained in medium supplemented with 10% heat inactivated fetal bovine serum at 37° C. in an atmosphere of 5% $CO_2$ in air. The tumor cells were routinely subcultured twice weekly. The cells growing in an exponential growth phase were harvested and counted for tumor inoculation.
4.2. Tumor Inoculation
Each mouse was inoculated subcutaneously at the right flank with NCI-H526 tumor cells ($5.0 \times 10^6$) in 0.2 ml of PBS for tumor development. 21 animals were randomized when the average tumor volume reached 181 mm³. The test article administration and the animal numbers in each group were shown in the experimental design table.

4.3. Testing Article Formulation Preparation

| Test article | Con. (mg/ml) | Formulation |
|---|---|---|
| Vehicle | — | 25 mM Histidine pH 7 10% sucrose |
| BCY8245 | 0.5 | Dilute 400 μl 1 mg/ml BCY8245 stock with 400 μl Histidine buffer |
| BCY8245 | 0.3 | Dilute 240 μl 1 mg/ml BCY8245 stock with 560 μl Histidine buffer |

4.4. Sample Collection

At the end of study on day 14, all tumors were collected for FFPE.

5. Results

5.1. Tumor Growth Curves

Figure 22:
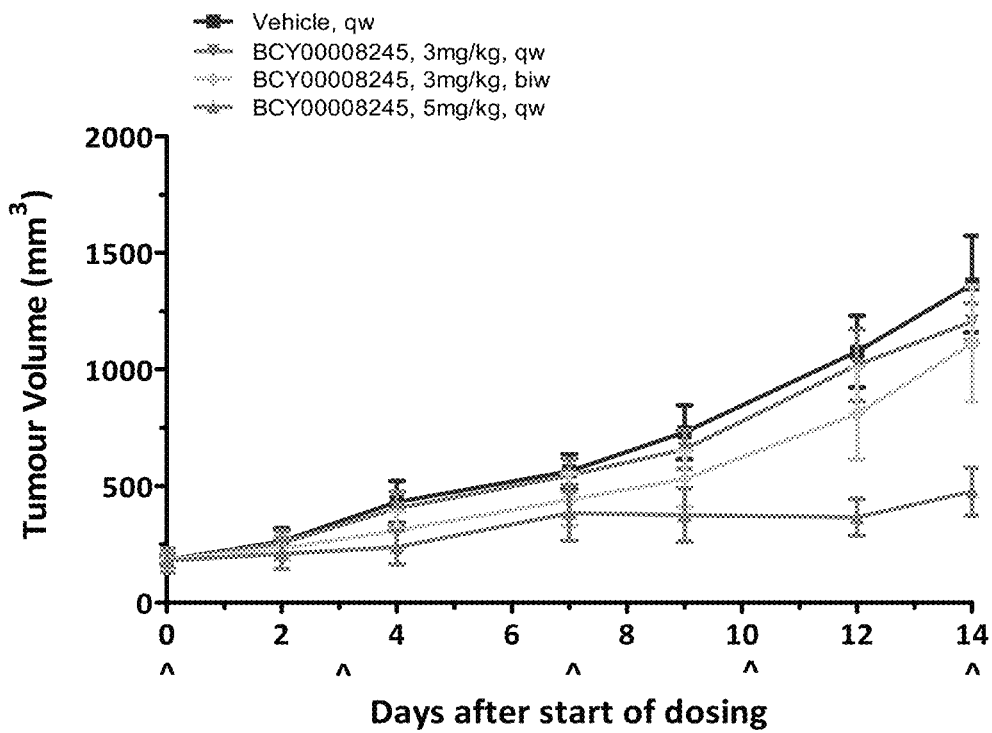
FIG. 22: Tumor volume trace after administering BCY8245 to female Balb/c nude mice bearing NCI-H526 xenograft.

The tumor growth curve is shown in FIG. 22.

5.2. Tumor Volume Trace

Mean tumor volume over time in female Balb/c nude mice bearing NCI-H526 xenograft is shown in Table 32.

TABLE 32

Tumor volume trace over time

| | | Days after the start of treatment | | | | | |
|---|---|---|---|---|---|---|---|
| Group | Treatment | 0 | 2 | 4 | 7 | 9 | 12 | 14 |
| 1 | Vehicle, qw | 181 ± 32 | 262 ± 56 | 431 ± 90 | 563 ± 72 | 729 ± 115 | 1076 ± 155 | 1365 ± 208 |
| 2 | BCY8245, 3 mpk, qw | 180 ± 32 | 256 ± 51 | 403 ± 72 | 545 ± 68 | 657 ± 83 | 1019 ± 155 | 1205 ± 79 |
| 3 | BCY8245, 3 mpk, biw | 182 ± 43 | 232 ± 49 | 308 ± 79 | 440 ± 112 | 530 ± 121 | 810 ± 197 | 1109 ± 250 |
| 4 | BCY8245, 5 mpk, qw | 180 ± 52 | 209 ± 66 | 236 ± 72 | 383 ± 119 | 375 ± 115 | 365 ± 79 | 476 ± 103 |

5.3. Tumor Growth Inhibition Analysis

Tumor growth inhibition rate for test articles in the NCI-H526 xenograft model was calculated based on tumor volume measurements at day 14 after the start of the treatment.

TABLE 33

Tumor growth inhibition analysis

| Group | Treatment | Tumor Volume (mm³)[a] | T/C[b] (%) | TGI (%) | P value |
|---|---|---|---|---|---|
| 1 | Vehicle, qw | 1365 ± 208 | — | — | — |
| 2 | BCY8245, 3 mpk, qw | 1205 ± 79 | 88.3 | 13.4 | p > 0.05 |
| 3 | BCY8245, 3 mpk, biw | 1109 ± 250 | 81.3 | 21.6 | p > 0.05 |
| 4 | BCY8245, 5 mpk, qw | 476 ± 103 | 34.9 | 75.0 | p < 0.01 |

[a]Mean ± SEM;
[b]Tumor Growth Inhibition is calculated by dividing the group average tumor volume for the treated group by the group average tumor volume for the control group (T/C).

6. Results Summary and Discussion

In this study, the therapeutic efficacy of test articles in the NCI-H526 xenograft model was evaluated. The measured tumor volumes of all treatment groups at various time points are shown in FIG. 22 and Tables 32 and 33.

The mean tumor size of vehicle treated mice reached $1365^3$ on day 14 after the start of treatment. BCY8245 at 3 mg/kg, qw (TV=1205 mm³, TGI=13.4%, p>0.05) and 3 mg/kg, biw (TV=1109 mm³, TGI=21.6%, p>0.05) showed slight antitumor activity, BCY8245 at 5 mg/kg, qw (TV=476 mm³, TGI=75.0%, p<0.01) showed significant antitumor activity. In this study, BCY8245 at 5 mg/kg biw caused over 10% animal bodyweight loss. In this cell line, which shows minimal expression of Nectin-4 in FACS studies, tumor growth is restrained by BCY8245 but the tumor does not undergo regression, emphasising the target driven requirement for optimal efficacy.

Example 9.7: In Vivo Efficacy Study of Test Articles in Treatment of Panc2.13 Xenograft in Balb/c Nude Mice

1. Study Objective

The objective of the research is to evaluate the in vivo anti-tumor efficacy of test articles in treatment of Panc2.13 xenograft in Balb/c nude mice.

2. Experimental Design

| Group | Treatment | n | Dose (mg/kg) | Dosing Volume (μl/g) | Dosing Route | Schedule |
|---|---|---|---|---|---|---|
| 1 | Vehicle | 5 | — | 10 | iv | qw |
| 2 | BCY8245 | 3 | 3 mg/kg | 10 | iv | qw |
| 3 | BCY8245 | 3 | 3 mg/kg | 10 | iv | biw |
| 4 | BCY8245 | 3 | 5 mg/kg | 10 | iv | qw |

3. Materials

3.1. Animals and Housing Condition

3.1.1. Animals

Species: *Mus Musculus*

Strain: Balb/c nude

Age: 6-8 weeks

Sex: female

Body weight: 18-22 g

Number of animals: 41 mice plus spare

3.1.2. Housing Condition

The mice were kept in individual ventilation cages at constant temperature and humidity with 3 or 5 animals in each cage.

Temperature: 20~26° C.

Humidity 40-70%.

Cages: Made of polycarbonate. The size is 300 mm×180 mm×150 mm. The bedding material is corn cob, which is changed twice per week.

Diet: Animals had free access to irradiation sterilized dry granule food during the entire study period.
Water: Animals had free access to sterile drinking water.
Cage identification: The identification labels for each cage contained the following information: number of animals, sex, strain, the date received, treatment, study number, group number and the starting date of the treatment.
Animal identification: Animals were marked by ear coding.

4. Experimental Methods and Procedures 4.1. Cell Culture

The Panc2.13 tumor cells will be maintained in RMPI1640 medium supplemented with 15% heat inactivated fetal bovine serum and 10 units/ml human recombinant insulin at 37° C. in an atmosphere of 5% $CO_2$ in air. The tumor cells will be routinely subcultured twice weekly. The cells growing in an exponential growth phase will be harvested and counted for tumor inoculation.

4.2. Tumor Inoculation

Each mouse was inoculated subcutaneously at the right flank with Panc2.13 tumor cells ($5\times10^6$) with Matrigel (1:1) in 0.2 ml of PBS for tumor development. 41 animals were randomized when the average tumor volume reached 149 $mm^3$. The test article administration and the animal numbers in each group were shown in the experimental design table.

4.3. Testing Article Formulation Preparation

| Test article | Con. (mg/ml) | Formulation |
|---|---|---|
| Vehicle | — | 25 mM Histidine pH 7 10% sucrose |
| BCY8245 | 0.5 | Dilute 400 µl 1 mg/ml BCY8245 stock with 400 µl Histidine buffer |
| BCY8245 | 0.3 | Dilute 240 µl 1 mg/ml BCY8245 stock with 560 µl Histidine buffer |

4.4. Sample Collection

At the end of study, the tumor of all groups were collected at 2 h post last dosing.

5. Results 5.1. Tumor Growth Curves

Figure 23:
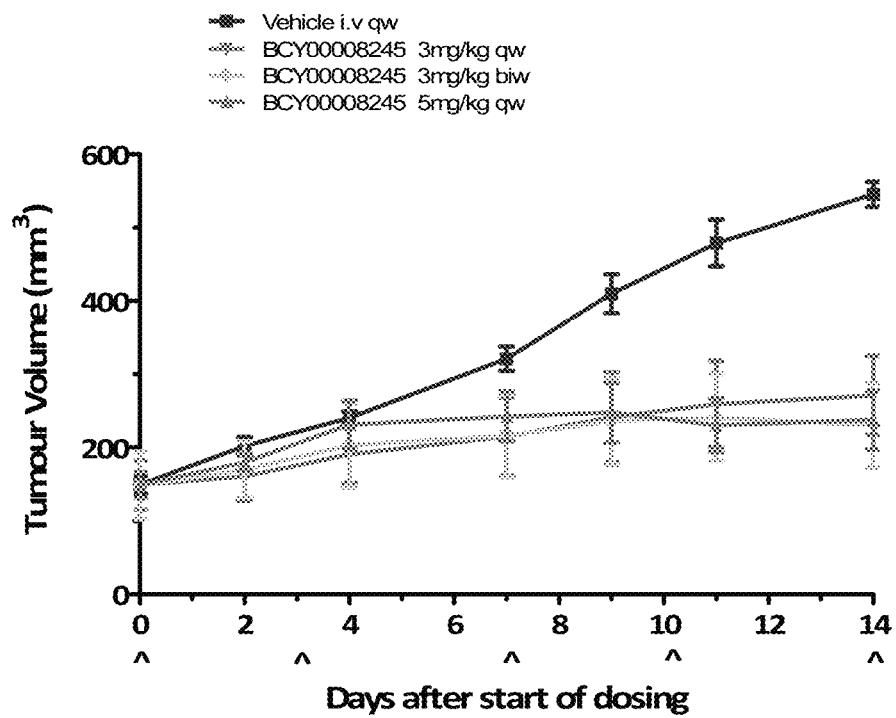
FIG. 23: Tumor volume trace after administering BCY8245 to female Balb/c nude mice bearing Panc2.13 xenograft.

The tumor growth curve is shown in FIG. 23.

5.2. Tumor Volume Trace

Mean tumor volume over time in female Balb/c nude mice bearing Panc2.13 xenograft is shown in Table 34.

5.3. Tumor Growth Inhibition Analysis

Tumor growth inhibition rate for Test articles in the Panc2.13 xenograft model was calculated based on tumor volume measurements at day 14 after the start of treatment.

TABLE 35

Tumor growth inhibition analysis

| Gr | Treatment | Tumor Volume $(mm^3)^a$ | $T/C^b$ (%) | TGI (%) | P value compared with vehicle |
|---|---|---|---|---|---|
| 1 | Vehicle, qw | 545 ± 17 | — | — | — |
| 2 | BCY8245, 3 mpk, qw | 271 ± 54 | 49.6 | 69.2 | p < 0.01 |
| 3 | BCY8245, 3 mpk, biw | 231 ± 57 | 42.3 | 79.1 | p < 0.001 |
| 4 | BCY8245, 5 mpk, qw | 238 ± 40 | 43.6 | 77.5 | p < 0.001 |

$^a$Mean ± SEM.
$^b$Tumor Growth Inhibition is calculated by dividing the group average tumor volume for the treated group by the group average tumor volume for the control group (T/C).

6. Results Summary and Discussion

In this study, the therapeutic efficacy of test articles in the Panc2.13 xenograft model was evaluated. The measured tumor volumes of all treatment groups at various time points are shown in FIG. 23 and Tables 34 and 35.

The mean tumor size of vehicle treated mice reached 545 $mm^3$ on day 14. BCY8245 at 3 mg/kg, qw (TV=271 $mm^3$, TGI=69.2%, p<0.01), 3 mg/kg, biw (TV=231 $mm^3$, TGI=79.1%, p<0.001) and 5 mg/kg, qw (TV=238 $mm^3$, TGI=77.5%, p<0.001) produced significant antitumor activity. In this study, animals in all of 5 mg/kg qw groups lost over average 15% bodyweight. In this cell line, which shows only moderate expression of Nectin-4 in FACS studies, tumor growth is restrained by BCY8245 but the tumor does not undergo regression.

Example 9.8: In Vivo Efficacy Study of Test Articles in Treatment of MDA-MB-468 Xenograft in Balb/c Nude Mice 1. Study Objective The objective of the research is to evaluate the in vivo anti-tumor efficacy of BCY8245 and BCY8245 in combi-

TABLE 34

Tumor volume trace over time

| | | Days after the start of treatment | | | | | | |
|---|---|---|---|---|---|---|---|---|
| Gr. | Treatment | 0 | 2 | 4 | 7 | 9 | 11 | 14 |
| 1 | Vehicle, qw | 149 ± 12 | 202 ± 12 | 240 ± 9 | 321 ± 17 | 410 ± 27 | 479 ± 32 | 545 ± 17 |
| 2 | BCY8245, 3 mpk, qw | 149 ± 34 | 160 ± 33 | 191 ± 39 | 215 ± 53 | 242 ± 62 | 259 ± 59 | 271 ± 54 |
| 3 | BCY8245, 3 mpk, biw | 148 ± 46 | 170 ± 38 | 204 ± 57 | 216 ± 56 | 236 ± 59 | 241 ± 60 | 231 ± 57 |
| 4 | BCY8245, 5 mpk, qw | 149 ± 18 | 180 ± 11 | 231 ± 33 | 242 ± 34 | 248 ± 40 | 231 ± 37 | 238 ± 40 | nation with BCY8234 in treatment of MDA-MB-468 xenograft in Balb/c nude mice to determine the role target binding has to play in optimal efficacy.

2. Experimental Design

| Group | Treatment | Dose (mg/kg) | N | Dosing Route | Schedule |
|---|---|---|---|---|---|
| 1 | Vehicle | — | 4 | i.v. | Qw, 3 weeks |
| 2 | BCY8245 | 0.3 | 4 | i.v. | Qw, 3 weeks |
| 3 | BCY8245 | 1 | 4 | i.v. | Qw, 3 weeks |
| 4 | BCY8245 | 3 | 4 | i.v. | Qw, 3 weeks |
| 5 | BCY8245 + BCY8234 | 1 + 300 | 4 | i.v. | Qw, 3 weeks |
| 6 | BCY8245 + BCY8234 | 3 + 300 | 4 | i.v. | Qw, 3 weeks |

Note:
N, the number of animals in each group.

3. Materials 3.1. Animals and Housing Condition 3.1.1. Animals

Species: *Mus Musculus*

Strain: Balb/c nude

Age: 6-8 weeks

Sex: female

Body weight: 18-22 g

Number of animals: 36 mice plus spare 3.1.2. Housing Condition

The mice were kept in individual ventilation cages at constant temperature and humidity with 4 animals in each cage.

Temperature: 20~26° C.

Humidity 40-70%.

Cages: Made of polycarbonate. The size is 300 mm×180 mm×150 mm. The bedding material is corn cob, which is changed twice per week.

Diet: Animals had free access to irradiation sterilized dry granule food during the entire study period.

Water: Animals had free access to sterile drinking water.

Cage identification: The identification labels for each cage contained the following information: number of animals, sex, strain, the date received, treatment, study number, group number and the starting date of the treatment.

Animal identification: Animals were marked by ear coding.

4. Experimental Methods and Procedures 4.1. Cell Culture

The tumor cells were maintained in Leibovitz's L-15 medium supplemented with 10% heat inactivated fetal bovine serum at 37° C. in an atmosphere of 0% $CO_2$ in air. The tumor cells were routinely subcultured twice weekly. The cells growing in an exponential growth phase were harvested and counted for tumor inoculation.

4.2. Tumor Inoculation

Each mouse was inoculated subcutaneously at the right flank with MDA-MB-468 tumor cells ($10 \times 10^6$) in 0.2 ml of PBS supplemented with 50% matrigel for tumor development. 36 animals were randomized when the average tumor volume reached 186 $mm^3$. The test article administration and the animal numbers in each group were shown in the experimental design table.

4.3. Testing Article Formulation Preparation

| Test article | Purity | Conc. (mg/ml) | Formulation |
|---|---|---|---|
| Vehicle | — | — | 25 mM Histidine, pH 7 10% sucrose |
| BCY8245 | 99.4% | 1 | Dissolve 5.0 mg BCY8245 in 4.97 ml Histidine buffer[1] |
| | | 0.03 | Dilute 36 μl 1 mg/ml BCY8245 stock with 1164 μl Histidine buffer |
| | | 0.1 | Dilute 120 μl 1 mg/ml BCY8245 stock with 1080 μl Histidine buffer |
| | | 0.3 | Dilute 360 μl 1 mg/ml BCY8245 stock with 840 μl Histidine buffer |
| BCY8234 | 98.10% | 30 | Dissolve 147 mg BCY8234 in 4.807 ml Histidine buffer |

4.4. Sample Collection

At the day 21 of study, the tumors of group 5 and 6 were collected for FFPE. At the end of the study, the tumors of group 3 was collected for FFPE.

5. Results 5.1. Tumor Growth Curve

Figure 24:
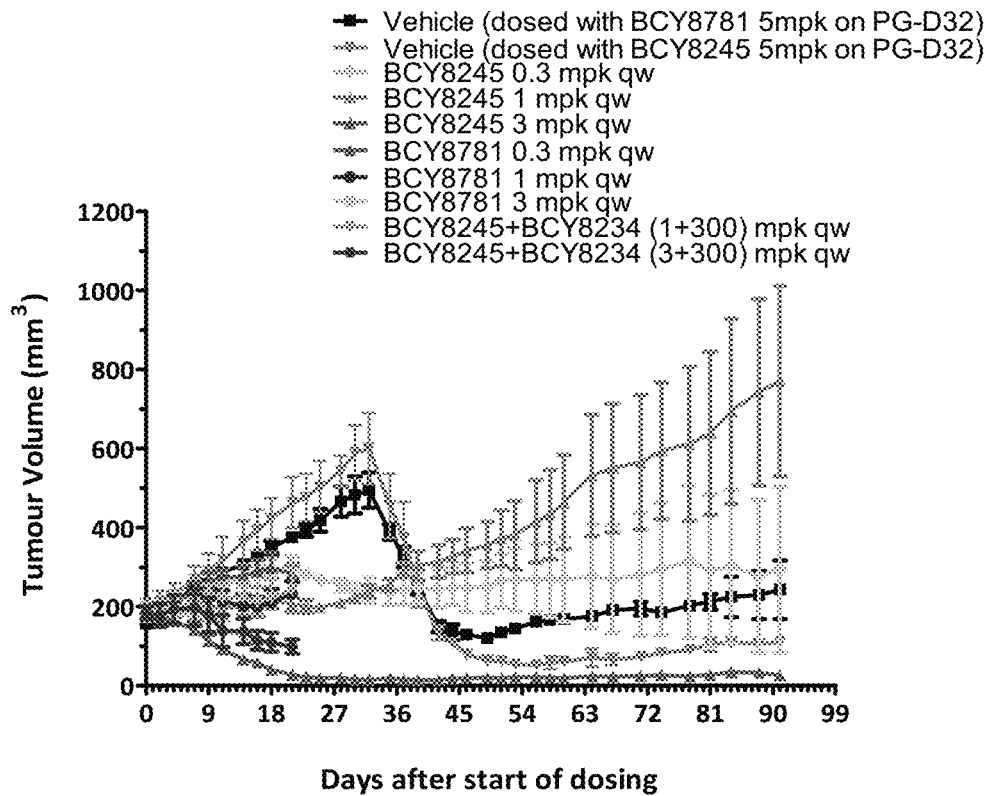
FIG. 24: Tumor volume traces after administering BCY8245 or BCY8245 in combination with BCY8234 to female Balb/c nude mice bearing MDA-MB-468 xenograft.

The tumor growth curve is shown in FIG. 24.

5.2. Tumor Volume Trace

Mean tumor volume over time in female Balb/c nude mice bearing MDA-MB-468 xenograft is shown in Tables 36 to 38.

5.3. Tumor Growth Inhibition Analysis

Tumor growth inhibition rate for test articles in the MDA-MB-468 xenograft model was calculated based on tumor volume measurements at day 21 after the start of the treatment.

6. Results Summary and Discussion

In this study, the therapeutic efficacy of test articles in the MDA-MB-468 xenograft model was evaluated. The measured tumor volumes of all treatment groups at various time points are shown in FIG. 24 and Tables 36 to 39.

The mean tumor size of vehicle treated mice reached 420 $mm^3$ on day 21. BCY8245 at 1 mg/kg, qw (TV=204 $mm^3$, TGI=92.1%, p<0.001), 3 mg/kg, qw (TV=27 $mm^3$, TGI=164.9%, p<0.001) produced significant anti-tumor activity in dose-dependent manner. BCY8245 at 0.3 mg/kg qw or biw did not show any anti-tumor activity.

BCY8245 at 1 mg/kg, qw and 3 mg/kg, qw in combination with BCY8234 (the toxin free cognate peptide) 300 mg/kg, qw produced significant anti-tumor activity (TV=242 $mm^3$, TGI=75.4%, p<0.01) produced significant anti-tumor activity. When comparing with BCY8245 alone, the anti-tumor activity of BCY8245 at 3 mg/kg was antagonized by BCY8234 at 300 mg/kg (p<0.001). This reduction in efficacy by the competing toxin-free peptide demonstrates the importance of target binding for optimal efficacy. During the following monitoring schedule, the mice treated with BCY8245 1 mg/kg qw showed obvious tumor relapse, while the mice treated with BCY8245 3 mg/kg qw didn't show any tumor relapse.

TABLE 36

Tumor volume trace over time (Day 0 to day 21)

| | | Days after the start of treatment | | | | | | | | | |
|---|---|---|---|---|---|---|---|---|---|---|---|
| Gr. | Treatment | 0 | 2 | 4 | 7 | 9 | 11 | 14 | 16 | 18 | 21 |
| 1 | Vehicle, qw | 182 ± 15 | 196 ± 18 | 217 ± 18 | 260 ± 15 | 283 ± 19 | 302 ± 26 | 335 ± 27 | 362 ± 28 | 386 ± 31 | 420 ± 37 |
| 2 | BCY8245 0.3 mpk, qw | 188 ± 21 | 189 ± 19 | 211 ± 21 | 235 ± 28 | 252 ± 25 | 253 ± 33 | 275 ± 26 | 277 ± 27 | 295 ± 26 | 300 ± 27 |
| 3 | BCY8245 1 mpk, qw | 185 ± 21 | 187 ± 22 | 183 ± 22 | 190 ± 28 | 205 ± 29 | 195 ± 27 | 201 ± 25 | 197 ± 22 | 218 ± 24 | 204 ± 19 |
| 4 | BCY8245 3 mpk, qw | 181 ± 14 | 171 ± 17 | 163 ± 10 | 141 ± 21 | 113 ± 16 | 92 ± 5 | 66 ± 4 | 58 ± 2 | 41 ± 2 | 27 ± 1 |
| 5 | BCY8245 + BCY8234 1 + 300 mpk, qw | 184 ± 15 | 189 ± 22 | 194 ± 28 | 212 ± 30 | 221 ± 34 | 221 ± 39 | 223 ± 36 | 211 ± 38 | 221 ± 51 | 242 ± 67 |
| 6 | BCY8245 + BCY8234 3 + 300 mpk, qw | 184 ± 16 | 178 ± 57 | 193 ± 36 | 197 ± 46 | 179 ± 44 | 138 ± 41 | 137 ± 32 | 114 ± 24 | 110 ± 24 | 99 ± 18 |

TABLE 37

Tumor volume trace over time (Day 23 to day 32)

| | | Days after the start of treatment | | | | |
|---|---|---|---|---|---|---|
| Gr. | Treatment | 23 | 25 | 28 | 30 | 32 |
| 1 | Vehicle, qw | 434 ± 35 | 460 ± 38 | 504 ± 32 | 535 ± 46 | 548 ± 51 |
| 2 | BCY8245 0.3 mpk, qw | 284 ± 14 | 268 ± 10 | 254 ± 15 | 240 ± 21 | 241 ± 32 |
| 3 | BCY8245 1 mpk, qw | 200 ± 16 | 199 ± 13 | 210 ± 6 | 221 ± 14 | 239 ± 16 |
| 4 | BCY8245 3 mpk, qw | 22 ± 3 | 19 ± 3 | 20 ± 3 | 15 ± 2 | 15 ± 1 |

TABLE 38

Tumor volume trace over time (Day 35 to day 91)

| Days | Group 1, Vehicle, qw, dosed with BCY8245 5 mpk on PG-D32 | Group 2, BCY8245, 0.3 mpk, qw | Group 3 BCY8245, 1 mpk, qw | Group 4, BCY8245, 3 mpk, qw |
|---|---|---|---|---|
| 35 | 455 ± 81 | 237 ± 33 | 255 ± 15 | 19 ± 2 |
| 37 | 373 ± 92 | 246 ± 40 | 292 ± 19 | 16 ± 2 |
| 39 | 247 ± 48 | 248 ± 37 | 304 ± 36 | 14 ± 1 |
| 42 | 134 ± 18 | 245 ± 48 | 314 ± 42 | 14 ± 2 |
| 44 | 108 ± 3 | 251 ± 48 | 327 ± 42 | 18 ± 4 |
| 46 | 79 ± 3 | 248 ± 61 | 342 ± 55 | 19 ± 4 |
| 49 | 63 ± 8 | 250 ± 65 | 356 ± 59 | 20 ± 4 |
| 51 | 62 ± 5 | 264 ± 68 | 374 ± 71 | 18 ± 5 |
| 53 | 53 ± 12 | 268 ± 81 | 381 ± 87 | 22 ± 4 |
| 56 | 52 ± 13 | 271 ± 87 | 416 ± 104 | 21 ± 4 |
| 58 | 58 ± 0 | 267 ± 95 | 433 ± 113 | 20 ± 5 |
| 60 | 61 ± 7 | 270 ± 108 | 464 ± 119 | 18 ± 6 |
| 64 | 71 ± 23 | 276 ± 132 | 532 ± 154 | 23 ± 6 |
| 67 | 66 ± 14 | 269 ± 137 | 550 ± 162 | 23 ± 5 |
| 71 | 73 ± 5 | 280 ± 155 | 565 ± 170 | 24 ± 7 |
| 74 | 82 ± 4 | 295 ± 167 | 594 ± 173 | 27 ± 8 |
| 78 | 90 ± 8 | 313 ± 194 | 612 ± 195 | 23 ± 6 |
| 81 | 104 ± 17 | 291 ± 192 | 639 ± 206 | 27 ± 8 |
| 84 | 110 ± 1 | 301 ± 194 | 695 ± 234 | 34 ± 7 |
| 88 | 106 ± 7 | 277 ± 194 | 743 ± 236 | 32 ± 7 |
| 91 | 110 ± 3 | 293 ± 209 | 771 ± 240 | 26 ± 6 |

TABLE 39

Tumor growth inhibition analysis

| Gr | Treatment | Tumor Volume $(mm^3)^a$ | $T/C^b$ (%) | TGI (%) | P value compared with vehicle | Combo compared With BCY8245 |
|---|---|---|---|---|---|---|
| 1 | Vehicle, qw | 420 ± 37 | — | — | — | — |
| 2 | BCY8245 0.3 mpk, qw | 300 ± 27 | 71.4 | 52.7 | p > 0.05 | — |
| 3 | BCY8245 1 mpk, qw | 204 ± 19 | 48.6 | 92.1 | p < 0.001 | — |
| 4 | BCY8245 3 mpk, qw | 27 ± 1 | 6.5 | 164.9 | p < 0.001 | — |
| 5 | BCY8245 + BCY8234 1 + 300 mpk, qw | 242 ± 67 | 57.8 | 75.4 | p < 0.01 | p > 0.05 |
| 6 | BCY8245 + BCY8234 3 + 300 mpk, qw | 99 ± 18 | 23.5 | 135.9 | p < 0.001 | P < 0.001 |

$^a$Mean ± SEM.
$^b$Tumor Growth Inhibition is calculated by dividing the group average tumor volume for the treated group by the group average tumor volume for the control group (T/C).

Example 9.9: In Vivo Efficacy Study of Test Articles in Treatment of MDA-MB-468 Xenograft in Balb/c Nude Mice 1. Study Objective The objective of the research is to evaluate the in vivo anti-tumor efficacy of BCY8245 alone or in combination with BCY8234 in treatment of MDA-MB-468 xenograft in Balb/c nude mice.

2. Experimental Design

| Group | Treatment | Dose (mg/kg) | N | Route | Dosing Schedule |
|---|---|---|---|---|---|
| 1 | Vehicle | — | 5 | i.v. | Qw, 3 |
| 2 | BCY8245 | 1 | 5 | i.v. | Qw, 3 |
| 3 | BCY8245 | 3 | 5 | i.v. | Qw, 3 |
| 4 | BCY8245 + BCY8234 | 3 + 300 = 300 | 5 | i.v. | Qw, 3 weeks |

Note:
N, the number of animals in each group.

3. Materials
3.1 Animals and Housing Condition
3.1.1. Animals
Species: *Mus Musculus*
Strain: Balb/c nude
Age: 6-8 weeks
Sex: female
Body weight: 18-22 g
Number of animals: 20 mice plus spare

3.1.2. Housing Condition
The mice were kept in individual ventilation cages at constant temperature and humidity with 5 animals in each cage.
Temperature: 20~26° C.
Humidity 40-70%.
Cages: Made of polycarbonate. The size is 300 mm×180 mm×150 mm. The bedding material is corn cob, which is changed twice per week.
Diet: Animals had free access to irradiation sterilized dry granule food during the entire study period.
Water: Animals had free access to sterile drinking water.
Cage identification: The identification labels for each cage contained the following information: number of animals, sex, strain, the date received, treatment, study number, group number and the starting date of the treatment.
Animal identification: Animals were marked by ear coding.

4. Experimental Methods and Procedures
4.1 Cell Culture
The tumor cells were maintained in Leibovitz's L-15 medium supplemented with 10% heat inactivated fetal bovine serum at 37° C. in an atmosphere of 0% $CO_2$ in air. The tumor cells were routinely subcultured twice weekly. The cells growing in an exponential growth phase were harvested and counted for tumor inoculation.

4.2. Tumor Inoculation
Each mouse was inoculated subcutaneously at the right flank with MDA-MB-468 tumor cells ($10 \times 10^6$) in 0.2 ml of PBS supplemented with 50% matrigel for tumor development. 20 animals were randomized when the average tumor volume reached 464 mm³. The test article administration and the animal numbers in each group were shown in the experimental design table.

4.3. Testing Article Formulation Preparation

| Test article | Purity | Conc. (mg/ml) | Formulation |
|---|---|---|---|
| Vehicle | — | — | 25 mM Histidine pH 7 10% sucrose |
| BCY8245 | 99.7% | 1 | Dissolve 5.0 mg BCY8245 in 4.985 ml Histidine buffer[1] |
|  |  | 0.1 | Dilute 140 μl 1 mg/ml BCY8245 stock with 1260 μl Histidine buffer |
|  |  | 0.3 | Dilute 420 μl 1 mg/ml BCY8245 stock with 980 μl Histidine buffer |
| BCY8234 | 98.10% | 30 | Dissolve 147 mg BCY8234 in 4.807 ml Histidine buffer |

[1]25 mM Histidine pH 7 10% sucrose

4.4. Sample Collection
At the end of the study, the tumors of group 3 was collected for FFPE.

Figure 25:
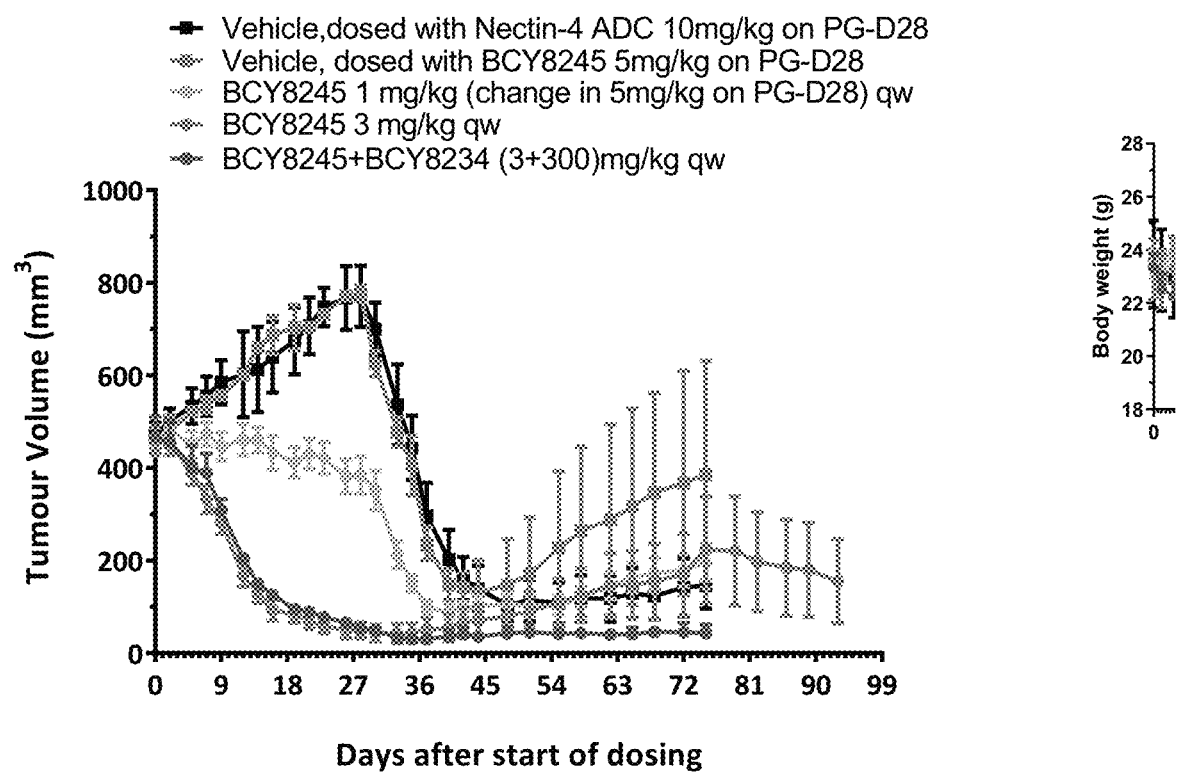
FIG. 25: Tumor volume traces after administering BCY8245 alone or BCY8245 in combination with BCY8234 to female Balb/c nude mice bearing MDA-MB-468 xenograft.

5. Results
5.1. Tumor Growth Curve
The tumor growth curve is shown in FIG. 25.

5.2. Tumor Volume Trace
Mean tumor volume over time in female Balb/c nude mice bearing MDA-MB-468 xenograft is shown in Tables 40 to 42.

5.3. Tumor Growth Inhibition Analysis
Tumor growth inhibition rate for test articles in the MDA-MB-468 xenograft model was calculated based on tumor volume measurements at day 28 after the start of the treatment.

6. Results Summary and Discussion
In this study, the therapeutic efficacy of test articles in the MDA-MB-468 xenograft model was evaluated. The measured tumor volumes of all treatment groups at various time points is shown in FIG. 25 and Tables 40 to 43.

The initial tumor starting size was intentionally greater than that previously used to determine whether BCY8245 showed efficacy in this larger size. The mean tumor size of vehicle treated mice reached 773 mm³ on day 28. BCY8245 at 1 mg/kg, qw (TV=384 mm³, TGI=126.6%, p<0.001) and 3 mg/kg, qw (TV=50 mm³, TGI=234.6%, p<0.001) produced significant anti-tumor activity in dose dependent manner on day 28. Among them, the mice treated with BCY8245, 3 mg/kg qw showed some tumor relapse after ceasing the treatment, the further dosing from day 76 didn't work on complete tumor regression.

BCY8245 at 3 mg/kg, qw in combination with BCY8234 300 mg/kg, qw produced significant anti-tumor activity (TV=55 mm³, TGI=234.0%, p<0.001) on day 28, and the tumors didn't showed any relapse during the whole monitoring schedule.

The mice of vehicle group treated with 10 mg/kg Nectin-4 ADC or 5 mg/kg BCY8245 and the mice of group 2 (BCY8245, 1 mpk, qw) treated with 5 mg/kg BCY8245 on PG-D28 showed effective tumor regression in the following 3 weeks, after then, the tumors showed regrowth in the next 4 weeks when taken off drug.

BCY8245 was able to cause tumor regression in the tumors of approximately 450 mm³, but also when administered to the group previously receiving vehicle, in tumours with a starting volume of approximately 770 mm³.

TABLE 40

Tumor volume trace over time (Day 0 to day 28)

| | | Days after the start of treatment | | | | | |
|---|---|---|---|---|---|---|---|
| Gr. | Treatment | 0 | 2 | 5 | 7 | 9 | 12 |
| 1 | Vehicle, qw | 466 ± 89 | 494 ± 94 | 529 ± 106 | 548 ± 109 | 574 ± 117 | 602 ± 130 |
| 2 | BCY8245 1 mpk, qw | 466 ± 22 | 480 ± 24 | 453 ± 29 | 474 ± 25 | 446 ± 31 | 461 ± 34 |
| 3 | BCY8245 3 mpk, qw | 464 ± 28 | 451 ± 24 | 388 ± 25 | 333 ± 30 | 284 ± 26 | 168 ± 24 |
| 4 | BCY8245 + BCY8234 (3 + 300) mpk, qw | 467 ± 45 | 457 ± 46 | 401 ± 47 | 389 ± 42 | 309 ± 25 | 205 ± 9 |

| | Days after the start of treatment | | | | | | |
|---|---|---|---|---|---|---|---|
| Gr. | 14 | 16 | 19 | 21 | 23 | 26 | 28 |
| 1 | 632 ± 133 | 659 ± 129 | 686 ± 133 | 706 ± 145 | 741 ± 148 | 769 ± 157 | 773 ± 155 |
| 2 | 460 ± 28 | 433 ± 37 | 412 ± 32 | 430 ± 32 | 421 ± 34 | 382 ± 37 | 384 ± 41 |
| 3 | 129 ± 20 | 93 ± 23 | 83 ± 17 | 71 ± 19 | 60 ± 17 | 49 ± 17 | 50 ± 17 |
| 4 | 150 ± 9 | 125 ± 5 | 95 ± 3 | 90 ± 5 | 78 ± 5 | 66 ± 4 | 55 ± 5 |

TABLE 41

Tumor volume trace over time (Day 30 to day 75)

| Days after the start of treatment | Group1 Vehicle, dosed with 5 mpk BCY8245 on PG-D28 | Group 2, BCY8245, 1 mpk, change in 5 mpk on PG-D28 | Group3, BCY8245, 3 mpk, qw | Group 4, BCY8245 + BCY8234 3 + 300 mpk, qw |
|---|---|---|---|---|
| 30 | 625 ± 27 | 351 ± 42 | 44 ± 18 | 49 ± 8 |
| 33 | 477 ± 31 | 213 ± 29 | 43 ± 20 | 33 ± 10 |
| 35 | 405 ± 65 | 151 ± 18 | 44 ± 20 | 31 ± 10 |
| 37 | 237 ± 36 | 98 ± 16 | 50 ± 24 | 31 ± 10 |
| 40 | 148 ± 33 | 89 ± 17 | 55 ± 29 | 36 ± 14 |
| 42 | 142 ± 33 | 95 ± 16 | 66 ± 32 | 40 ± 13 |
| 44 | 132 ± 69 | 103 ± 20 | 71 ± 33 | 35 ± 11 |
| 48 | 146 ± 100 | 106 ± 21 | 80 ± 36 | 43 ± 14 |
| 51 | 171 ± 122 | 103 ± 21 | 91 ± 43 | 45 ± 18 |
| 55 | 227 ± 166 | 104 ± 20 | 108 ± 53 | 42 ± 13 |
| 56 | 264 ± 182 | 120 ± 23 | 125 ± 58 | 43 ± 12 |
| 62 | 288 ± 206 | 145 ± 29 | 146 ± 70 | 40 ± 12 |
| 65 | 316 ± 212 | 163 ± 31 | 147 ± 74 | 41 ± 14 |
| 68 | 347 ± 215 | 173 ± 32 | 155 ± 81 | 46 ± 13 |
| 72 | 368 ± 242 | 180 ± 36 | 170 ± 89 | 45 ± 20 |
| 75 | 385 ± 245 | 196 ± 40 | 223 ± 115 | 43 ± 19 |

TABLE 42

Tumor volume trace over time (Day 79 to day 103)

| | | Days after the start of treatment | | | | | | |
|---|---|---|---|---|---|---|---|---|
| Gr. | Treatment | 79 | 82 | 86 | 89 | 93 | 96 | 100 | 103 |
| 3 | BCY8245 3 mpk, qw | 221 ± 118 | 198 ± 107 | 185 ± 105 | 180 ± 102 | 155 ± 91 | 166 ± 95 | 221 ± 119 | 250 ± 125 |

TABLE 43

Tumor growth inhibition analysis

| Gr | Treatment | Tumor Volume (mm³)[a] | T/C[b] (%) | TGI (%) | P value compared with vehicle |
|---|---|---|---|---|---|
| 1 | Vehicle, qw | 773 ± 155 | — | — | — |
| 2 | BCY8245 1 mpk, qw | 384 ± 41 | 49.7 | 126.6 | p < 0.001 |
| 3 | BCY8245 3 mpk, qw | 50 ± 17 | 6.4 | 234.6 | p < 0.001 |
| 4 | BCY8245 + BCY8234 3 + 300 mpk, qw | 55 ± 5 | 7.1 | 234.0 | p < 0.001 |

[a]Mean ± SEM.
[b]Tumor Growth Inhibition is calculated by dividing the group average tumor volume for the treated group by the group average tumor volume for the control group (T/C).

Example 10: In Vivo PK Studies

Figure 33:
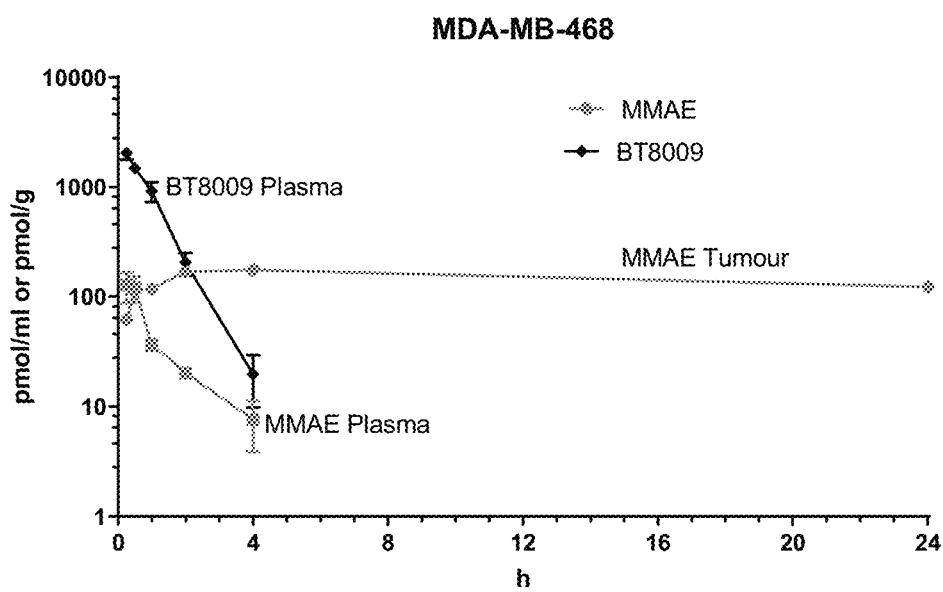
FIG. 33: MDA-MB-468 cells express Nectin-4 and show prolonged retention of MMAE in tumour.

MDA-MB-468 xenograft animals were injected with BCY8245 (BT8009) at 3 mg/kg. At various timepoints, animals were euthanized and plasma and tumour taken and snap frozen. Samples were analysed for MMAE. The plasma levels of BT8009 (BCY8245) are from historical PK studies. The concentrations of MMAE in plasma, MMAE in tumor, and BT8009 in plasma are shown in FIG. 33. MMAE was retained in the tumour longer than in plasma supporting the hypothesis that systemic exposure is significantly less than tumour exposure.

Example 11: HCS Assay

Figure 34:
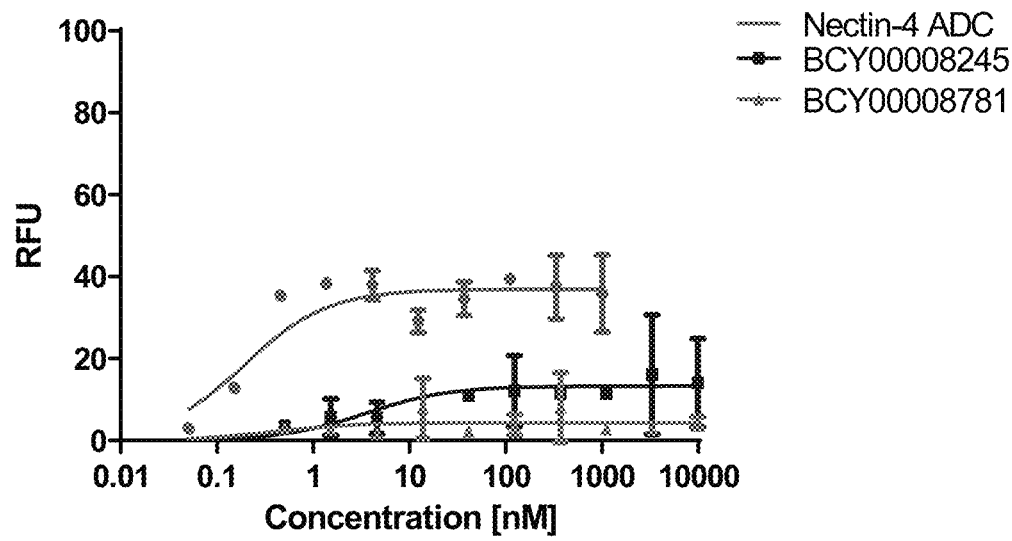
FIG. 34: HCS—Data analysis on MDA-MB-468 cell line.
Figure 34:
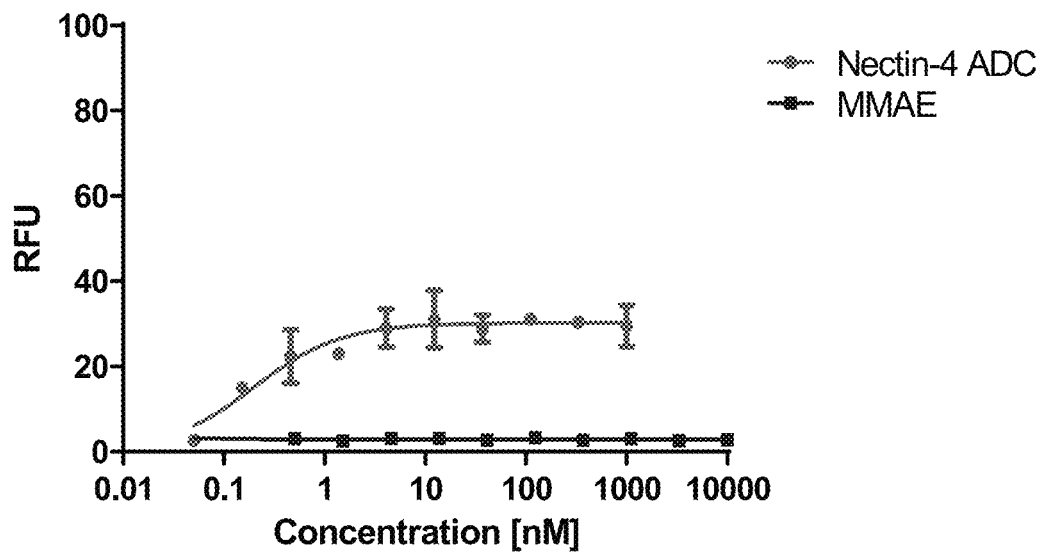

HCS assay was used in Nectin-4 BDC binding study. Cells were incubated with test agent and then washed. Detection was by a fluorescent antibody to MMAE. MDA- MB-468 cells show moderate Nectin-4 expression with 20000 cells giving the best images. NCI-H292 cells show low expression in this assay, detection of MMAE was poor even at 20000 cells. HCS Data on MDA-MB-468 cell line is shown in FIG. 34, and Table 44.

TABLE 44

| Test Item | Max fluorescent intensity | Kd (nM) | Historical Kd (nM) |
|---|---|---|---|
| Nectin-4 ADC | 33.63 | 0.2 | 0.28 ± 0.07 |
| BCY8245 | 13.34 | 3.52 | 5.18 |
| MMAE | 2.95 | >10000 | >10000 |

Nectin-4 ADC and BCY8245 were retained on the cells and co-localised with a membrane stain. BCY8781 and MMAE showed minimal retention. Kd of all compounds on MDA-MB-468 cell line were consistent with historical data. The Nectin-4 ADC showed detectable binding affinity on MDA-MB-468 cell line. BCY8425 showed single digit nanomolar affinity with a Bmax lower than for the Nectin-4 ADC. This reduced maximum fluorescent intensity is because the Nectin-4 ADC has an MMAE to drug ration of 4 whereas BCY8245 has an MMAE to drug ratio of 1. BCY8781 showed only very weak binding affinity on MDA-MB-468 cell line whilst MMAE showed almost no detectable binding affinity on MDA-MB-468 cell line.

Example 12: In Vivo Efficacy of BCY8245 in Two PDX Models of Lung Cancer

Purpose

To evaluate the efficacy of BCY8245 in a PDX model of squamous cell non-small and adenocarcinoma (both non-small cell carcinomas).

Animals
  Species: *Mus Musculus*
  Strain: Balb/c nude
  Age: 6-8 weeks
  Sex: female
  Body weight: 18-22
Agents in Test
  BCY8245 and Nectin-4 ADC or BCY8781
Pre-Study Animals Each mouse was inoculated subcutaneously at the right flank with LU-01-0007 or LU-01-0412 tumor fragment (~30 mm³) for tumor development. Animals were randomized when the average tumor volume reached 161 mm³ (LU-01-0007) or 147 mm³ (LU-01-0412)

In life Measurements and the Endpoints

Animals were checked daily for any effects of tumor growth and treatments on normal behavior such as mobility, food and water consumption (by looking only), body weight gain/loss, eye/hair matting and any other abnormal effect as stated in the protocol. Death and observed clinical signs were recorded on the basis of the numbers of animals within each subset.

The major endpoint was to see if the tumor growth could be delayed or mice could be cured. Tumor volume was measured three times weekly in two dimensions using a caliper, and the volume was expressed in mm³ using the formula: $V=0.5 \, a \times b^2$ where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day.

TGI was calculated for each group using the formula: TGI $(\%)=[1-(T_i-T_0)/(V_i-V_0)]\times 100$; $T_i$ is the average tumor volume of a treatment group on a given day, $T_0$ is the average tumor volume of the treatment group on the day of treatment start, Vi is the average tumor volume of the vehicle control group on the same day with $T_i$, and $V_0$ is the average tumor volume of the vehicle group on the day of treatment start.

Figure 26:
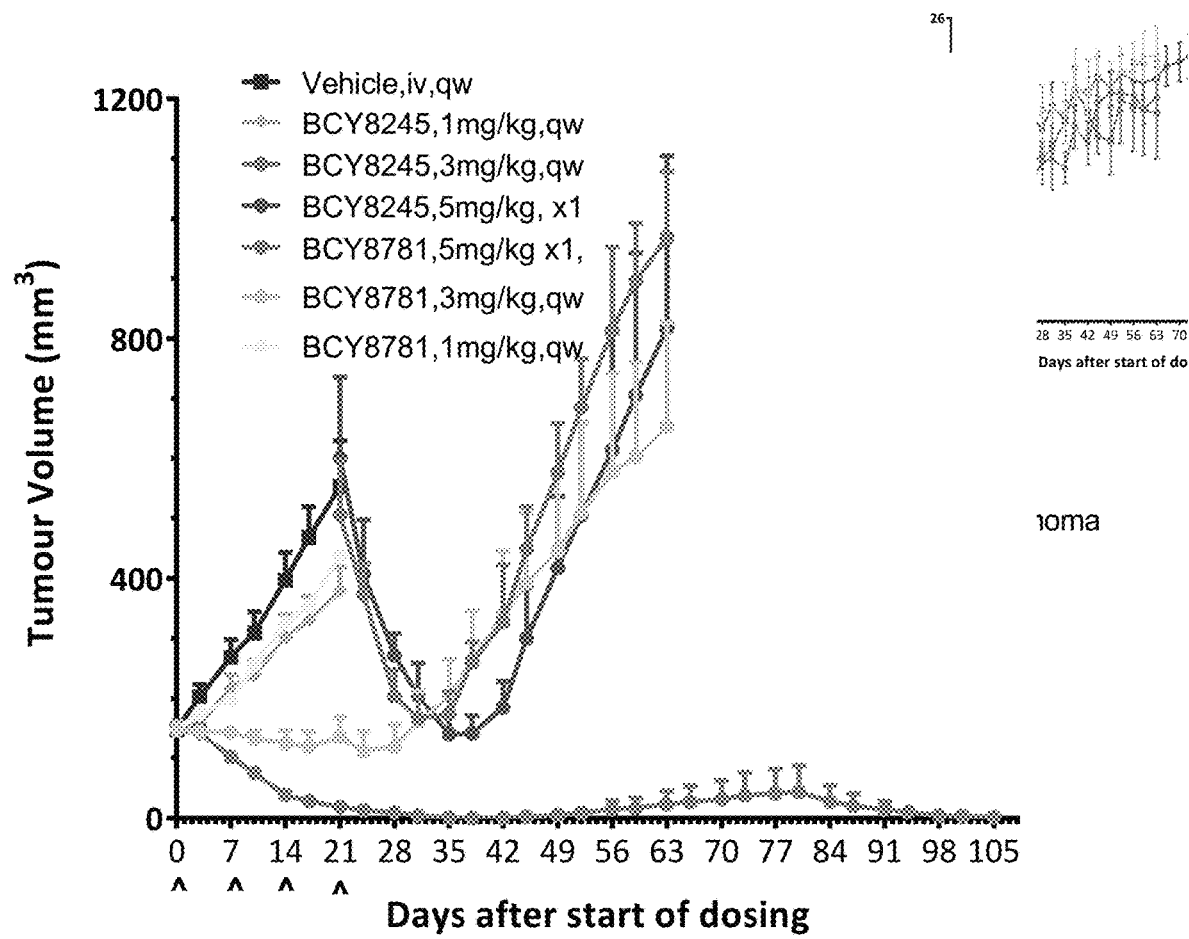
FIGS. 26-31: Tumor volume traces in Lu-01-0412, LU-01-0007, CTG-1771, CTG-1171, CTG-1106, and CTG-0896 PDX xenografts.
Figure 27:
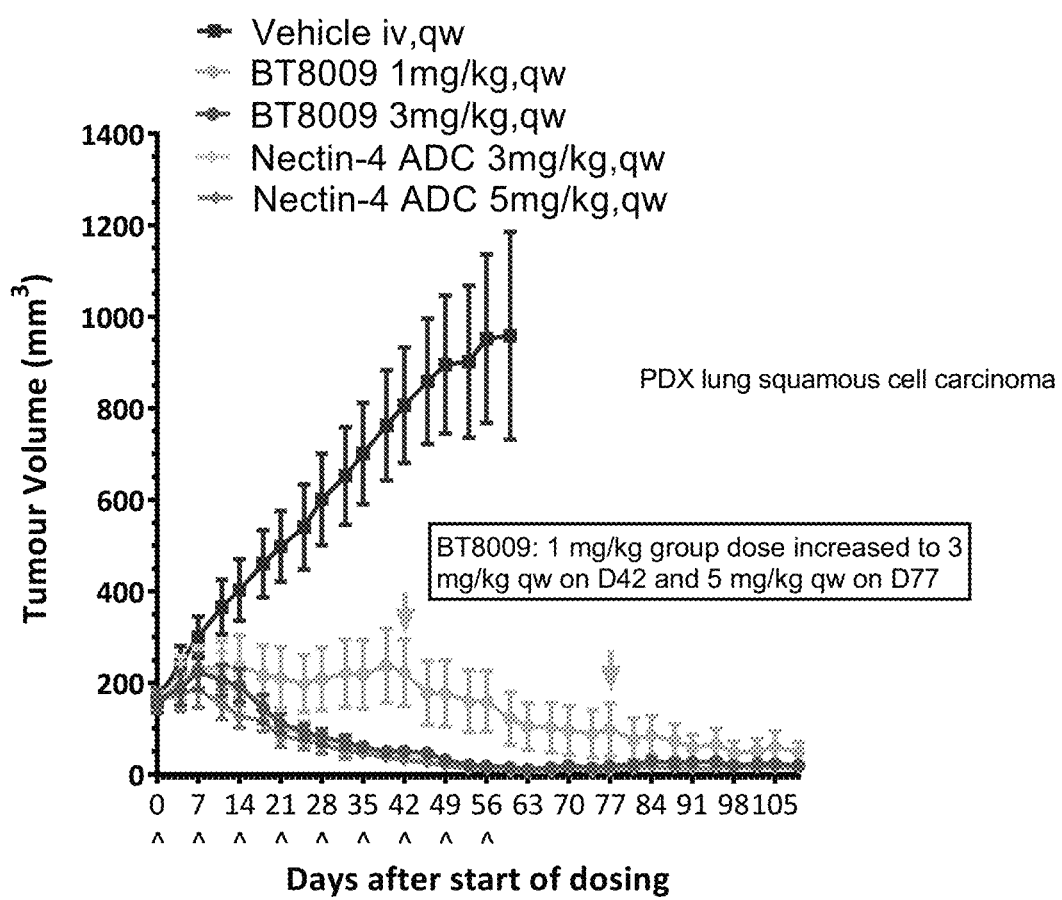
Figure 28:
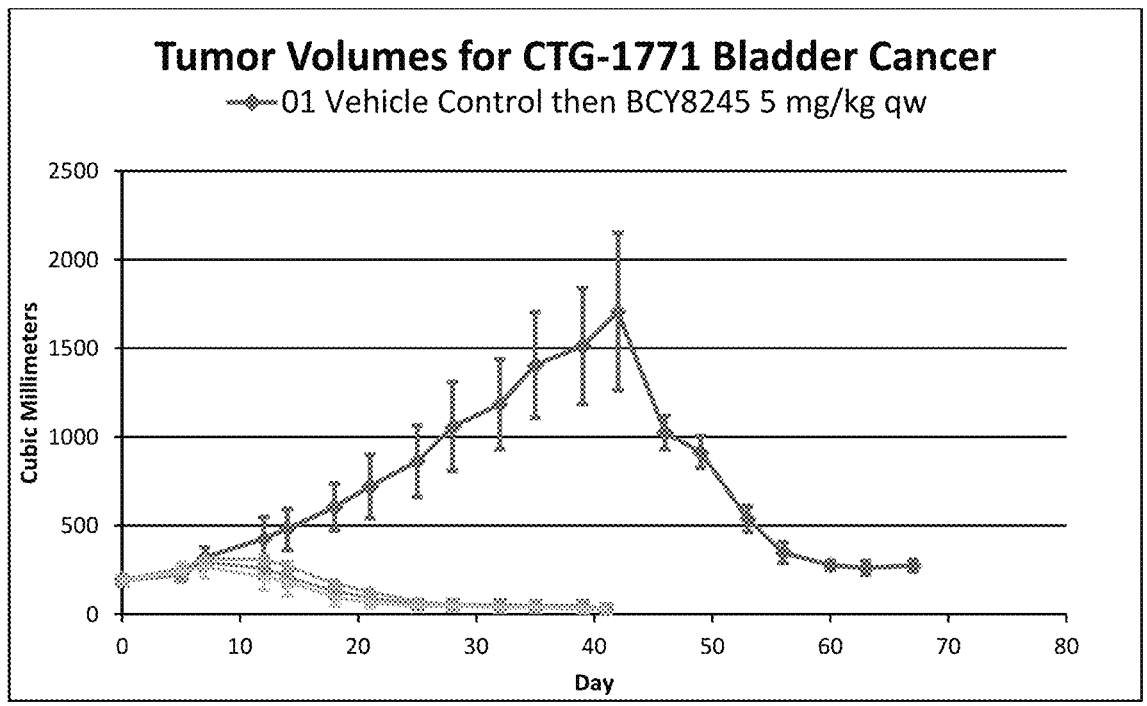
Figure 28:
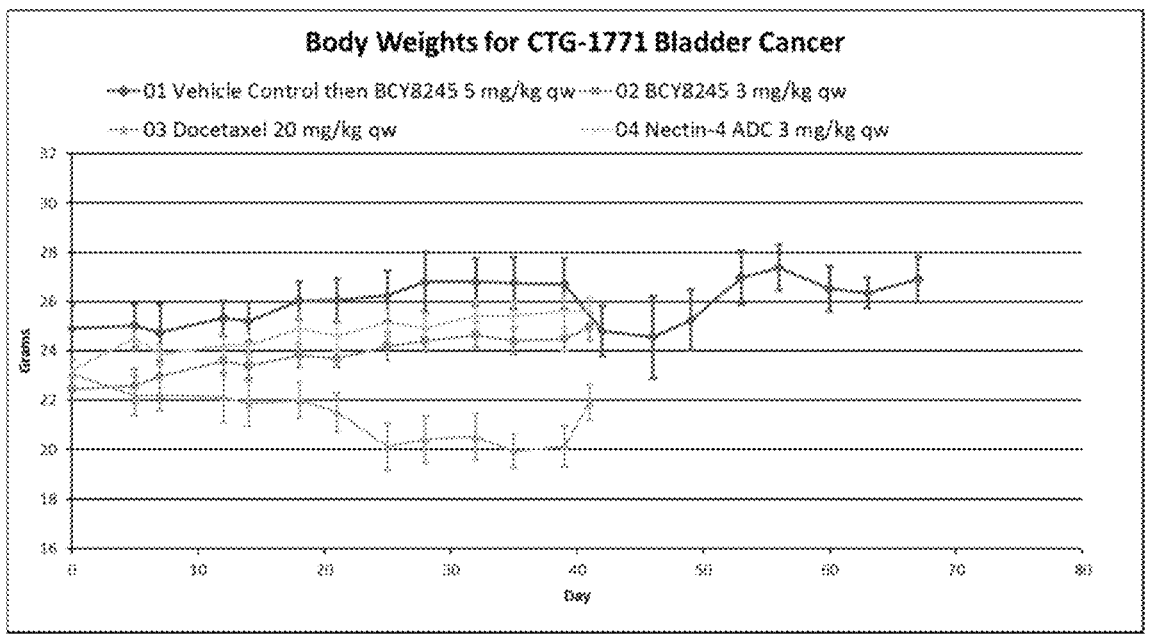
Figure 29:
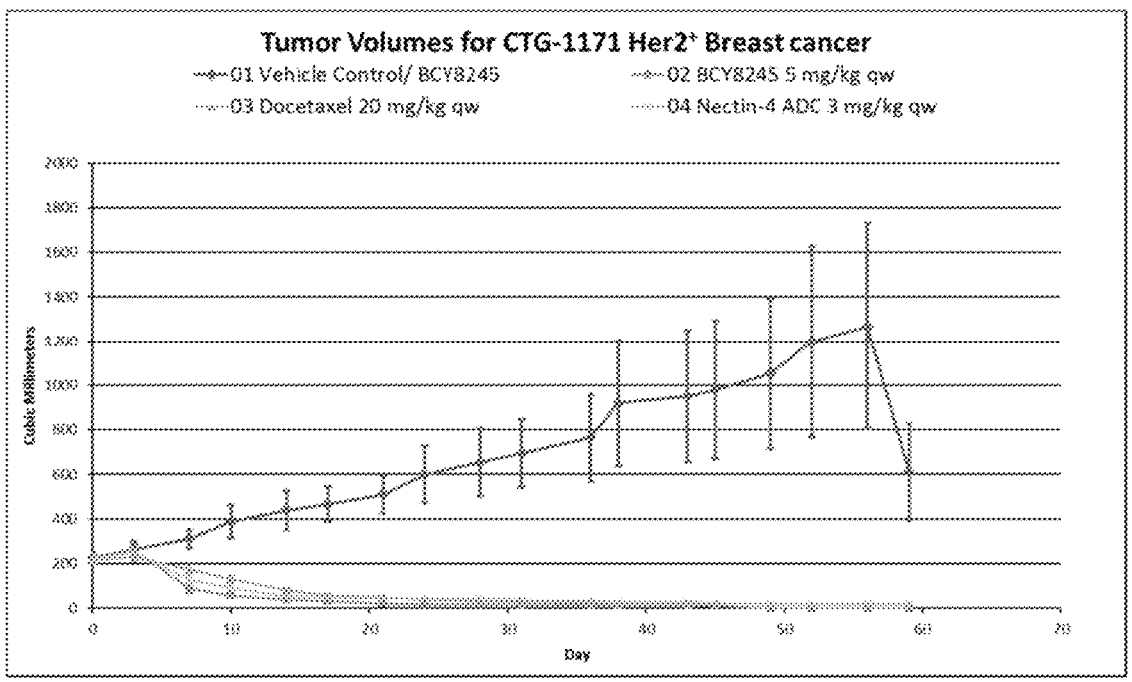
Figure 29:
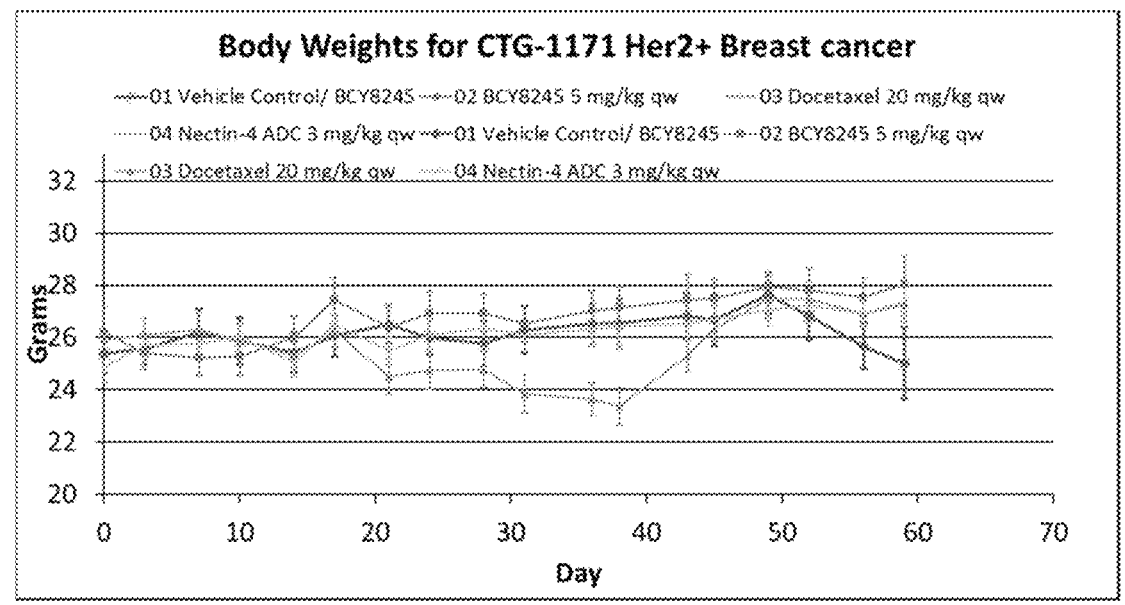
Figure 30:
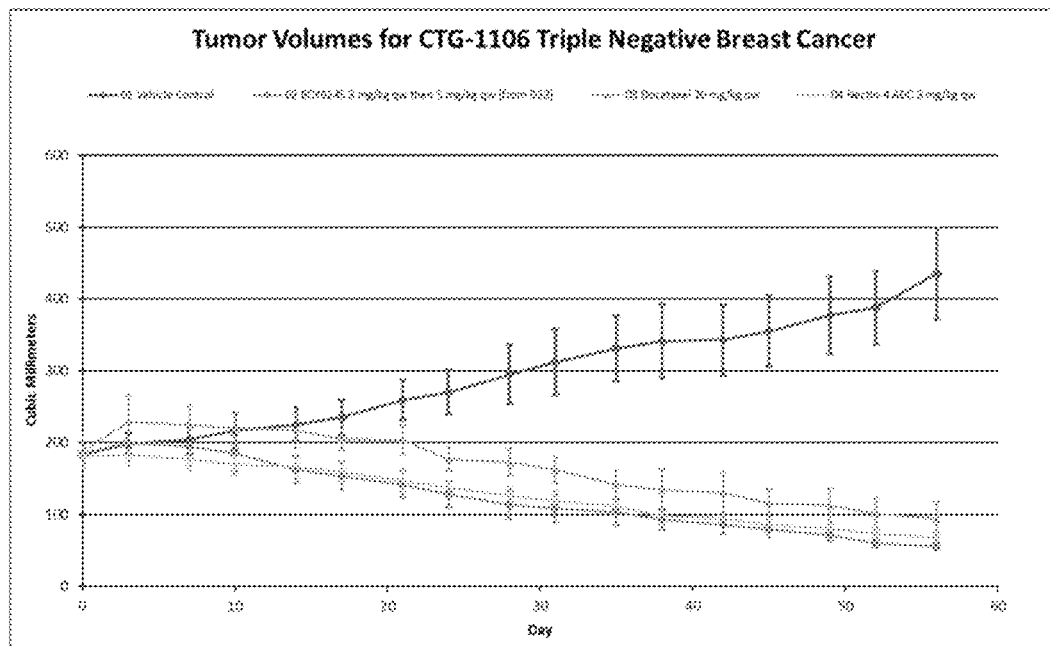
Figure 30:
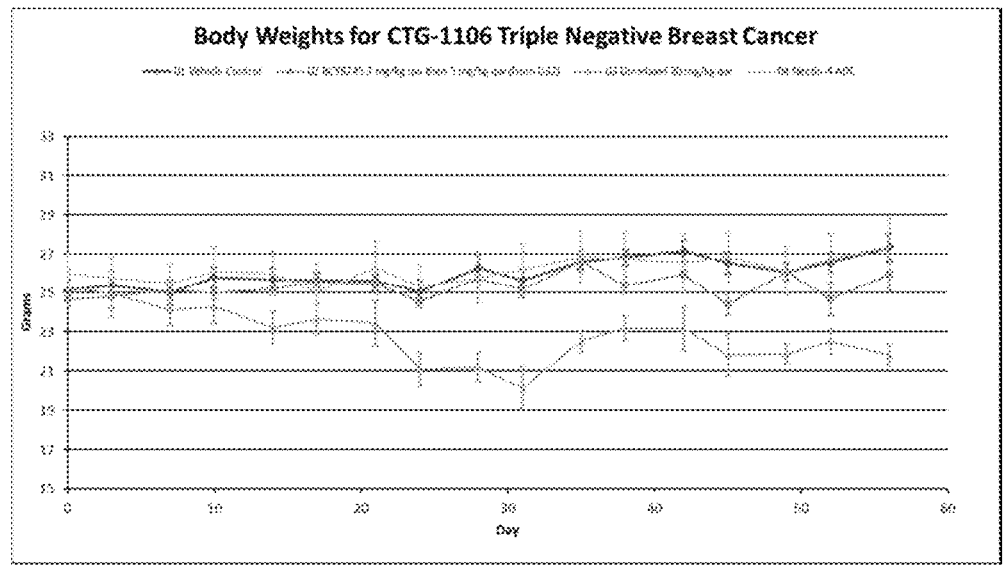
Figure 31:
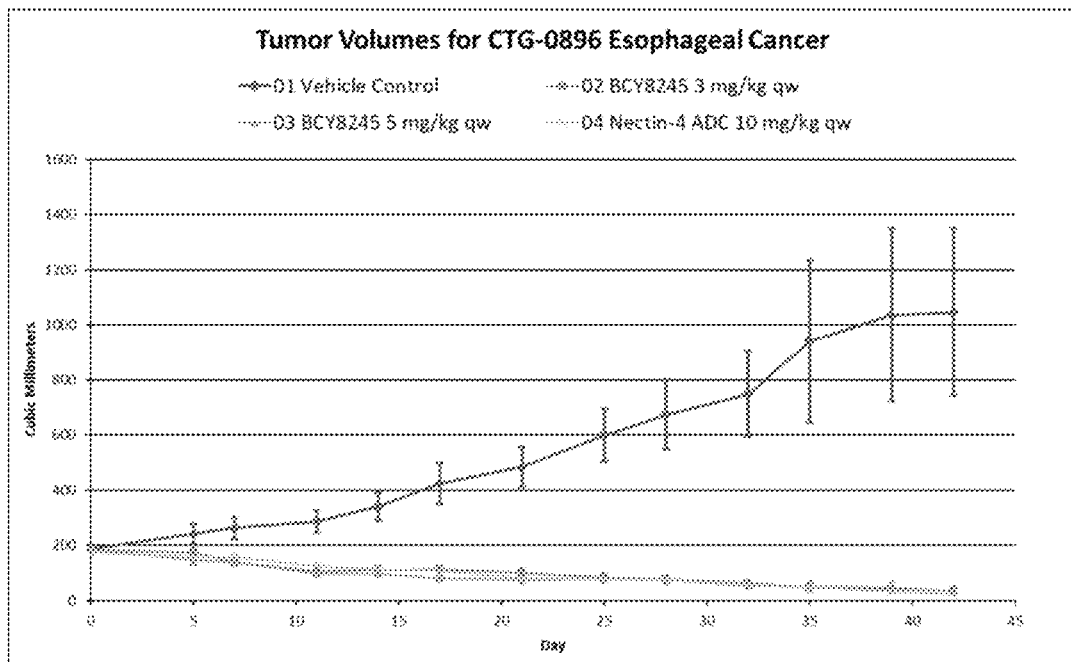
Figure 31:
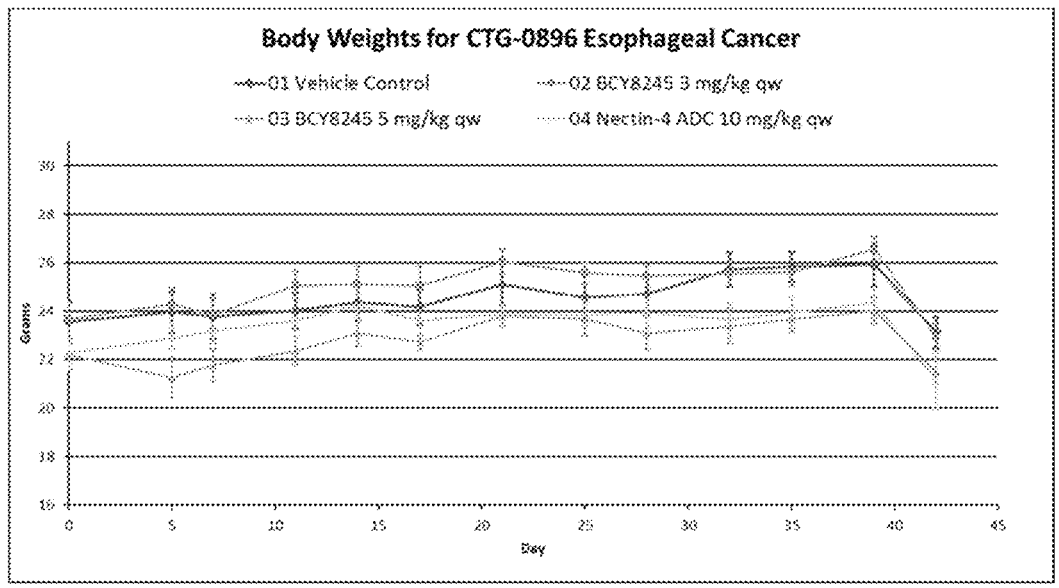
Figure 32:
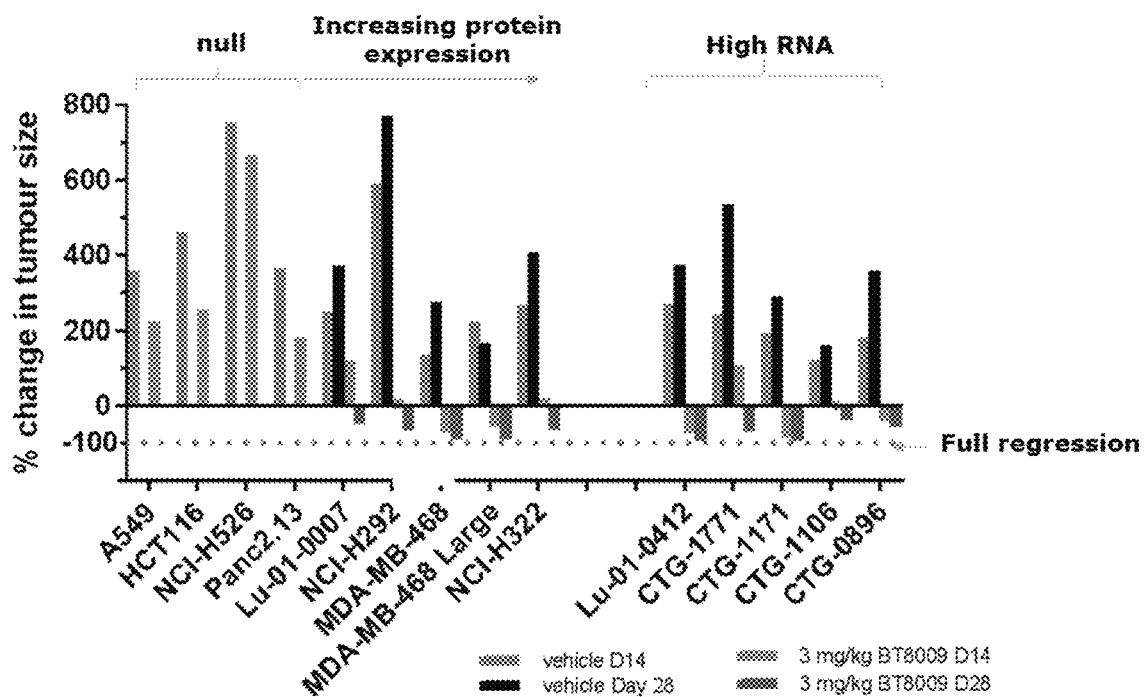
FIG. 32: BT8009 (i.e. BCY8245) efficacy correlates with expression CDX/PDX xenografts. Xenografts with little/no Nectin-4 expression show reduced tumour growth rate. Xenografts expressing Nectin-4 show regressions of tumour. Both PDX and CDX models are included in this analysis, values are collated from various reports.

The results of these studies are shown in FIGS. 26 and 27.

Lu-01-0412 (FIG. 26): BCY8245 produced a dose related efficacy in this PDX model with a reduction in tumour growth rate at 1 mg/kg qw but marked tumor regression at 3 mg/kg qw to baseline. After cessation of dosing (Day 21) 5/6 animals showed no tumour regrowth out to 105 days post study start. The single animal showing regrowth was responsive to 3 mg/kg BCY8245 and showed restored regression to baseline. BCY8781 the non-binding BDC produced stable disease at 3 mg/kg and on cessation of dosing tumor rapidly grew at the same rate as the vehicle treated group, emphasising the increased efficacy that Nectin-4 binding affords these agents. Large tumors (the vehicle treated group) regressed in response to a single dose of BCY8245 or BCY8781.

LU-01-0007 (FIG. 27): BCY8245 produced a dose related efficacy with 1 mg/kg qw producing stable disease and 3 mg/kg producing full regression. Dosing had to be maintained out to day 56 to attain full regression (when dosing was ceased). There was no tumor regrowth in this group out to beyond (the latter being maintained out to 126 days post study start). The Nectin-4 ADC gave a similar degree of efficacy. The 1 mg/kg stable disease group was responsive to increases in dosing (3 and 5 mg/kg) suggesting that low doses of BCY8245 do not lead to a development of resistance.

Example 13: In Vivo Evaluation of BCY8245 in Low Passage PDX Models of Human Breast, Esophageal and Bladder Cancer in Immunocompromised Mice Purpose To evaluate the antitumor activity of Bicycle Agent in Low Passage Champions TumorGraft Models of Human Breast, Esophageal, and Bladder Cancer in Immunocompromised mice.

Test System
Species: Mouse
Strain: Athymic Nude-Foxn1nu (Immune-compromised)
Source: Envigo: Indianapolis, Ind.
Gender: Female
Target age at initiation of dosing: At least 6-8 weeks of age
Target weight at initiation of dosing: At least 18 grams
Acclimation period: 3 days
Experimental Design Pre-study Animals: When sufficient stock animals reach 1.0-1.5 cm³, tumors will be harvested for re-implantation into pre-study animals. Pre-study animals will be implanted unilaterally on the left flank with tumor fragments harvested from stock animals. Each animal is implanted from a specific passage lot and documented.

Study Animals: Pre-study tumor volumes are recorded for each experiment beginning seven to ten days after implantation. When tumors reach an average tumor volume of 150-300 mm³, animals will be matched by tumor volume into treatment or control groups to be used for dosing and dosing initiated on Day 0.

Agents in Test

BCY8245 and Nectin-4 Antibody Drug conjugate, comparison with vehicle control. Standard of care agent Docetaxel may be included. All agents to be dosed qw by intravenous route, doses are indicated on graphs.

In Life Measurements

Efficacy Tumor Volume: Tumor volumes will be taken twice weekly. A final tumor volume will be taken on the day study reaches endpoint. If possible, a final tumor volume will be taken if an animal is found moribund.

Efficacy Animal Weights: Animals will be weighed twice weekly. A final weight will be taken on the day the study reaches end point or if animal is found moribund, if possible. Animals exhibiting ≥10% weight loss when compared to Day 0 will be provided DietGel® ad libitum. Any animal exhibiting >20% net weight loss for a period lasting 7 days or if mice display >30% net weight loss when compared to Day 0 will be considered moribund and euthanized.

Data Analysis

Agent Toxicity: Beginning on Day 0, animals will be observed daily and weighed twice weekly using a digital scale; data including individual and mean gram weights (Mean We±SEM), mean percent weight change versus Day 0 (% vD0) will be recorded for each group and % vD0 plotted at study completion. Animal deaths will be recorded daily and designated as drug-related (D), technical (T), tumor related (B), or unknown (U) based on weight loss and gross observation; single agent or combination groups reporting a mean % vD0 >20% and/or >10% mortality will be considered above the maximum tolerated dose (MTD) for that treatment on the evaluated regimen. Maximum mean % vD0 (weight nadir) for each treatment group is reported at study completion.

Agent Efficacy

Tumor Growth Inhibition—Beginning on Day 0, tumor dimensions are measured twice weekly by digital caliper and data including individual and mean estimated tumor volumes (Mean TV±SEM) recorded for each group; tumor volume is calculated using the formula (1): TV=width2× length×0.52. At study completion, percent tumor growth inhibition (% TGI) values will be calculated and reported for each treatment group (T) versus control (C) using initial (i) and final (f) tumor measurements by the formula (2): % TGI=1−(Tf−Ti)/(Cf−Ci). Individual mice reporting a tumor volume ≤30% of the Day 0 measurement for two consecutive measurements will be considered partial responders (PR). Individual mice lacking palpable tumors (0.00 mm$^3$ for two consecutive measurements) will be classified as complete responders (CR); a CR that persists until study completion will be considered a tumor-free survivor (TFS). Tumor doubling time (DT) will be determined for the vehicle treated groups using the formula DT=(Df−Di)*log 2/(log TVf−log TVi) where D=Day and TV=Tumor Volume. All data collected in this study is managed electronically and stored on a redundant server system.

The results of these studies are shown in FIGS. 28 to 31.

BCY8245 was tested in four low passage PDX models representing bladder cancer (CTG-1771), an estrogen and progesterone negative Her2 positive breast cancer (CTG-1171) a triple negative breast cancer (CTG-1106) and an esophageal cancer (CTG-0896). In all of these models BCY8245 showed excellent efficacy evoking tumor regression and in three of the four full regression to baseline. Efficacy was comparable to the ADC in all cases and superior or equal to Docetaxel SOC. In all models BCY8245 was better tolerated than Docetaxel.

The invention claimed is:

1. A peptide ligand specific for Nectin-4 comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold, wherein the peptide ligand comprises the amino acid sequence:

(SEQ ID NO: 1)
$C_iP[1Nal][dD]C_{ii}M[HArg]DWSTP[HyP]WC_{iii}$;

wherein 1Nal represents 1-naphthylalanine, HArg represents homoarginine, HyP represents hydroxyproline and $C_i$, $C_{ii}$ and $C_{iii}$ represent first, second and third cysteine residues, respectively, or a pharmaceutically acceptable salt thereof.

2. The peptide ligand according to claim 1, which comprises an amino acid sequence selected from:

[B-Ala][Sar10]-(SEQ ID NO: 1) (hereinafter referred to as BCY8234);

Ac[B-Ala][Sar5]-(SEQ ID NO: 1) (hereinafter referred to as BCY8122);

Ac-(SEQ ID NO: 1) (hereinafter referred to as BCY8126);

(SEQ ID NO: 1) (hereinafter referred to as BCY8116);

Fluorescein-(SEQ ID NO: 1) (hereinafter referred to as BCY8205);
and

[PYA][B-Ala][Sar10]-(SEQ ID NO: 1) (hereinafter referred to as BCY8846).

3. The peptide ligand according to claim 1, which comprises an amino acid sequence selected from:

[B-Ala][Sar10]-(SEQ ID NO: 1) (hereinafter referred to as BCY8234);

Ac-[B-Ala][Sar5]-(SEQ ID NO: 1) (hereinafter referred to as BCY8122);

Ac-(SEQ ID NO: 1) (hereinafter referred to as BCY8126);

(SEQ ID NO: 1) (hereinafter referred to as BCY8116);
and

Fluorescein-(SEQ ID NO: 1) (hereinafter referred to as BCY8205).

4. The peptide ligand according to claim 1, which comprises an amino acid sequence selected from:

Ac-[B-Ala][Sar5]-(SEQ ID NO: 1) (hereinafter referred to as BCY8122);

Ac-(SEQ ID NO: 1) (hereinafter referred to as BCY8126);
and (SEQ ID NO: 1) (hereinafter referred to as BCY8116).

5. The peptide ligand according to claim 1, which comprises an amino acid sequence selected from:

Ac-[B-Ala][Sar5]-(SEQ ID NO: 1) (hereinafter referred to as BCY8122);
and

Ac-(SEQ ID NO: 1) (hereinafter referred to as BCY8126).

6. The peptide ligand according to claim 1, which comprises an amino acid sequence:

[B-Ala][Sar10]-(SEQ ID NO: 1) (hereinafter referred to as BCY8234).

7. The peptide ligand according to claim 1, wherein the molecular scaffold is 1,1',1''-(1,3,5-triazinane-1,3,5-triyl)triprop-2-en-1-one (TATA).

8. The peptide ligand according to claim 1, wherein the pharmaceutically acceptable salt is selected from the free acid or the sodium, potassium, calcium, or ammonium salt.

9. The peptide ligand according to claim 1, wherein the Nectin-4 is human Nectin-4.

10. A pharmaceutical composition which comprises the peptide ligand of claim 1, in combination with one or more pharmaceutically acceptable excipients.

11. The pharmaceutical composition as defined in claim 10, which additionally comprises one or more therapeutic agents.

12. A drug conjugate comprising a peptide ligand as defined in claim 1, conjugated to one or more effector and/or functional groups.

13. The drug conjugate as defined in claim 12, conjugated to one or more cytotoxic agents.

14. The drug conjugate as defined in claim 13, wherein said cytotoxic agent is selected from Monomethyl auristatin E (MMAE) and Mertansine (DM1).

15. The drug conjugate as defined in claim 14, wherein the cytotoxic agent is MMAE and said conjugate additionally comprises a linker selected from: -PABC-Cit-Val-Glutaryl- and -PABC-cyclobutyl-Ala-Cit-βAla-, wherein PABC represents p-aminobenzylcarbamate.

16. The drug conjugate as defined in claim 15, wherein the cytotoxic agent is DM1 and said conjugate additionally comprises a linker which is -SPDB-($SO_3H$)—, wherein SPDB represents N-succinimidyl 3-(2-pyridyldithio)propionate.

17. The drug conjugate as defined in claim 15, wherein the linker is -PABC-Cit-Val-Glutaryl-.

18. The drug conjugate as defined in claim 12, which is selected from: BCY8245 and BCY8549.

19. The drug conjugate as defined in claim 18, which is BCY8245.

20. The drug conjugate as defined in claim 14, wherein said cytotoxic agent is MMAE.

21. A pharmaceutical composition which comprises the drug conjugate of claim 12, in combination with one or more pharmaceutically acceptable excipients.

22. A method for suppressing or treating a disease or disorder mediated by Nectin-4, comprising administering to a patient in need thereof the drug conjugate as defined in claim 12.

23. The method of claim 22, wherein the disease or disorder mediated by Nectin-4 is selected from bladder cancer, breast cancer, colorectal cancer, lung cancer, ovarian cancer, and pancreatic cancer.

24. A method of suppressing or treating a cancer patient having an increased copy number variation (CNV) of Nectin-4, which comprises administering to said patient in need thereof the drug conjugate as defined in claim 12.

* * * * *

UNITED STATES PATENT AND TRADEMARK OFFICE
CERTIFICATE OF CORRECTION

Page 1 of 1

PATENT NO. : 11,180,531 B2
APPLICATION NO. : 16/446901
DATED : November 23, 2021
INVENTOR(S) : Paul Beswick et al.

It is certified that error appears in the above-identified patent and that said Letters Patent is hereby corrected as shown below:

On the Title Page

Item [72], should be listed as follows:
(72) Inventors: Paul Beswick, Cambridge (GB);
Liuhong Chen, Cambridge (GB);
Gemma Mudd, Cambridge (GB);
Peter Park, Cambridge (GB);
Katerine Van Rietschoten, Cambridge (GB);
Michael Rigby, Cambridge (GB)
Stephen J. Blakemore, Cambridge (GB)
Tara Gelb, Cambridge (GB)
Nicholas Keen, Cambridge (GB)

Signed and Sealed this
Eleventh Day of November, 2025

John A. Squires
*Director of the United States Patent and Trademark Office*